United States Patent
Shin et al.

(10) Patent No.: US 10,446,760 B2
(45) Date of Patent: Oct. 15, 2019

(54) ORGANIC COMPOUND, ORGANIC OPTOELECTRIC DIODE, AND DISPLAY DEVICE

(71) Applicant: SAMSUNG SDI CO., LTD., Yongin-si, Gyeonggi-do (KR)

(72) Inventors: Chang-Ju Shin, Suwon-si (KR); Dong-Wan Ryu, Suwon-si (KR); Eun-Sun Yu, Suwon-si (KR); Han-Ill Lee, Suwon-si (KR); Chun-Keun Jang, Suwon-si (KR); Sung-Hyun Jung, Suwon-si (KR); Ju-Yeon Jung, Suwon-si (KR); Jin-Seok Hong, Suwon-si (KR); Bo-Hyung Kim, Suwon-si (KR); Chang-Woo Kim, Suwon-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 41 days.

(21) Appl. No.: 15/117,457

(22) PCT Filed: Apr. 8, 2015

(86) PCT No.: PCT/KR2015/003528
§ 371 (c)(1),
(2) Date: Aug. 9, 2016

(87) PCT Pub. No.: WO2015/174639
PCT Pub. Date: Nov. 19, 2015

(65) Prior Publication Data
US 2016/0351820 A1 Dec. 1, 2016

(30) Foreign Application Priority Data

May 12, 2014 (KR) .................. 10-2014-0056715
Apr. 7, 2015 (KR) .................. 10-2015-0048885

(51) Int. Cl.
*H01L 51/00* (2006.01)
*C07D 307/91* (2006.01)
*H01L 51/50* (2006.01)

(52) U.S. Cl.
CPC ........ *H01L 51/0061* (2013.01); *C07D 307/91* (2013.01); *H01L 51/006* (2013.01);
(Continued)

(58) Field of Classification Search
USPC ....... 428/690, 691, 917, 411.4, 336; 427/58, 427/66; 313/500–512; 257/40, 88–104,
(Continued)

(56) References Cited

U.S. PATENT DOCUMENTS

2011/0248246 A1 10/2011 Ogita et al.
2011/0266526 A1 11/2011 Ma et al.
(Continued)

FOREIGN PATENT DOCUMENTS

CN 102782084 A 11/2012
CN 103782410 A 5/2014
(Continued)

OTHER PUBLICATIONS

"Organic nano and molecular devices," May 31, 2010, p. 322 (with English Abstract).
(Continued)

*Primary Examiner* — Jennifer A Chriss
*Assistant Examiner* — Sean M DeGuire
(74) *Attorney, Agent, or Firm* — Lee & Morse, P.C.

(57) ABSTRACT

Disclosed are an organic compound represented by formula 1, an organic optoelectric diode applying the organic compound, and a display device comprising the organic optoelectric diode.

12 Claims, 1 Drawing Sheet

(52) U.S. Cl.
CPC ...... *H01L 51/0059* (2013.01); *H01L 51/0073* (2013.01); *H01L 51/5064* (2013.01)

(58) Field of Classification Search
USPC ................. 257/E51.052; 252/301.16–301.35
See application file for complete search history.

(56) References Cited

U.S. PATENT DOCUMENTS

2013/0099208 A1* 4/2013 Lee ..................... C07D 333/50
257/40
2014/0117326 A1 5/2014 Lee et al.

FOREIGN PATENT DOCUMENTS

| CN | 104638202 B | 5/2015 |
|---|---|---|
| JP | 2013-232520 A | 11/2013 |
| KR | 10-2012-0072784 A | 7/2012 |
| KR | 10-1165698 B1 | 7/2012 |
| KR | 101165698 B1 * | 7/2012 |
| KR | 10-2012-0116881 A | 10/2012 |
| KR | 10-2013-0007934 A | 1/2013 |
| KR | 10-2013-0042901 A | 4/2013 |
| KR | 10-2014-0019082 A | 2/2014 |

OTHER PUBLICATIONS

"Progress in Hole-Transport Materials for Use in Organic Light-Emitting Diodes," vol. 15 No. 6 Nov. 30, 2003, p. 495-504.
Chinese Search Report dated Jul. 14, 2017, of the corresponding Chinese Patent Application No. 291580015585.7.
Provisional double patenting rejection over claims of the above-identified appiication; USPTO Office action dated Jun. 27, 2018, in U.S. Appl. No. 15/417,454.

* cited by examiner

【FIG. 1】
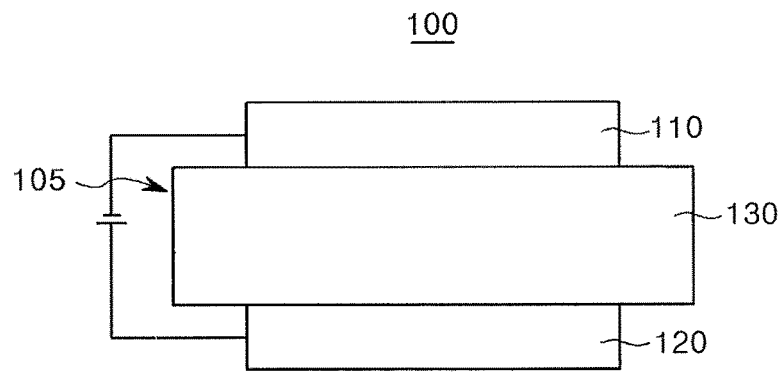
【FIG. 2】
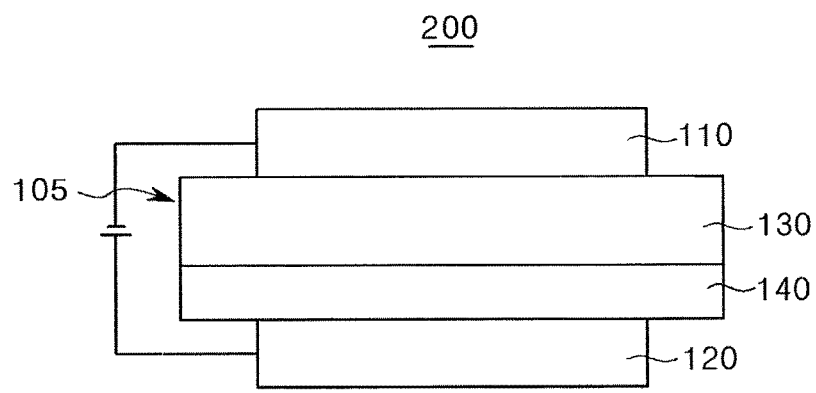
【FIG. 3】
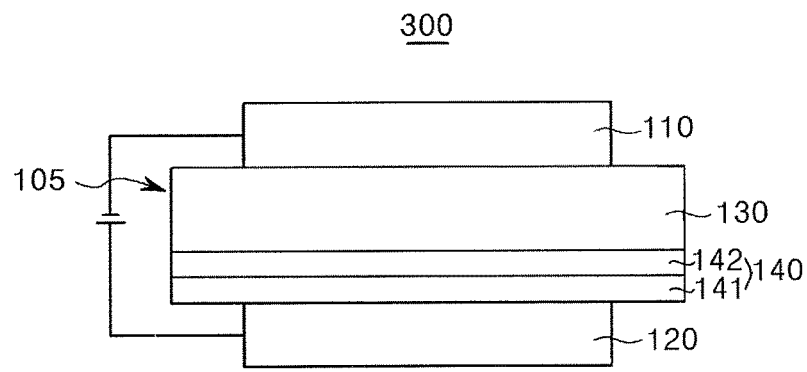

ORGANIC COMPOUND, ORGANIC OPTOELECTRIC DIODE, AND DISPLAY DEVICE

CROSS REFERENCE TO RELATED APPLICATIONS

This is the U.S. national phase application based on PCT Application No. PCT/KR2015/003528, filed Apr. 8, 2015, which is based on Korean Patent Application Nos. 10-2014-0056715, filed May 12, 2014, and 10-2015-0048885, filed Apr. 7, 2015, the entire contents of all of which are hereby incorporated by reference.

TECHNICAL FIELD

An organic compound, an organic optoelectric diode and a display device are disclosed.

BACKGROUND ART

An organic optoelectric diode is a device that converts electrical energy into photoenergy, and vice versa.

An organic optoelectric diode may be classified as follows in accordance with its driving principles. One is an optoelectric diode where excitons are generated by photoenergy, separated into electrons and holes, and are transferred to different electrodes to generate electrical energy, and the other is a light emitting diode where a voltage or a current is supplied to an electrode to generate photoenergy from electrical energy.

Examples of an organic optoelectric diode may be an organic photoelectric device, an organic light emitting diode, an organic solar cell and an organic photo conductor drum.

Of these, an organic light emitting diode (OLED) has recently drawn attention due to an increase in demand for flat panel displays. Such an organic light emitting diode converts electrical energy into light by applying current to an organic light emitting material. It has a structure in which an organic layer is interposed between an anode and a cathode.

Performance of an organic light emitting diode may be affected by characteristics of the organic layer, and among them, may be mainly affected by characteristics of an organic material of the organic layer. Particularly, development for an organic material capable of increasing hole and electron mobility and simultaneously increasing electrochemical stability is needed so that the organic light emitting diode may be applied to a large-size flat panel display.

DISCLOSURE

Technical Problem

One embodiment provides an organic compound capable of realizing an organic optoelectric diode having high efficiency and long life-span.

Another embodiment provides an organic optoelectric diode including the organic compound.

Yet another embodiment provides a display device including the organic optoelectric diode.

Technical Solution

According to one embodiment, an organic compound represented by the following Chemical Formula 1 is provided.

[Chemical Formula 1]

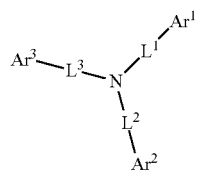

In Chemical Formula 1, $L^1$ to $L^3$ are each independently a single bond, a substituted or unsubstituted C6 to C30 arylene group, a substituted or unsubstituted C3 to C30 cycloalkylene group, a substituted or unsubstituted C2 to C30 heterocyclic group, a combination thereof or a combined fused ring of the foregoing groups, $Ar^1$ to $Ar^3$ are each independently a substituted or unsubstituted C6 to C30 aryl group, a substituted or unsubstituted C3 to C30 heterocyclic group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C6 to C30 aryloxy group, a substituted or unsubstituted C2 to C30 alkoxycarbonyl group, a substituted or unsubstituted C3 to C40 silyloxy group, a substituted or unsubstituted C1 to C30 acyl group, a substituted or unsubstituted C1 to C30 acyloxy group, a substituted or unsubstituted C2 to C30 acylamino group, a substituted or unsubstituted C2 to C30 alkoxycarbonylamino group, a substituted or unsubstituted C7 to C30 aryloxycarbonylamino group, a substituted or unsubstituted C1 to C30 sulfonyl group, a substituted or unsubstituted C1 to C30 sulfamoylamino group, a substituted or unsubstituted alkylthiol group, a substituted or unsubstituted C6 to C30 arylthiol group, a substituted or unsubstituted C1 to C30 heterocyclothiol group, a substituted or unsubstituted C1 to C20 ureide group, a substituted or unsubstituted C3 to C30 silyl group, a substituted or unsubstituted C1 to C30 amine group, a nitro group, a substituted or unsubstituted C1 to C30 carboxyl group, a ferrocenyl group, a combination thereof, a combined fused ring of the foregoing groups, or a group represented by the following Chemical Formula A, and at least one of $Ar^1$ to $Ar^3$ is a group represented by the following Chemical Formula A,

[Chemical Formula A]

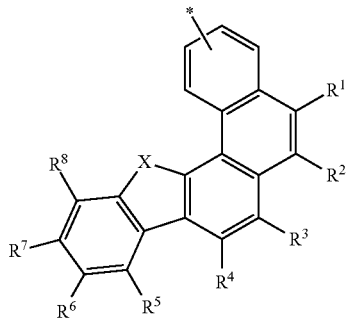

wherein, in Chemical Formula A,

X is O or S, $R^1$ to $R^8$ are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C2 to C10 vinyl group, a substituted or unsubstituted C6 to C30 aryl group, substituted or unsubstituted C2 to C30 heterocyclic group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and

* indicates a linking point.

According to another embodiment, an organic optoelectric diode includes an anode and a cathode facing each other and at least one organic layer positioned between the anode and the cathode, wherein the organic layer includes the organic compound.

According to another embodiment, a display device including the organic optoelectric diode is provided.

Advantageous Effects

An organic optoelectric diode having high efficiency and long life-span may be realized.

DESCRIPTION OF DRAWINGS

FIGS. 1 to 3 are each a cross-sectional view of an organic light emitting diode according to one embodiment.

BEST MODE

Hereinafter, embodiments of the present invention are described in detail. However, these embodiments are exemplary, and this disclosure is not limited thereto.

As used herein, when a definition is not otherwise provided, the term "substituted" refers to one substituted with a substituent selected from deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, C6 to C30 aryl group, a C6 to C30 heterocyclic group, a C1 to C20 alkoxy group, a fluoro group, a C1 to C10 trifluoroalkyl group such as a trifluoromethyl group and the like or a cyano group, instead of at least one hydrogen of a substituent or a compound.

In addition, two adjacent substituents selected from the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heterocyclic group, C1 to C20 alkoxy group, fluoro group, C1 to C10 trifluoroalkyl group such as a trifluoromethyl group and the like or cyano group may be fused to each other to form a ring. For example, the substituted C6 to C30 aryl group may be fused to another adjacent substituted C6 to C30 aryl group to form a substituted or unsubstituted fluorene ring.

In the present specification, when specific definition is not otherwise provided, "hetero" refers to one including 1 to 3 hetero atoms selected from N, O, S, P, and Si, and remaining carbons in one functional group.

As used herein, "an aryl group" refers to a group having at least one hydrocarbon aromatic ring moiety, and broadly includes hydrocarbon aromatic ring moieties linked by a single bond and a non-aromatic fused ring including hydrocarbon aromatic ring moieties fused directly or indirectly. An aryl group may be monocyclic, polycyclic or fused polycyclic (i.e., rings sharing adjacent pairs of carbon atoms) group.

As used herein, "a heterocyclic group" includes a heteroaryl group, and a cyclic group including at least one heteroatom selected from N, O, S, P, and Si, instead of carbon (C) of a cyclic compound such as an aryl group, a cycloalkyl group, a fused ring or a combination thereof. When the heterocyclic group is a fused ring, each or entire ring of the heterocyclic group may include at least one heteroatom.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazole group, a combination thereof, or a combined fused ring of the foregoing groups, but is not limited thereto.

As used herein, a substituted or unsubstituted arylene group or a substituted or unsubstituted heteroarylene group refers to a substituted or unsubstituted aryl group or a substituted or unsubstituted heteroaryl group which is defined above and has two linking points, for example, a substituted or unsubstituted phenylene group, a substituted or unsubstituted naphthylene group, a substituted or unsubstituted anthracenylene group, a substituted or unsubstituted phenanthrylene group, a substituted or unsubstituted naphthacenylene group, a substituted or unsubstituted pyrenylene group, a substituted or unsubstituted biphenylene group, a substituted or unsubstituted terphenylene group, a substituted or unsubstituted quaterphenylene group, a substituted or unsubstituted chrysenylene group, a substituted or unsubstituted triphenylenylene group, a substituted or unsubstituted perylenylene group, a substituted or unsubstituted indenylene group, a substituted or unsubstituted furanylene group, a substituted or unsubstituted thiophenylene group, a substituted or unsubstituted pyrrolylene group, a substituted or unsubstituted pyrazolylene group, a substituted or unsubstituted iimidazolylene group, a substituted or unsubstituted triazolylene group, a substituted or unsubstituted oxazolylene group, a substituted or unsubstituted thiazolyiene group, a substituted or unsubstituted oxadiazolylene group, a substituted or unsubstituted thiadiazolylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted benzofuranylene group, a substituted or unsubstituted benzothiophenylene group, a substituted or unsubstituted benzimidazolylene group, a substituted or unsubstituted indolylene group, a substituted or unsubstituted quinolinylene group, a substituted or unsubstituted isoquinolinylene group, a substituted or unsubstituted quinazolinylene group, a substituted or unsubstituted quinoxalinylene group, a substituted or unsubstituted naphthyridinylene group, a substituted or unsubstituted benzoxazinylene group, a substituted or unsubstituted benzthiazinylene group, a substituted or unsubstituted acridinylene group, a substituted or unsubstituted phenazinylene group, a substituted or unsubstituted phenothiazinylene group, a substituted or unsubstituted phenoxazinylene group, a substituted or unsubstituted fluorenylene group, a substituted or unsubstituted dibenzofuranylene group, a substituted or unsubstituted dibenzothiophenylene group, a substituted or unsubstituted carbazolylene group, a combination thereof, or a combined fused ring of the foregoing groups, but is not limited thereto.

In the specification, hole characteristics refer to characteristics in which an electron can be donated to form a hole when electric field is applied, and characteristics in which a hole formed in the anode is easily injected into the emission layer and transported in the emission layer due to conductive characteristics according to HOMO level.

In addition, electron characteristics refer to characteristics in which an electron can be accepted when electric field is applied, and characteristics in which an electron formed in the cathode is easily injected into the emission layer and transported in the emission layer due to conductive characteristics according to LUMO level.

Hereinafter, an organic compound according to one embodiment is described.

An organic compound according to one embodiment is represented by the following Chemical Formula 1.

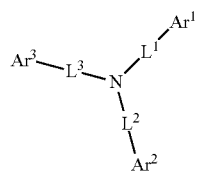

[Chemical Formula 1]

In Chemical Formula 1, $L^1$ to $L^3$ are each independently a single bond, a substituted or unsubstituted C6 to C30 arylene group, a substituted or unsubstituted C3 to C30 cycloalkylene group, a substituted or unsubstituted C2 to C30 heterocyclic group, a combination thereof or a combined fused ring of the foregoing groups, $Ar^1$ to $Ar^3$ are each independently a substituted or unsubstituted C6 to C30 aryl group, a substituted or unsubstituted C3 to C30 heterocyclic group, a substituted or unsubstituted C3 to C30 cycloalkyl group, a substituted or unsubstituted C3 to C30 cycloalkenyl group, a substituted or unsubstituted C1 to C30 alkoxy group, a substituted or unsubstituted C6 to C30 aryloxy group, a substituted or unsubstituted C2 to C30 alkoxycarbonyl group, a substituted or unsubstituted C3 to C40 silyloxy group, a substituted or unsubstituted C1 to C30 acyl group, a substituted or unsubstituted C1 to C30 acyloxy group, a substituted or unsubstituted C2 to C30 acylamino group, a substituted or unsubstituted C2 to C30 alkoxycarbonylamino group, a substituted or unsubstituted C7 to O30 aryloxycarbonylamino group, a substituted or unsubstituted C1 to C30 sulfonyl group, a substituted or unsubstituted C1 to C30 sulfamoylamino group, a substituted or unsubstituted alkylthiol group, a substituted or unsubstituted C6 to C30 arylthiol group, a substituted or unsubstituted C1 to C30 heterocyclothiol group, a substituted or unsubstituted C1 to C20 ureide group, a substituted or unsubstituted C3 to C30 silyl group, a substituted or unsubstituted C1 to C30 amine group, a nitro group, a substituted or unsubstituted C1 to C30 carboxyl group, a ferrocenyl group, a combination thereof, a combined fused ring of the foregoing groups, or a group represented by the following Chemical Formula A, and at least one of $Ar^3$ to $Ar^3$ is a group represented by the following Chemical Formula A,

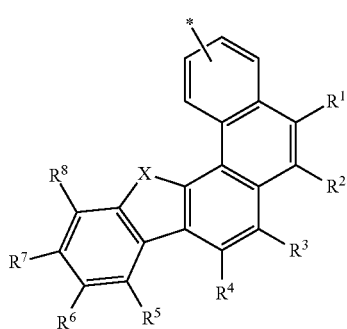

[Chemical Formula A]

wherein, in Chemical Formula A,

X is O or S, $R^1$ to $R^8$ are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C2 to C10 vinyl group, a substituted or unsubstituted C6 to C30 aryl group, substituted or unsubstituted C2 to C30 heterocyclic group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and \* indicates a linking point.

The organic compound represented by Chemical Formula 1 is an amine compound substituted with a fused ring having a hetero atom, and the amine compound is combined with the outermost ring of the fused ring having a hetero atom.

In the organic light emitting diode, a layer neighboring an emission layer (a hole transport layer, an electron transport layer), particularly, the hole transport layer should have a high LUMO energy level to effectively block electrons transported from the electron transport layer through the emission layer as well as satisfy a high S1 energy level to increase luminous efficiency and life-span. The organic compound represented by Chemical Formula 1 has higher S1 energy level and LUMO energy level when the amine compound is combined with the outermost ring of the fused ring than when the amine compound is combined with the middle of the the fused ring and thus, may increase efficiency and life-span of an organic light emitting diode as shown in Table 1.

In the following Table 1, HOMO, LUMO and S1 energy levels are obtained by optimizing the structure of a compound in a B3LYP/6-31G (d, p) level by using a DFT method of a Gaussian program.

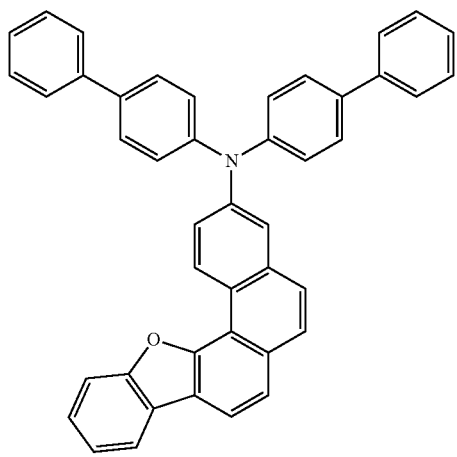

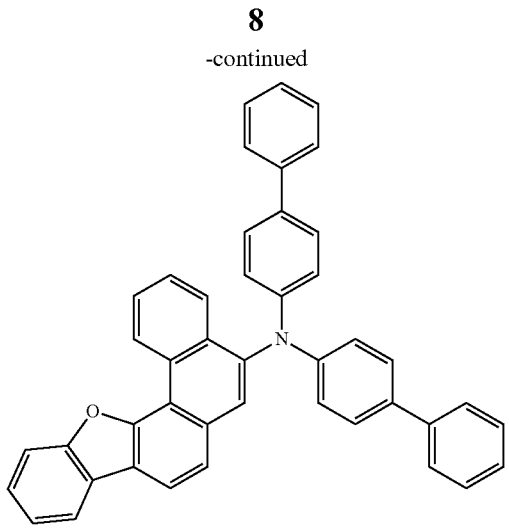

<Chemical Formula A-1> <Comparison Compound>

TABLE 1

| | HOMO (eV) | LUMO (eV) | S1 energy level (eV) |
|---|---|---|---|
| Chemical Formula A-1 | −4.88 | −1.32 | 3.08 |
| Comparison compound | −4.93 | −1.45 | 2.97 |

In Chemical Formula 1, at least one of $Ar^1$ to $Ar^3$ may be the group represented by Chemical Formula A, for example 1 to 3 of the group represented by Chemical Formula A.

In $Ar^1$ to $Ar^3$ of Chemical Formula 1, the remaining groups except the group represented by Chemical Formula A may each independently be a substituted or unsubstituted C6 to C30 aryl group, a substituted or unsubstituted C3 to C30 heterocyclic group, a substituted or unsubstituted C3 to C30 cycloalkyl group, a combination thereof or a combined fused ring of the foregoing groups.

For example, in $Ar^1$ to $Ar^3$, the remaining groups except the group represented by Chemical Formula A may each independently be one of groups listed in the following Group 1, but are not limited thereto.

[Group 1]

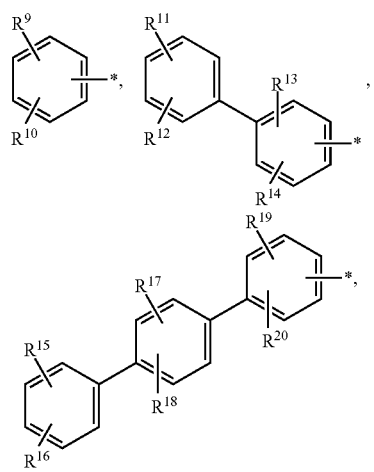

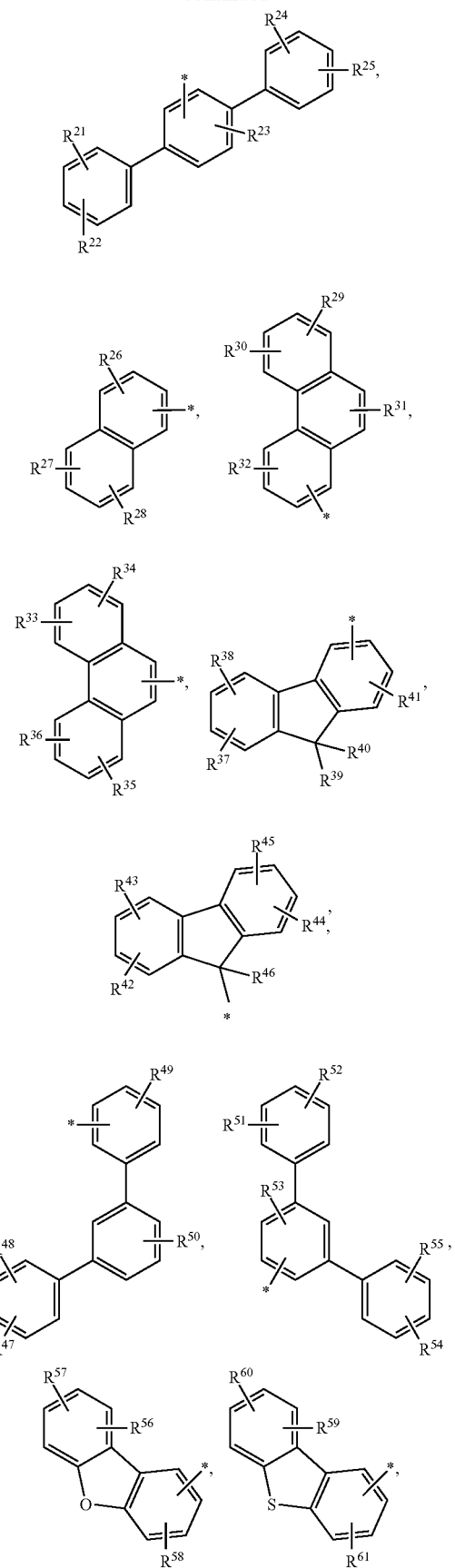

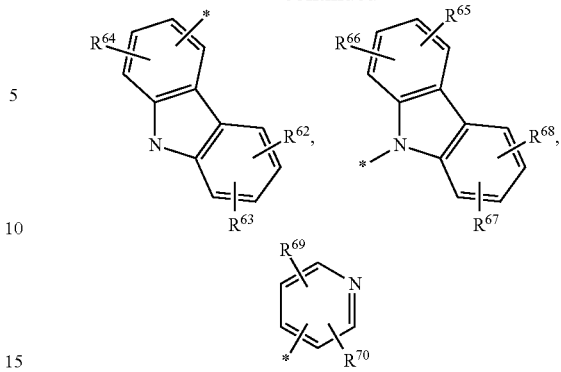

In Group 1,
R$^9$ to R$^{70}$ are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C2 to C10 vinyl group, a substituted or unsubstituted C6 to C30 aryl group, substituted or unsubstituted C2 to C30 heterocyclic group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and

* indicates a linking point.

In Chemical Formula A, for example R$^1$ to R$^8$ may be each independently hydrogen.

In Chemical Formula A, for example R$^1$ to R$^4$ may be each independently hydrogen.

The organic compound may be represented by one of the following Chemical Formulae 2 to 4 according to the number of the group represented by Chemical Formula A.

[Chemical Formula 2]

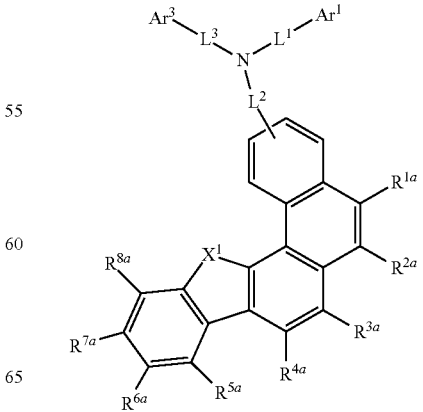

-continued

[Chemical Formula 3]

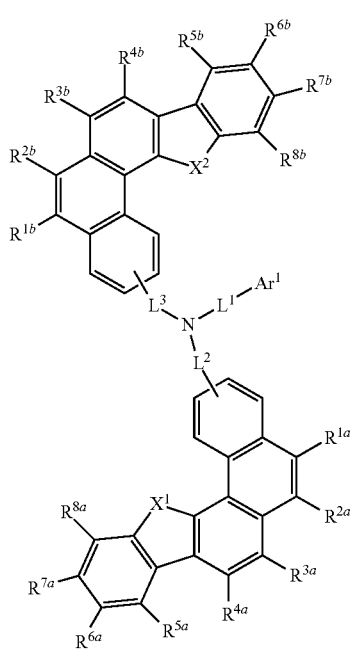

[Chemical Formula 4]

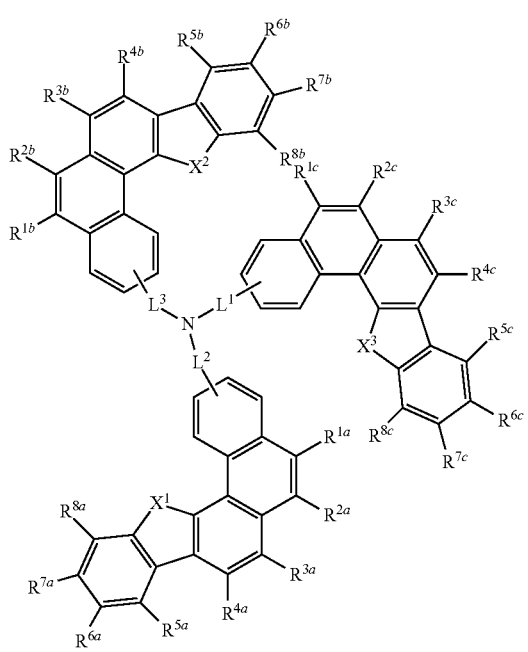

In the Chemical Formulae 2 to 4, $X^1$ to $X^3$, $L^1$ to $L^3$, $Ar^1$ and $Ar^3$ are the same as described above, and $R^{1a}$ to $R^{8a}$, $R^{1b}$ to $R^{8b}$ and $R^{1c}$ to $R^{8c}$ are each independently the same as $R^1$ to $R^8$.

For example, in Chemical Formulae 2 to 4, $Ar^1$ and $Ar^3$ may each independently be a substituted or unsubstituted C6 to C30 aryl group, a substituted or unsubstituted C3 to C30 heterocyclic group, a substituted or unsubstituted C3 to C30 cycloalkyl group, a combination thereof, or a combined fused ring of the foregoing groups. For example, $Ar^1$ and $Ar^3$ are each independently selected from groups listed in Group 1, but are not limited thereto.

For example, in Chemical Formulae 2 to 4, $R^{1a}$ to $R^{8a}$, $R^{1b}$ to $R^{8b}$ and $R^{1c}$ to $R^{8c}$ may each independently be hydrogen.

For example, in Chemical Formulae 2 to 4, $R^{1a}$ to $R^{4a}$, $R^{1b}$ to $R^{4b}$ and $R^{1c}$ to $R^{4c}$ may each independently be hydrogen.

Chemical Formula 2 may be, for example represented by one of the following Chemical Formulae 2-I to 2-III according to the bonding position.

[Chemical Formula 2-I]

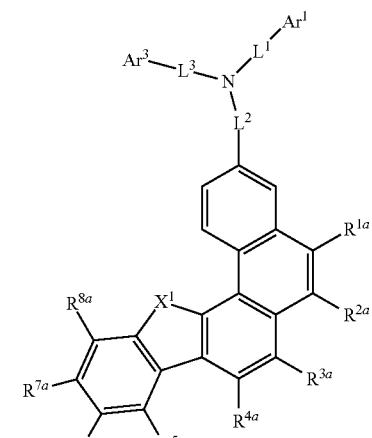

[Chemical Formula 2-II]

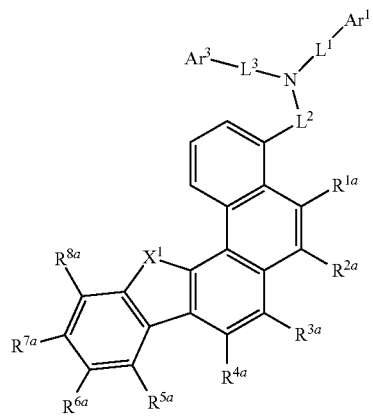

[Chemical Formula 2-III]

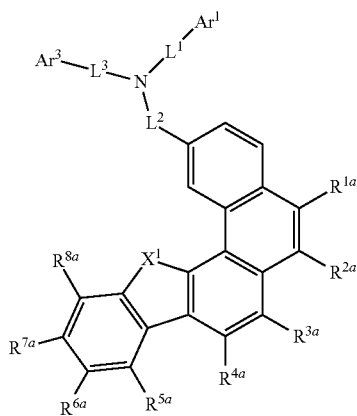

In Chemical Formulae 2-I to 2-III, $X^1$, $L^1$ to $L^3$, $Ar^1$, $Ar^3$ and $R^{1a}$ to $R^{8a}$ are the same as described above.

For example, in Chemical Formulae 2-I to 2-III, $Ar^1$ and $Ar^3$ may each independently be a substituted or unsubstituted C6 to C30 aryl group, a substituted or unsubstituted C3 to C30 heterocyclic group, a substituted or unsubstituted C3 to C30 cycloalkyl group, a combination thereof or a combined fused ring of the foregoing groups. For example, $Ar^1$ and $Ar^3$ are each independently selected from groups listed in Group 1, but are not limited thereto.

For example, in Chemical Formulae 2-I to 2-III, $R^{1a}$ to $R^{8a}$ may each independently be hydrogen.

For example, in Chemical Formulae 2-I to 2-III, $R^{1a}$ to $R^{4a}$ may each independently be hydrogen.

Chemical Formula 3 may be, for example represented by one of the following Chemical Formulae 3-I to 3-III according to the bonding position.

[Chemical Formula 3-I]

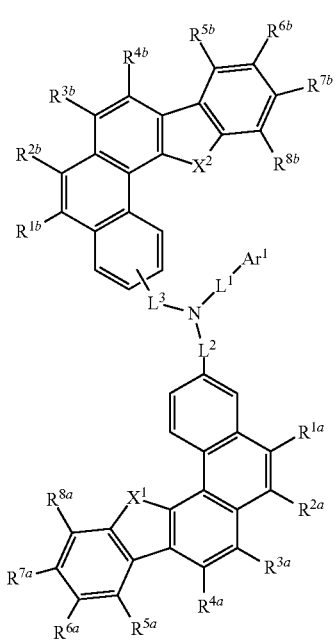

[Chemical Formula 3-II]

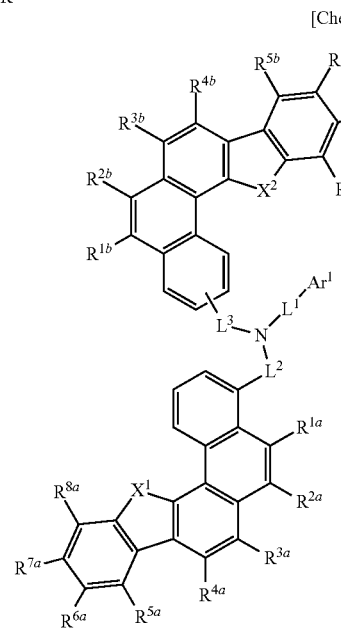

[Chemical Formula 3-III]

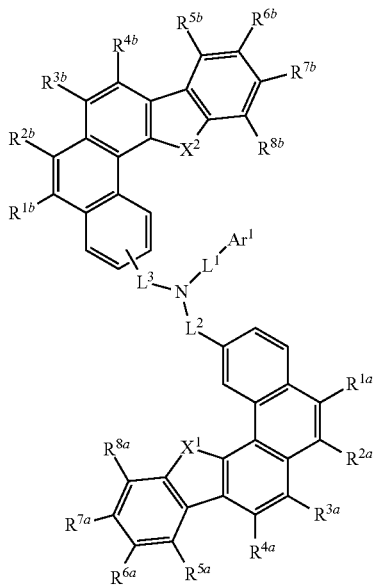

In Chemical Formulae 3-I to 3-III, $X^1$, $X^2$, $L^1$ to $L^3$, $Ar^1$, $R^{1a}$ to $R^{8a}$ and $R^{1b}$ to $R^{8b}$ are the same as described above.

For example, in Chemical Formulae 3-I to 3-IIII, $Ar^1$ may be a substituted or unsubstituted C6 to C30 aryl group, a substituted or unsubstituted C3 to C30 heterocyclic group, a substituted or unsubstituted C3 to C30 cycloalkyl group, a combination thereof or a combined fused ring of the foregoing groups. For example, $Ar^1$ may be selected from groups listed in Group 1, but is not limited thereto.

For example, in Chemical Formulae 3-I to 3-III, $R^{1a}$ to $R^{8a}$ and $R^{1b}$ to $R^{8b}$ are each independently hydrogen.

For example, in Chemical Formulae 3-I to 3-III, $R^{1a}$ to $R^{4a}$ and $R^{1b}$ to $R^{4b}$ are each independently hydrogen.

Chemical Formula 4 may be, for example represented by one of the following Chemical Formulae 4-I to 4-III according to the bonding position.

[Chemical Formula 4-I]

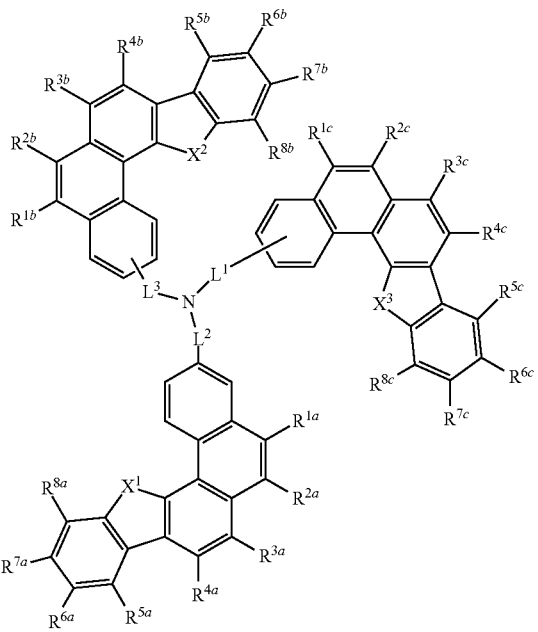

[Chemical Formula 4-II]

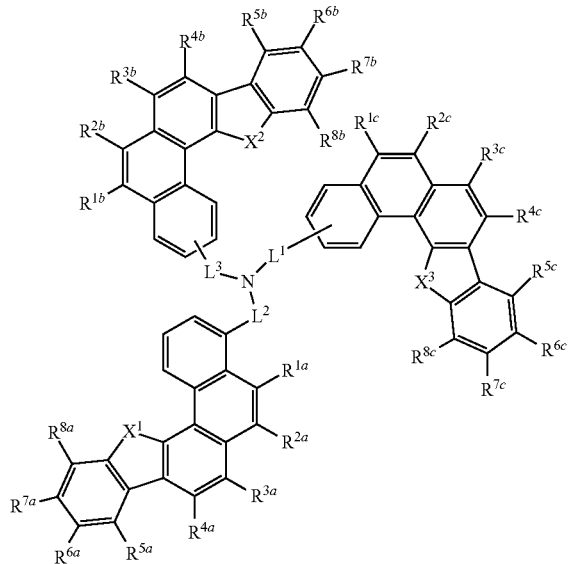

[Chemical Formula 4-III]

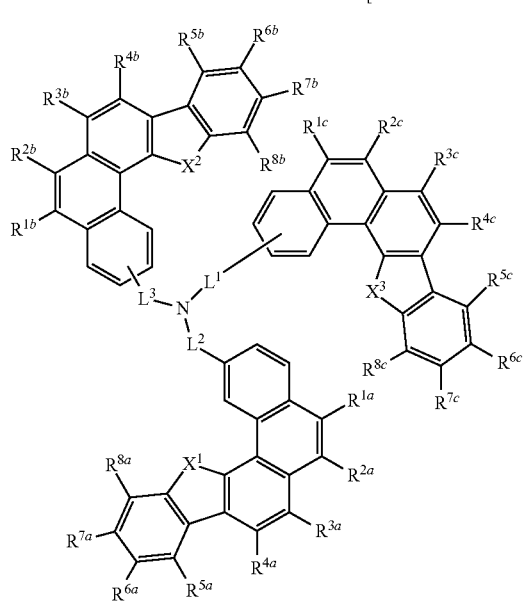

In Chemical Formulae 4-I to 4-III, $X^1$, $X^2$, $X^3$, $L^1$ to $L^3$, $R^{1a}$ to $R^{8a}$, $R^{1b}$ to $R^{8b}$ and $R^{1c}$ to $R^{8c}$ are the same as described above.

For example, in Chemical Formulae 4-I to 4-III, $R^{1a}$ to $R^{8a}$, $R^{1b}$ to $R^{8b}$ and $R^{1c}$ to $R^{8c}$ may each independently be hydrogen.

For example, in Chemical Formulae 4-I to 4-III, $R^{1a}$ to $R^{4a}$, $R^{1b}$ to $R^{4b}$ and $R^{1c}$ to $R^{4c}$ may each independently be hydrogen.

$L^1$ to $L^3$ in Chemical Formulae 1 to 4, 2-I to 2-III, 3-I to 3-III, 4-I to 4-III may each independently be, for example a single bond, a substituted or unsubstituted phenylene group, a substituted or unsubstituted biphenylene group, a substituted or unsubstituted terphenylene group, a substituted or unsubstituted quaterphenylene group, a substituted or unsubstituted naphthylene group, a substituted or unsubstituted anthracenylene group, a substituted or unsubstituted phenanthrylene group, a substituted or unsubstituted fluorenylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted dibenzofuranylene group, a substituted or unsubstituted dibenzothiophenylene group, a substituted or unsubstituted carbazolylene group, a combination thereof, or a combined fused ring of the foregoing groups.

For example, $L^1$ to $L^3$ in Chemical Formulae 1 to 4, 2-I to 2-III, 3-I to 3-III, 4-I to 4-III may each independently be a single bond, a substituted or unsubstituted phenylene group, a substituted or unsubstituted biphenylene group, a substituted or unsubstituted fluorenylene group, a substituted or unsubstituted pyridinylene group, a substituted or unsubstituted dibenzofuranylene group, a substituted or unsubstituted dibenzothiophenylene group, a substituted or unsubstituted carbazolylene group, a combination thereof, or a combined fused ring of the foregoing groups.

The organic compound may be, for example one of compounds listed in the following Group 2, but is not limited thereto.

[Group 2]

A-1

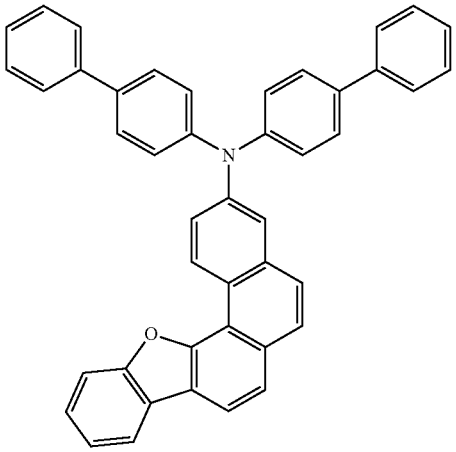

A-2

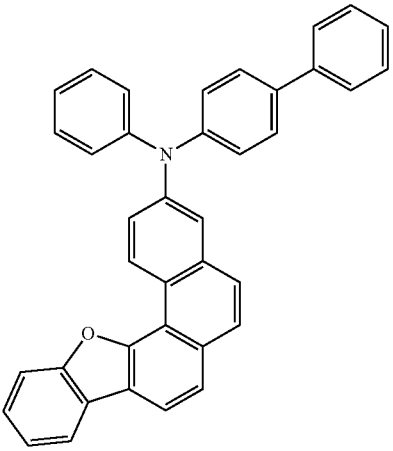

A-3
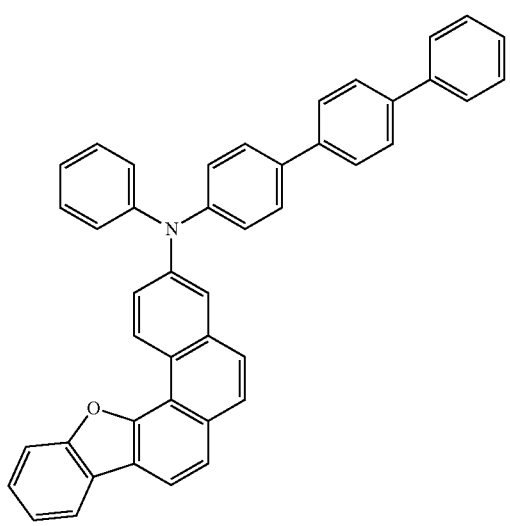
A-6
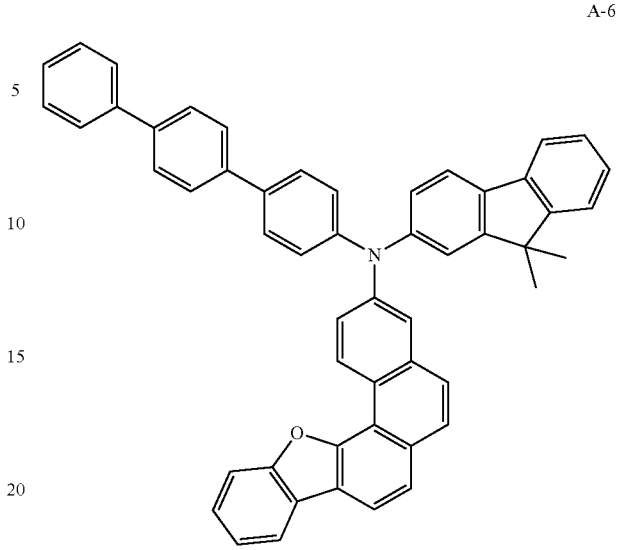
A-4
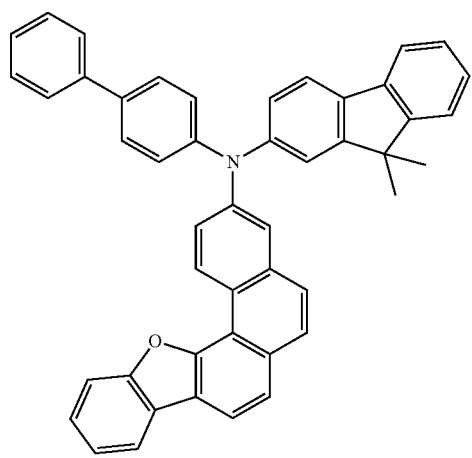
A-7
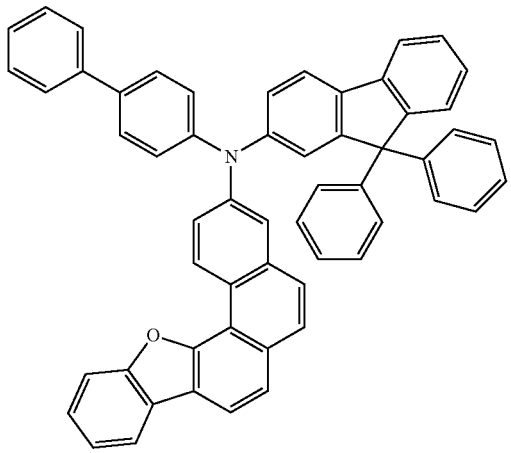
A-5
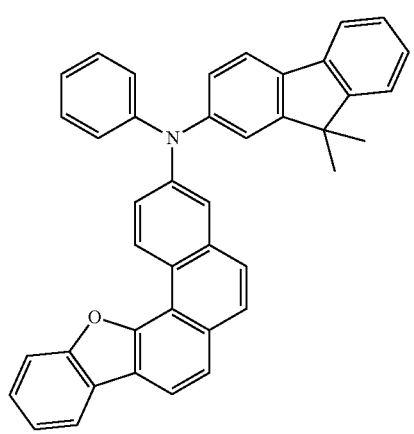
A-8
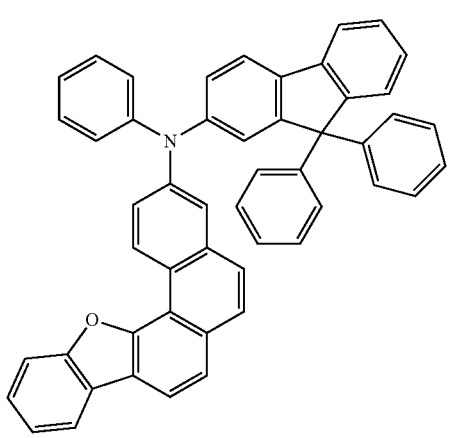

A-9
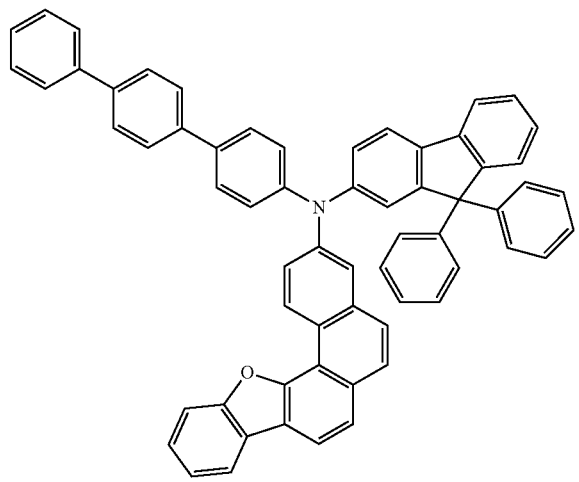
A-10
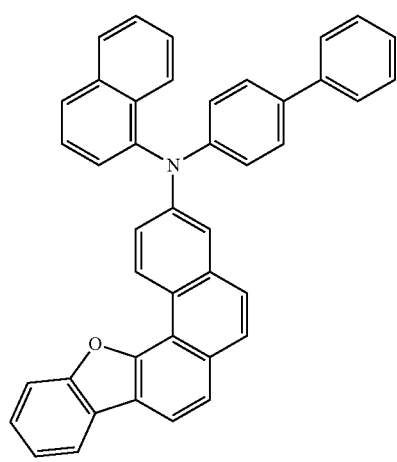
A-11
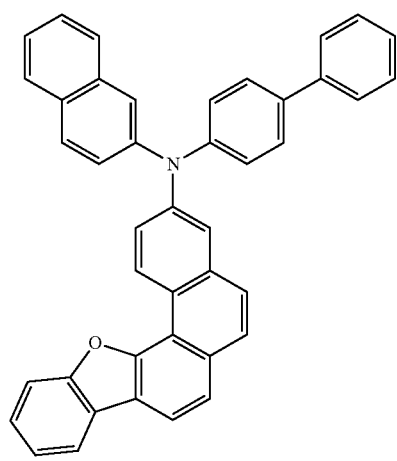
A-12
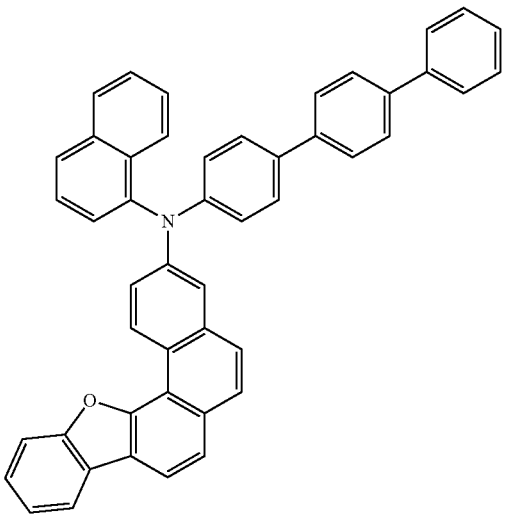
A-13
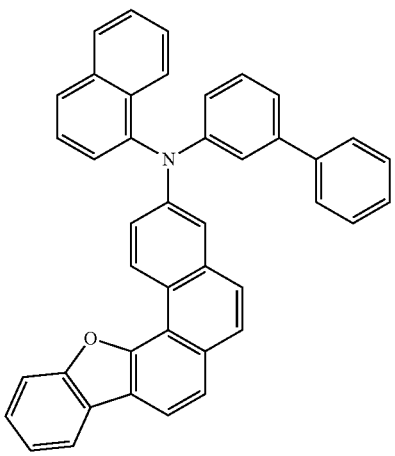
A-14
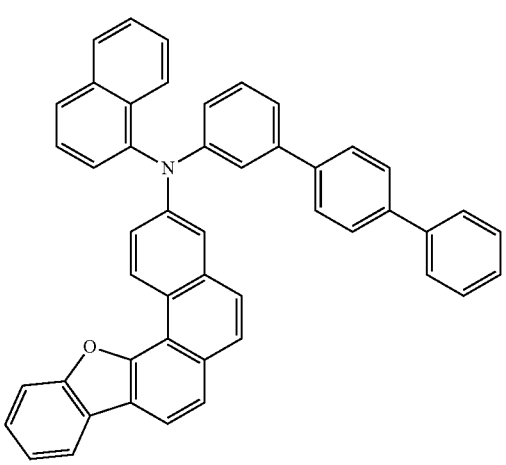

A-15
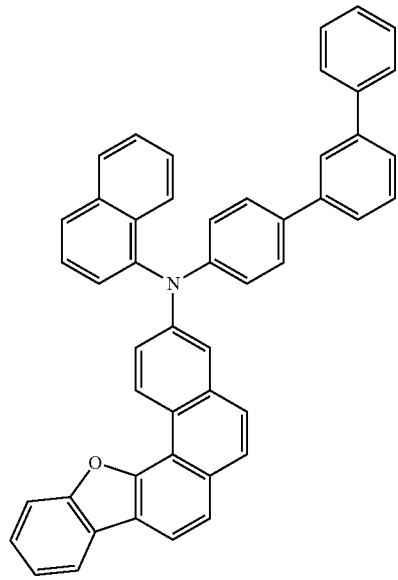
A-16
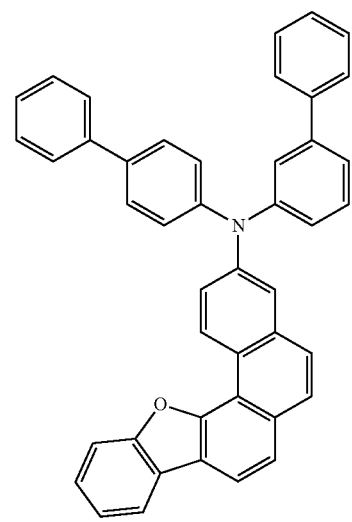
A-17
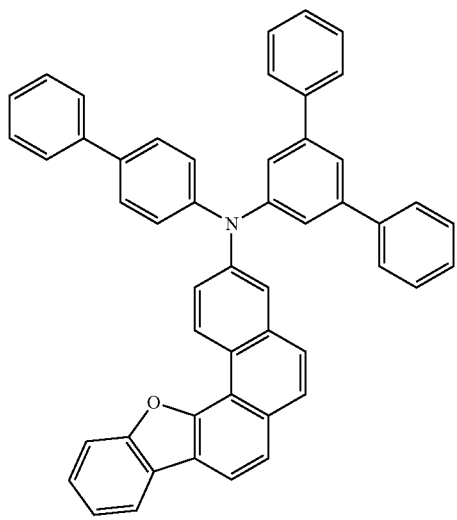
A-18
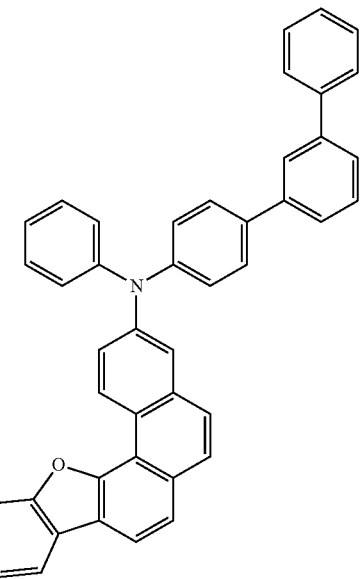
A-19
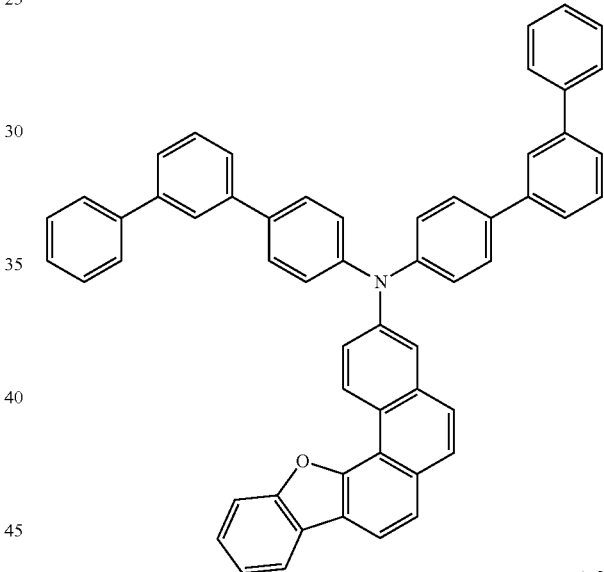
A-20
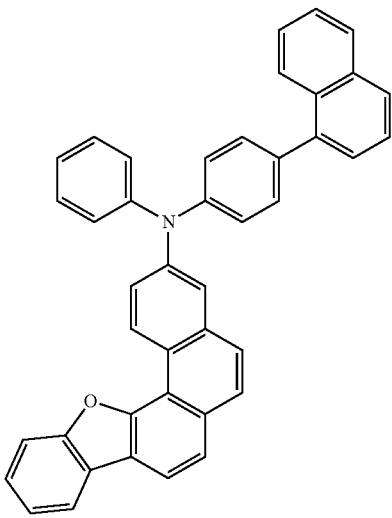

A-21
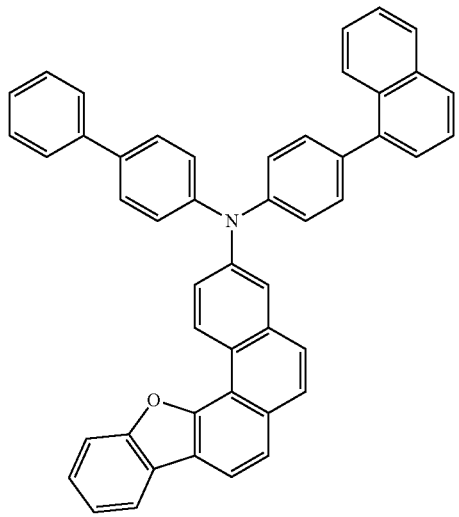
A-24
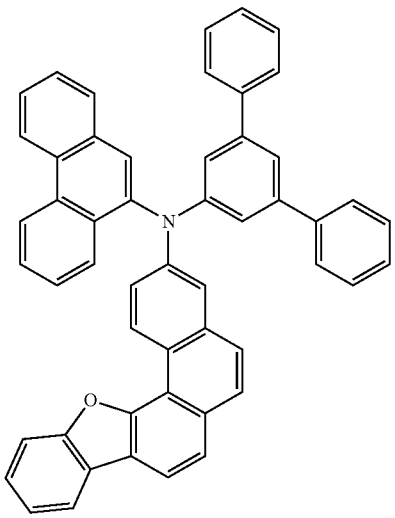
A-22
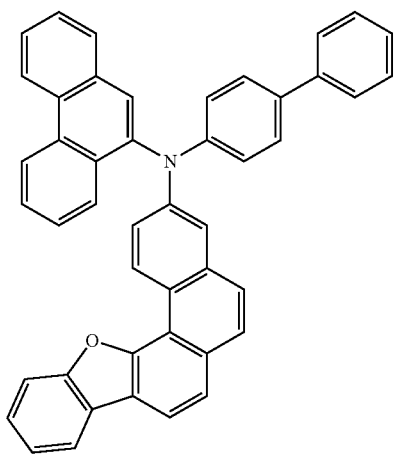
A-25
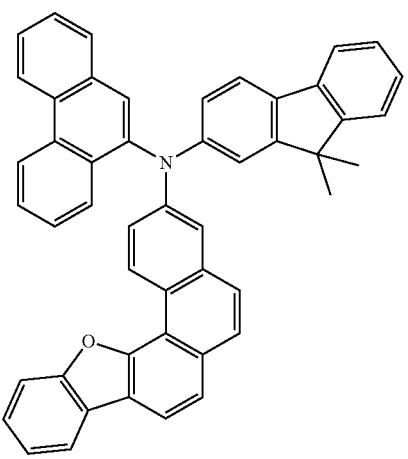
A-23
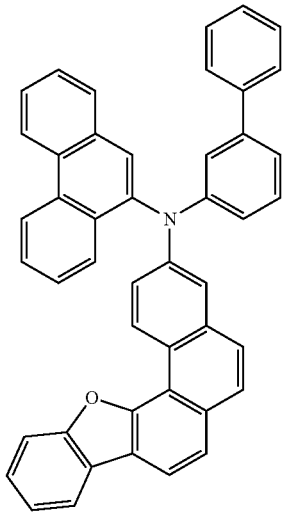
A-26
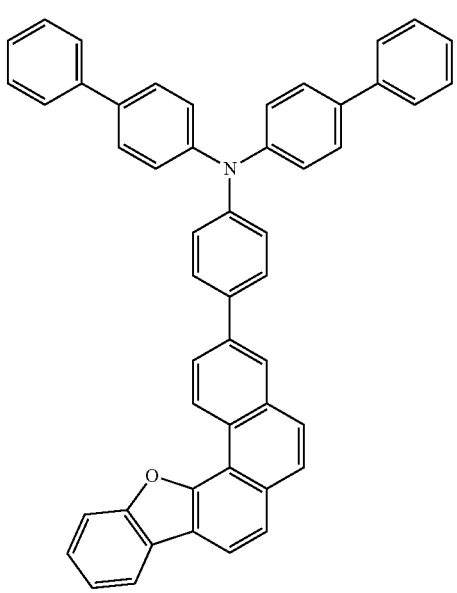

A-27
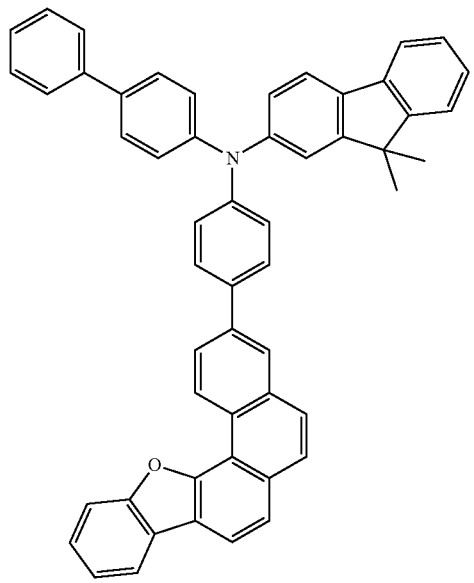
A-29
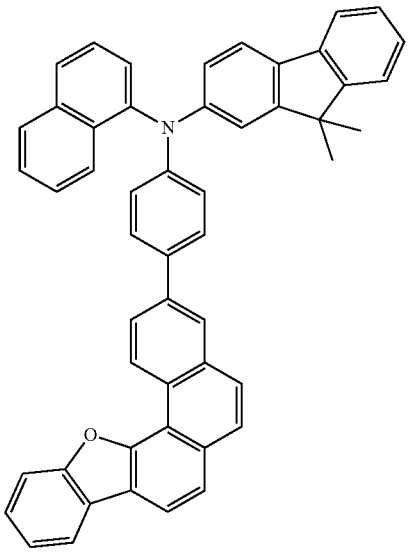
A-28
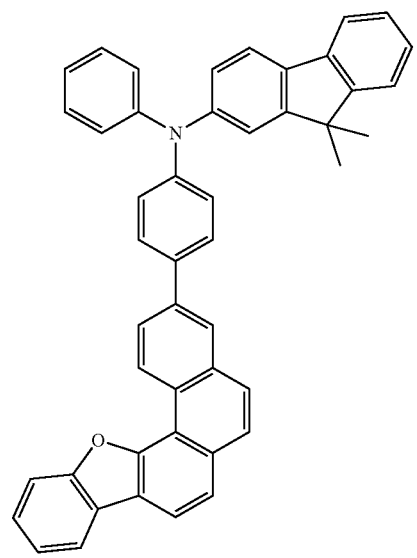
A-30
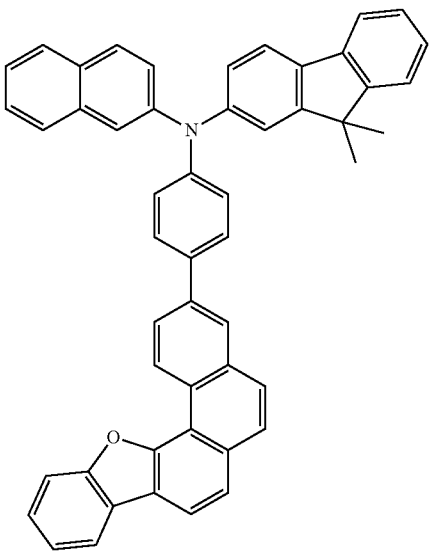

A-31
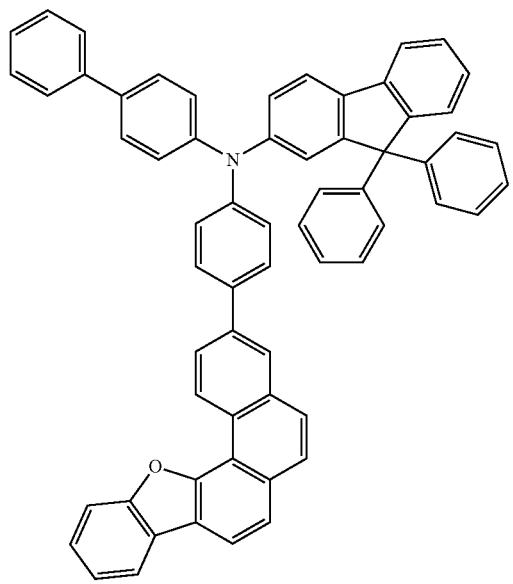
A-32
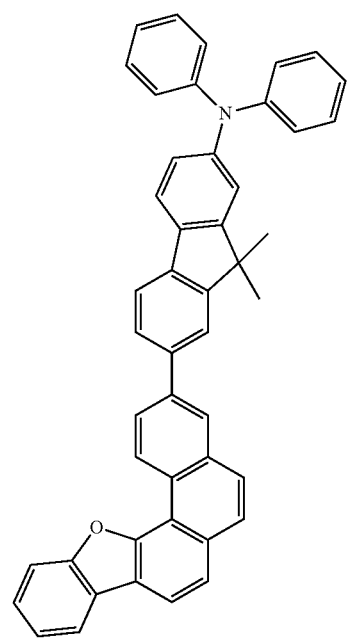
A-33
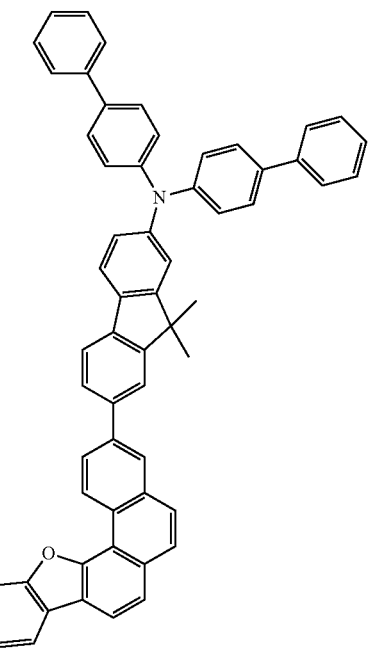
A-34
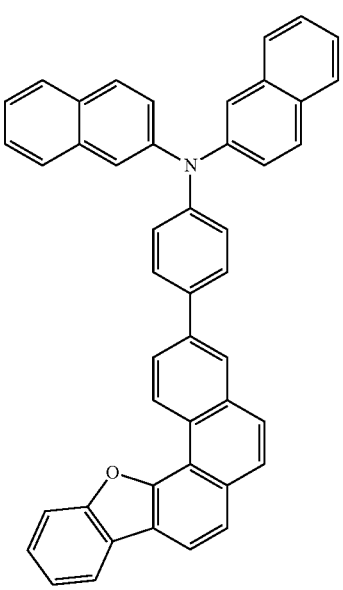

A-35
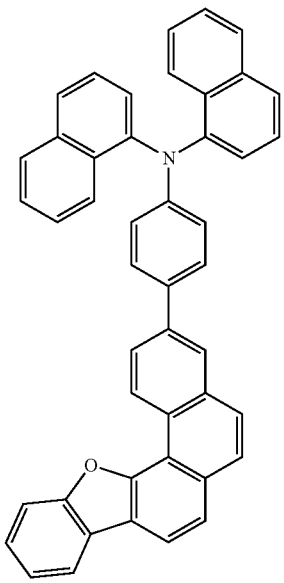
A-37
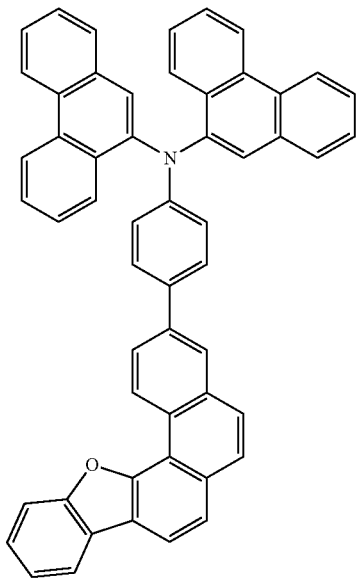
A-36
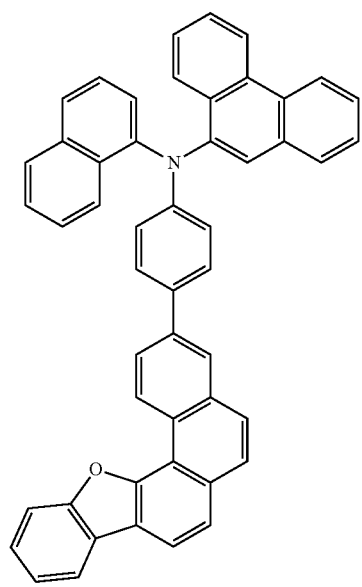
A-38
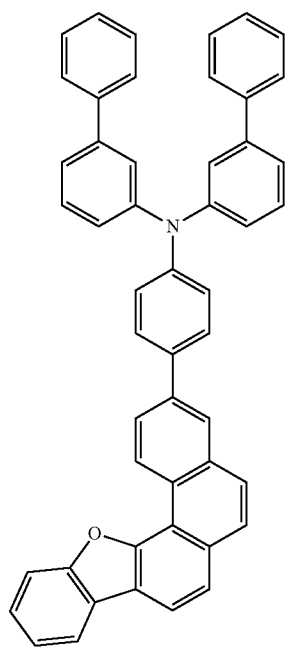

A-39
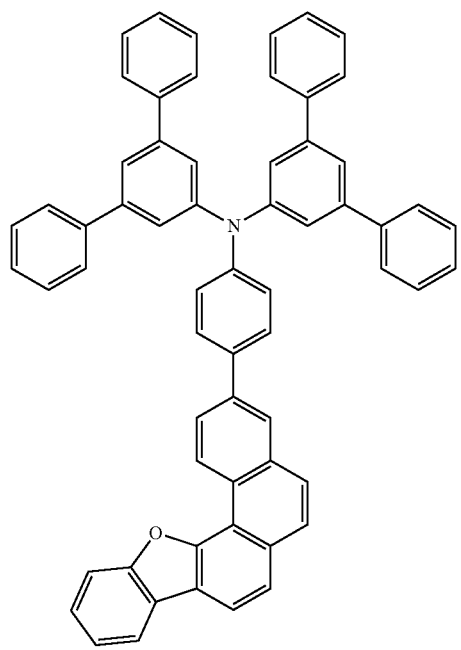
A-40
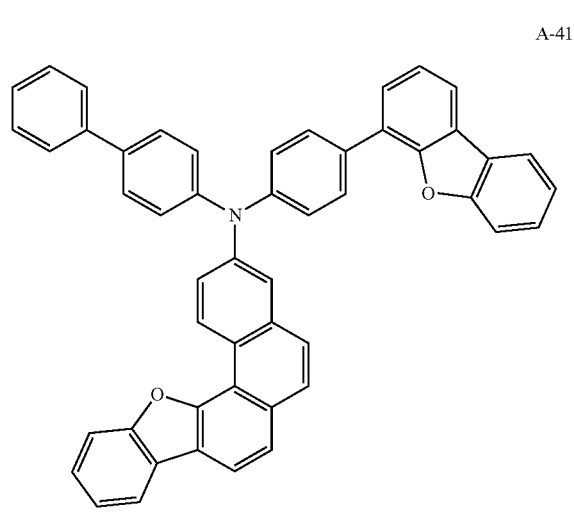
A-41
A-42
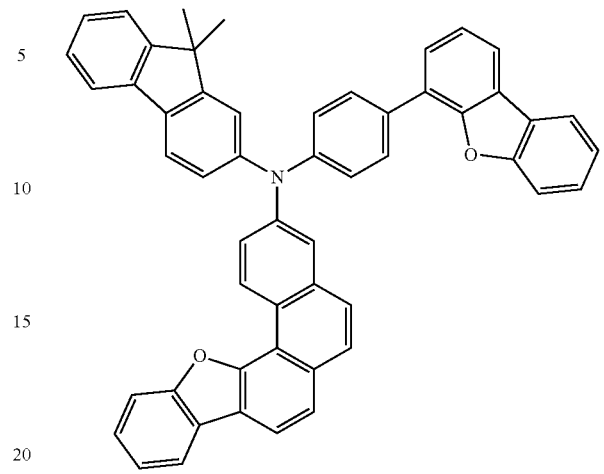
A-43
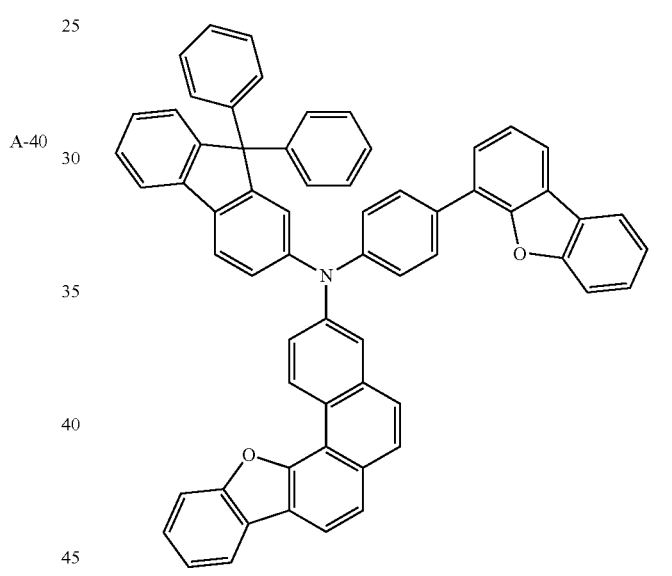
A-44

A-45
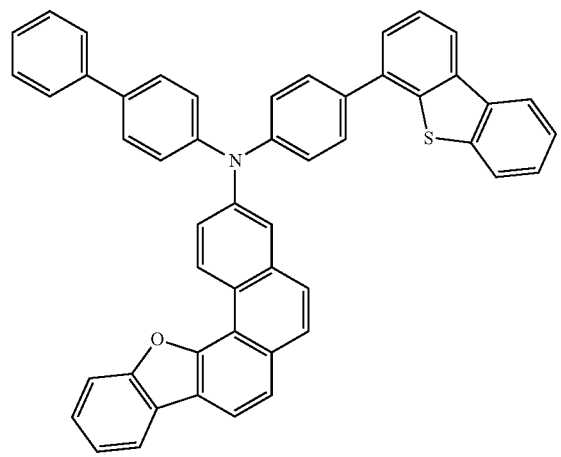
A-46
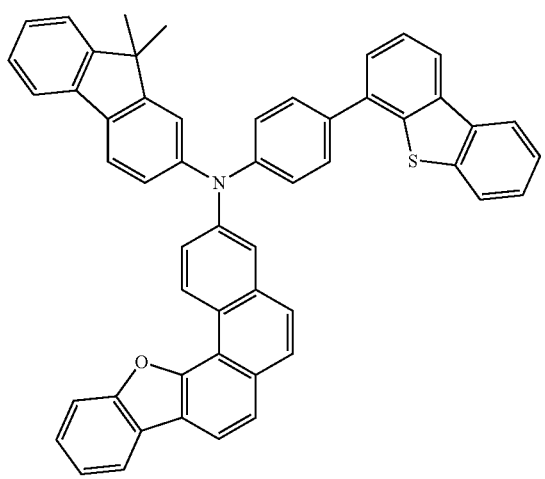
A-47
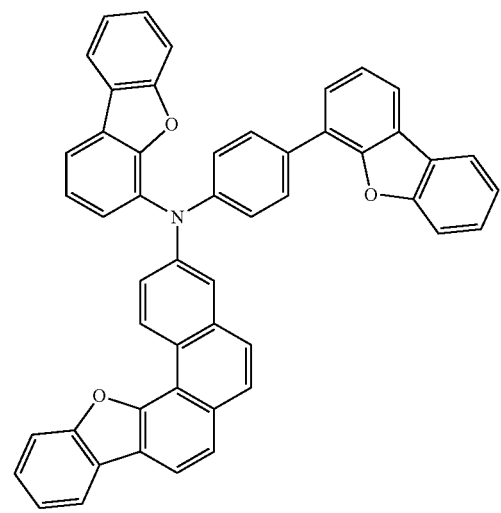
A-48
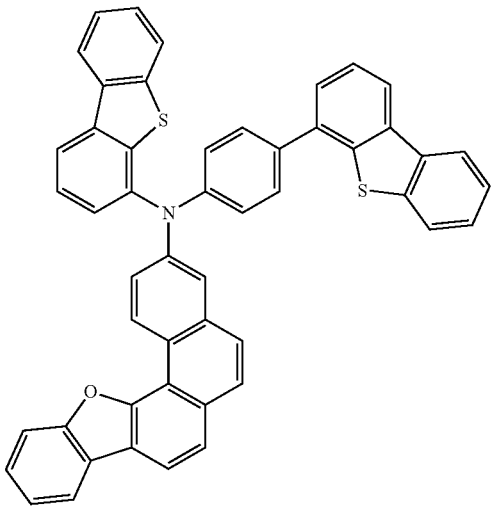
A-49
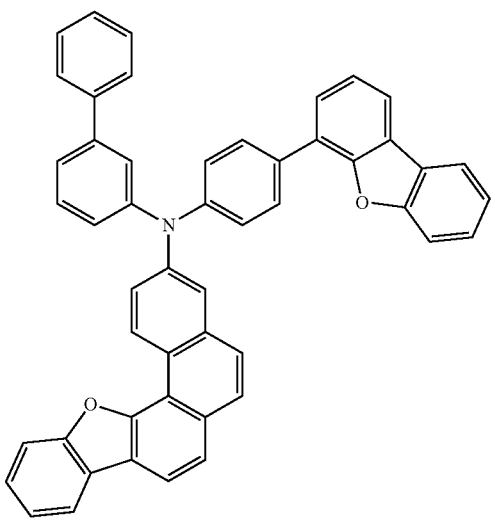
A-50
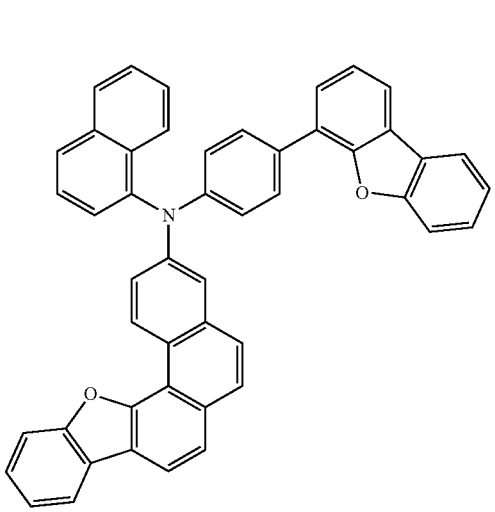

A-51
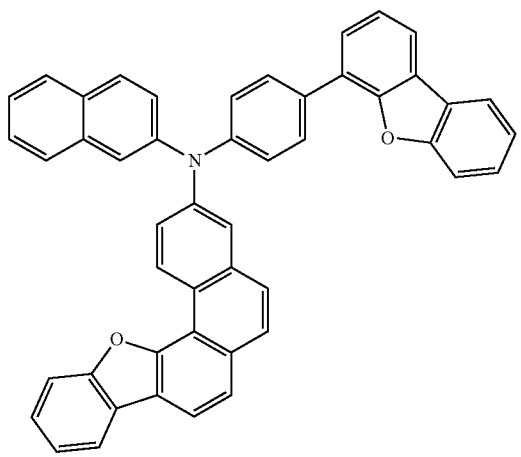
A-54
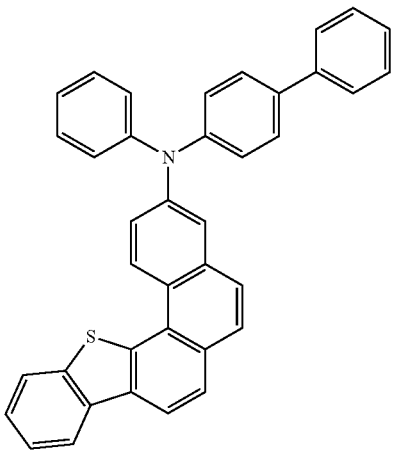
A-52
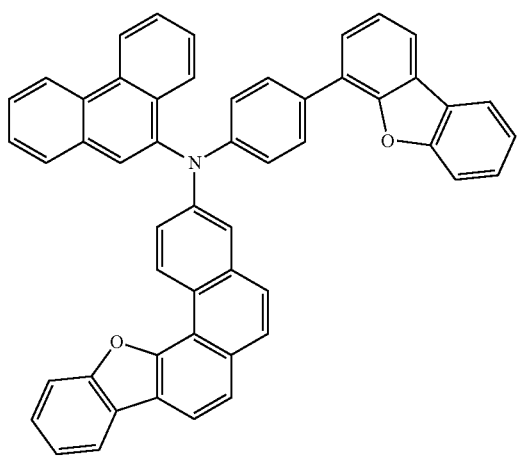
A-55
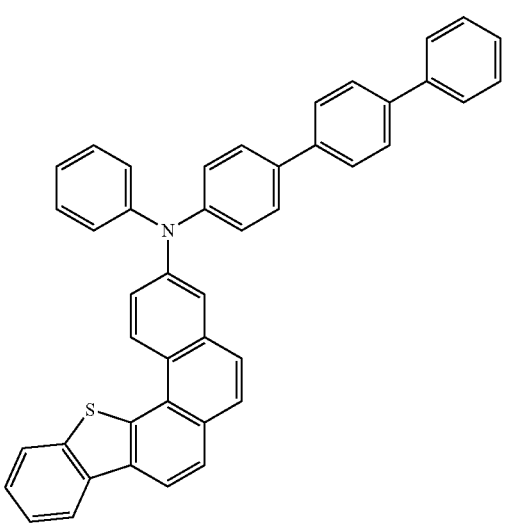
A-53
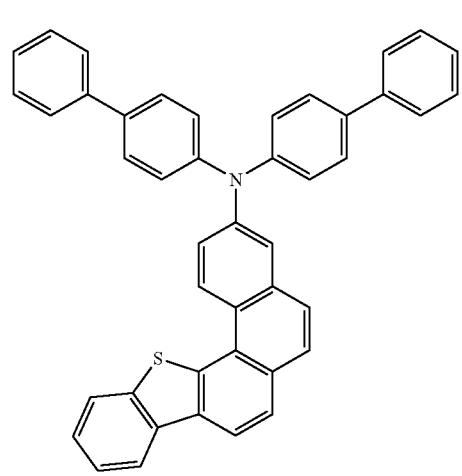
A-56
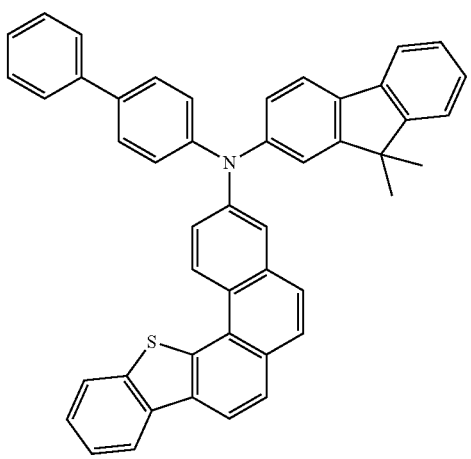

-continued
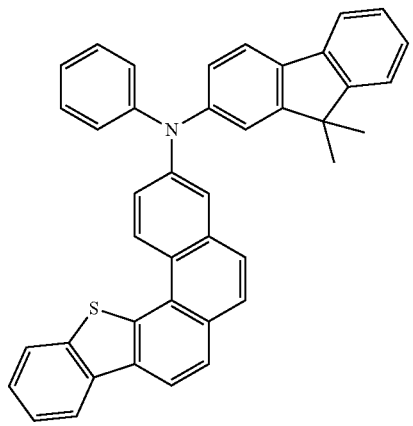
A-57
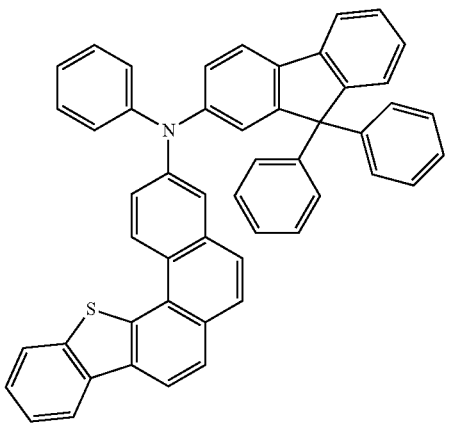
A-60
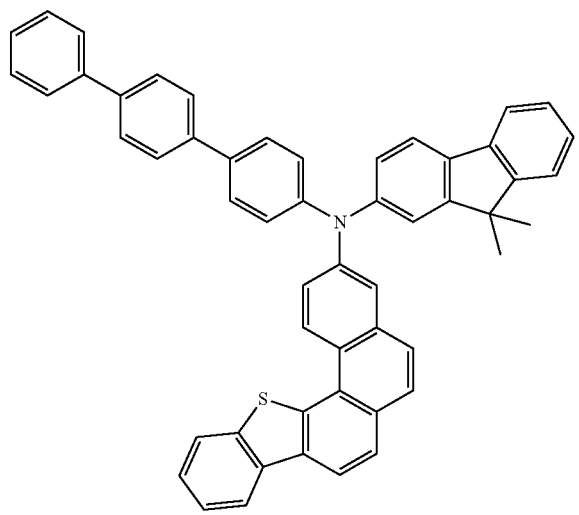
A-58
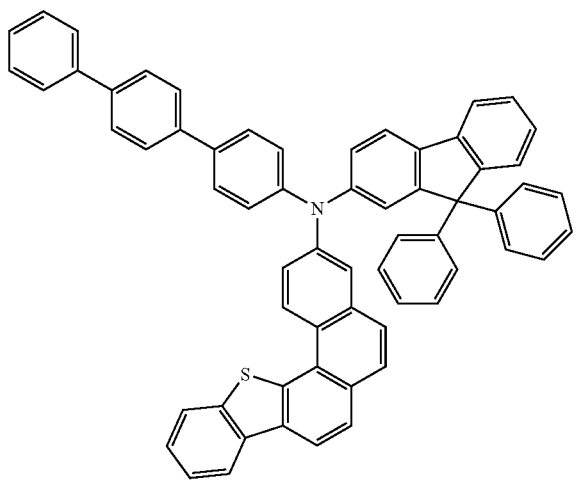
A-61
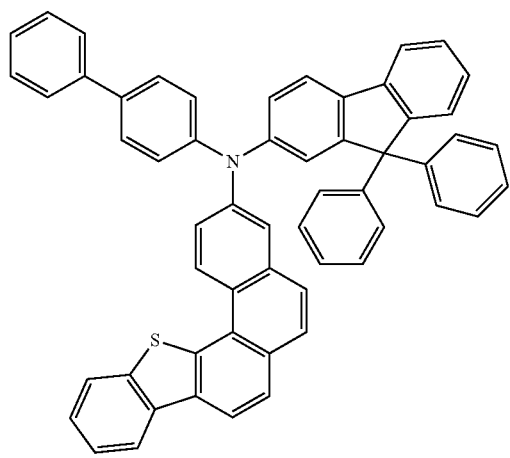
A-59
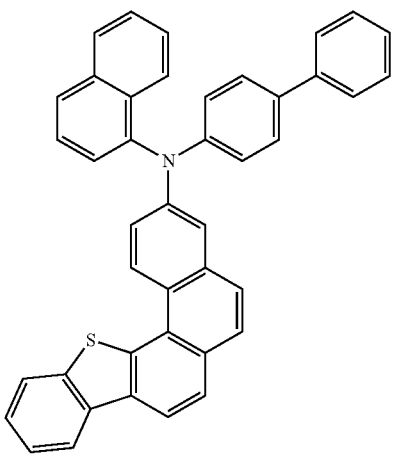
A-62

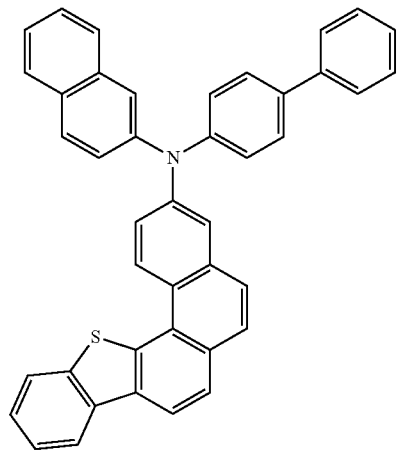
A-63
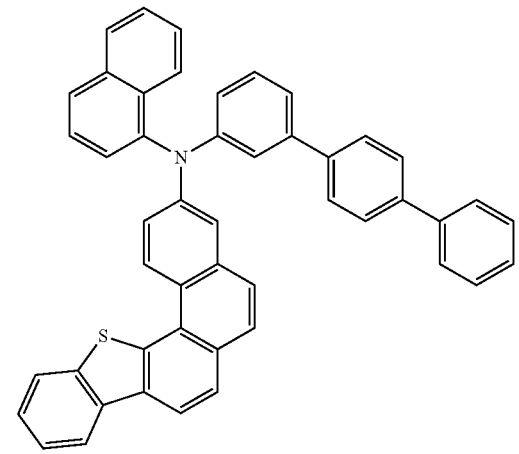
A-66
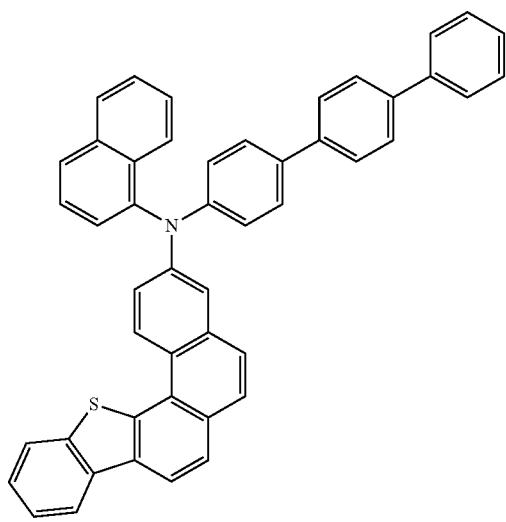
A-64
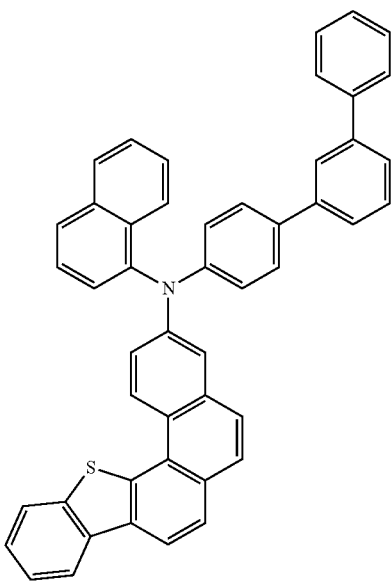
A-67
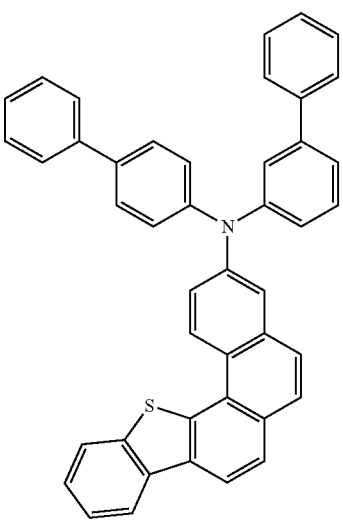
A-68
A-65

A-69
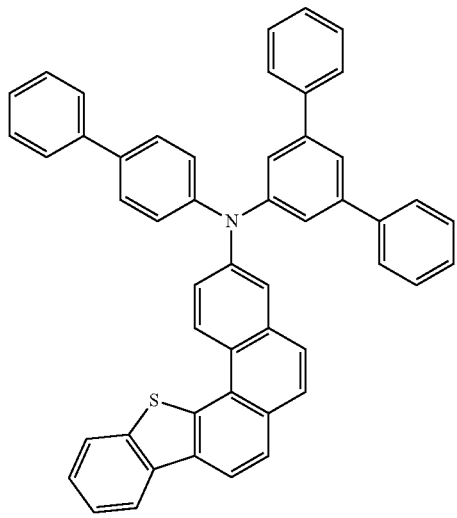
A-70
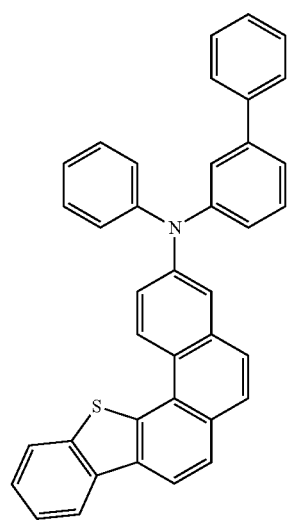
A-71
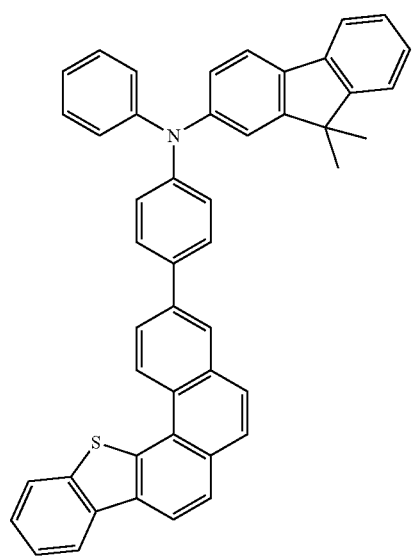
A-72
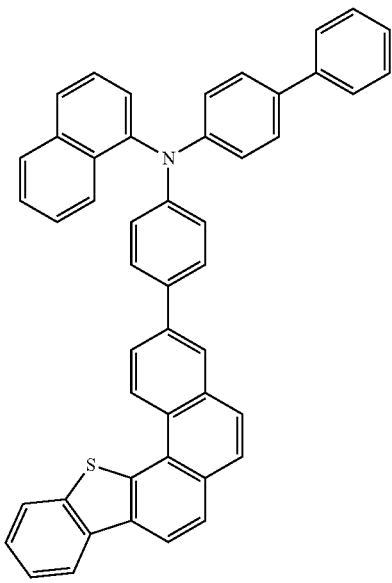
A-73
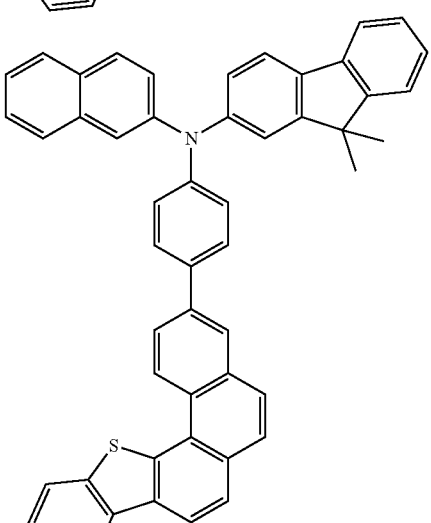
A-74
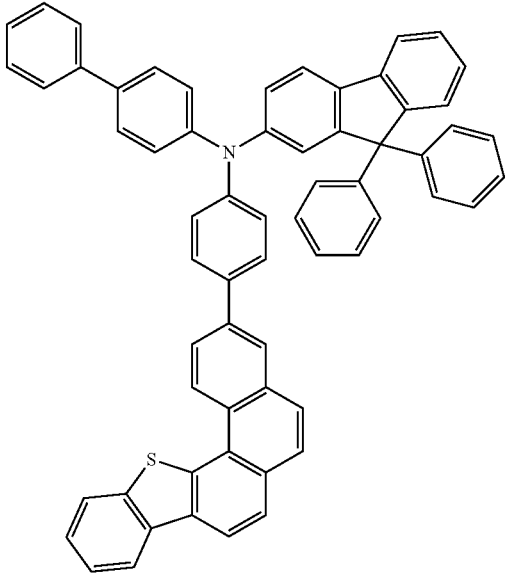

A-75
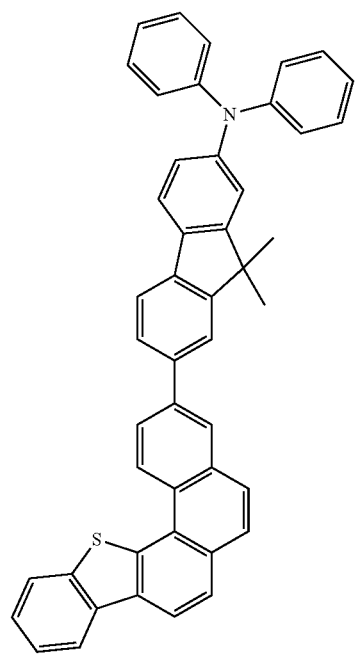
A-76
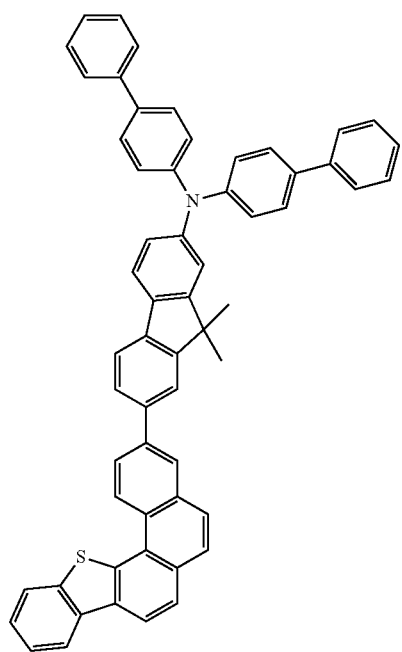
A-77
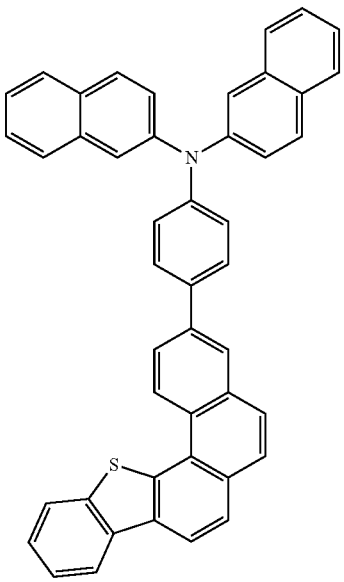
A-78
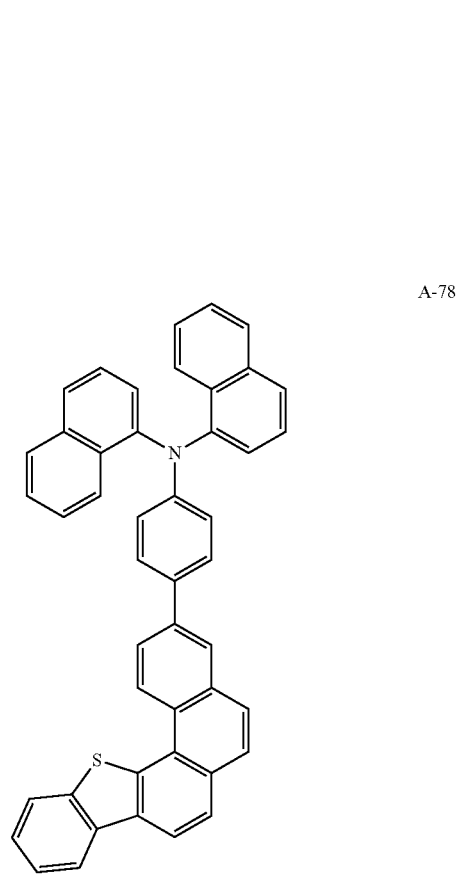

A-79
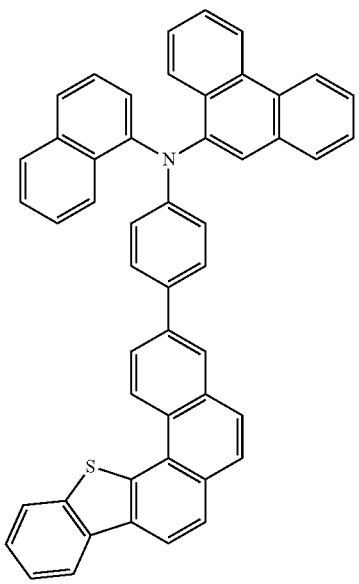
A-80
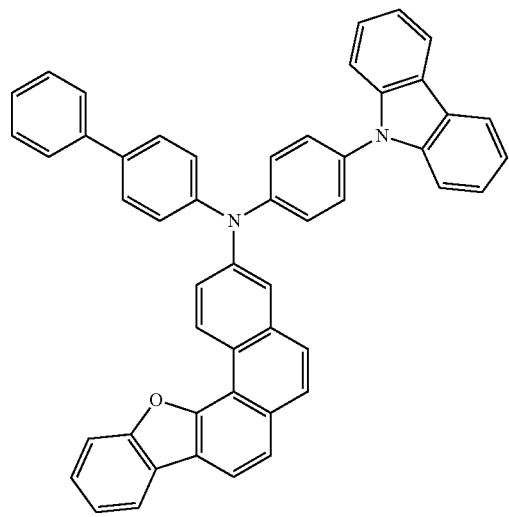
A-81
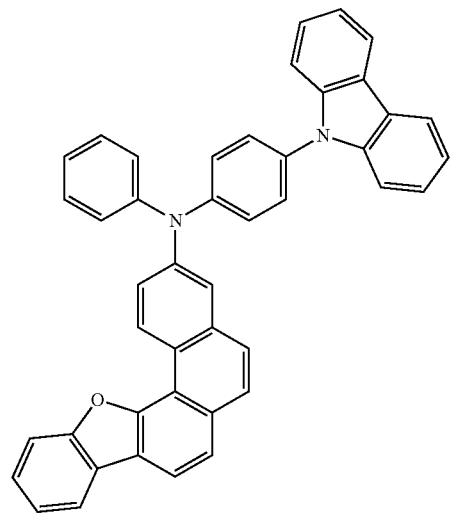
A-82
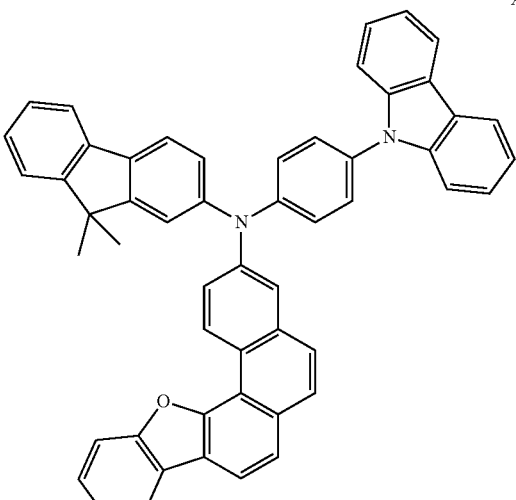
A-83
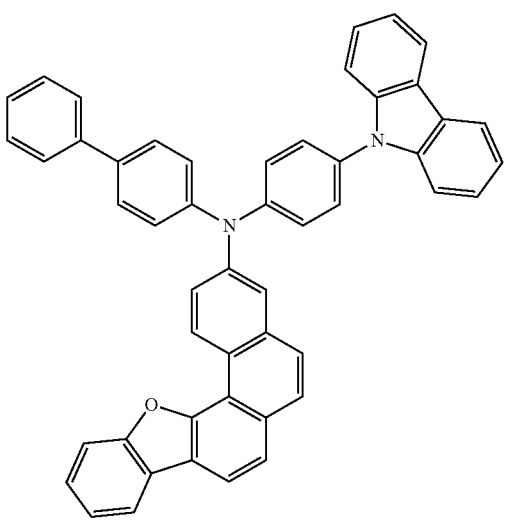
A-84
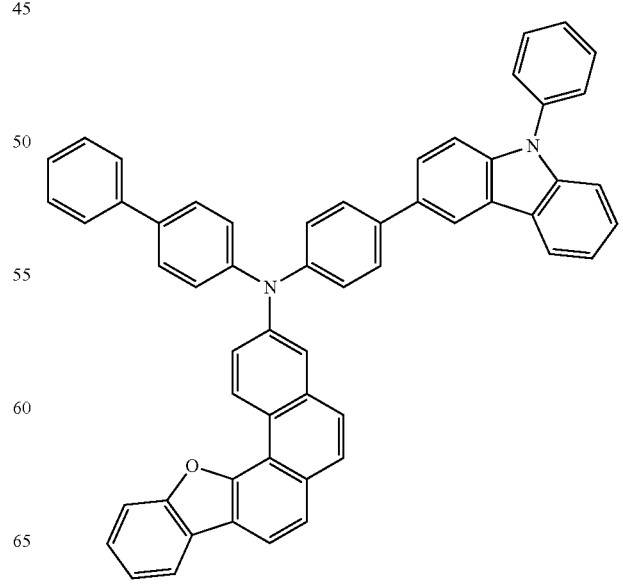

A-85
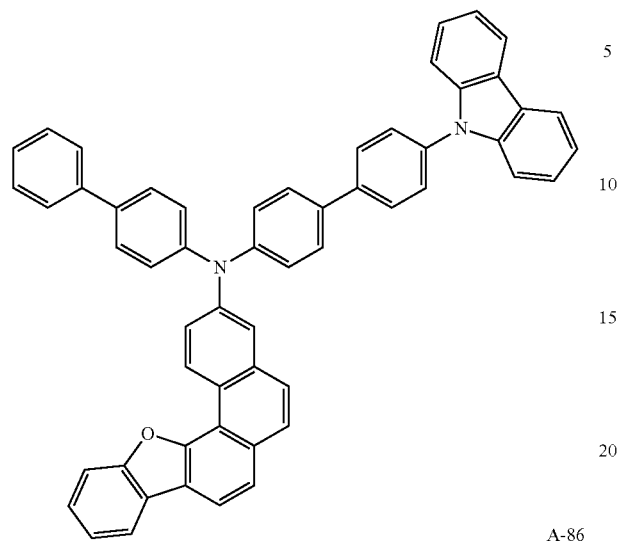
A-86
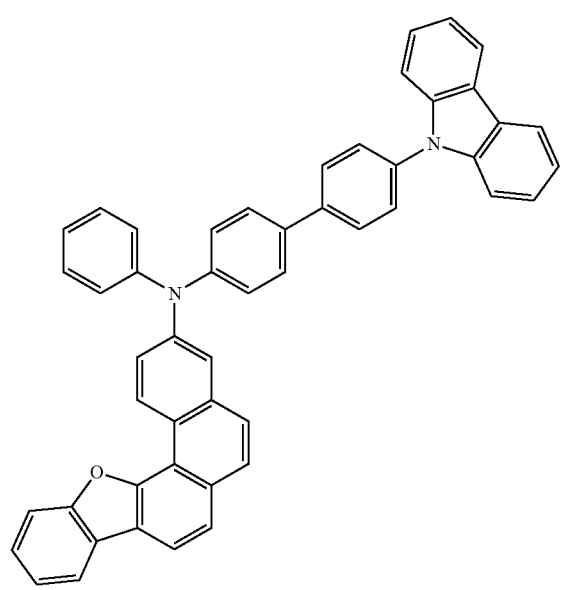
A-87
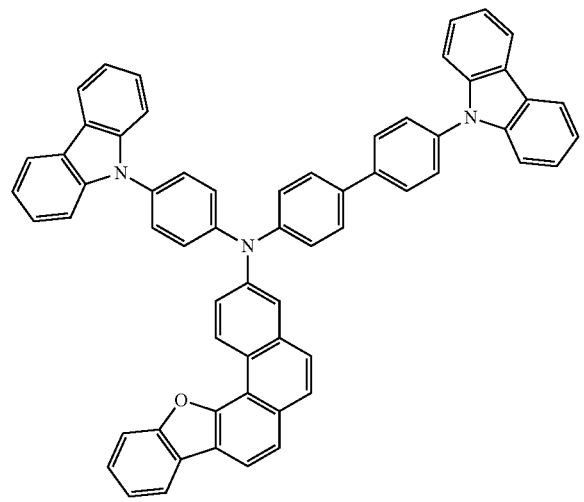
A-88
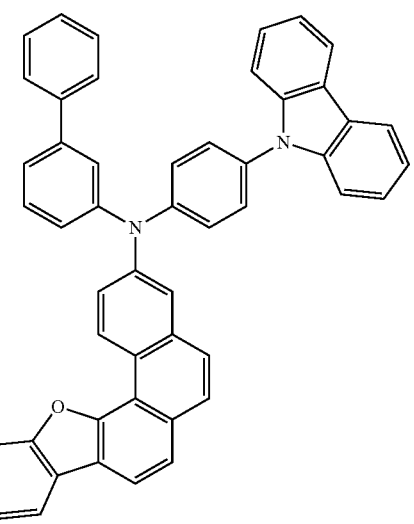
A-89
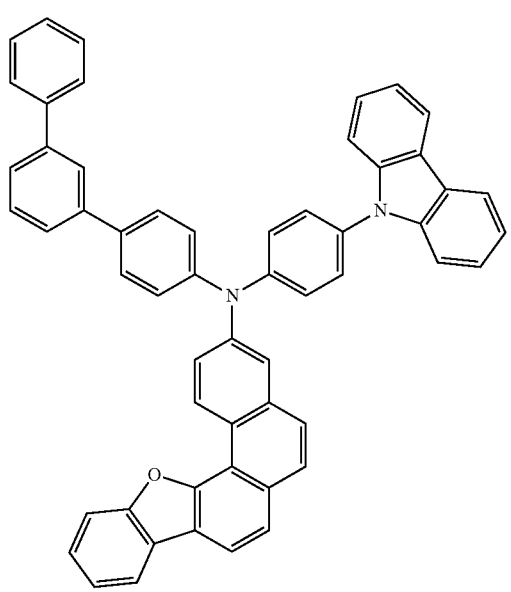
A-90
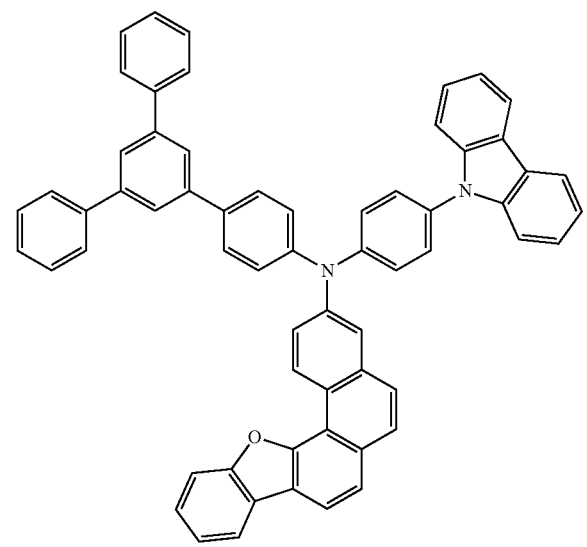

A-91
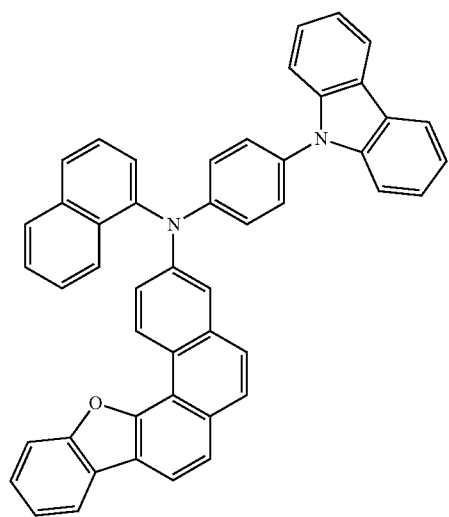
A-94
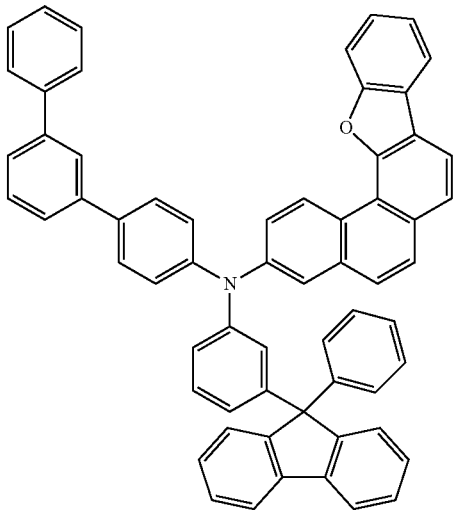
A-92
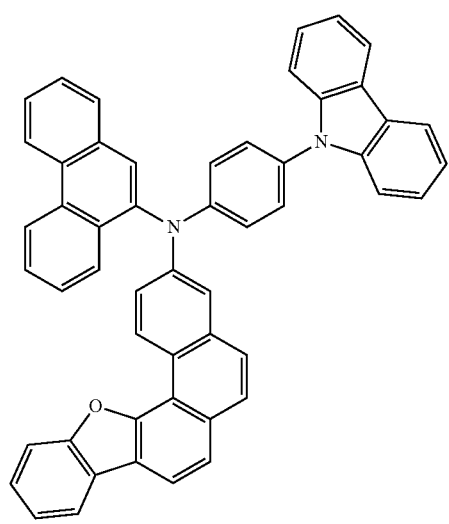
A-95
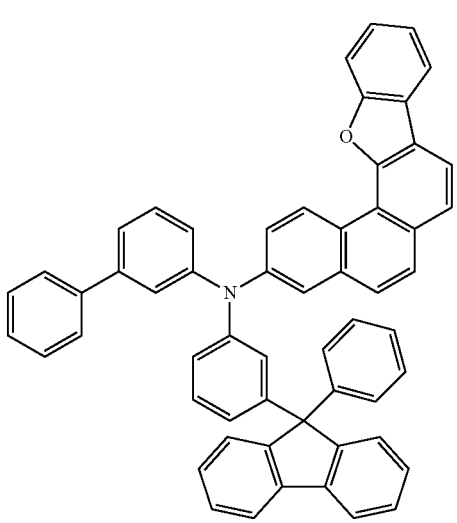
A-93
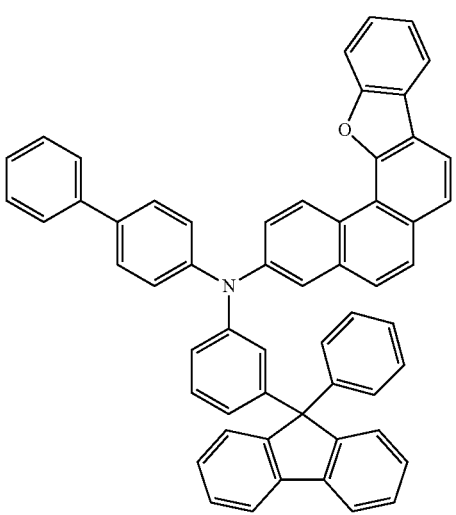
A-96
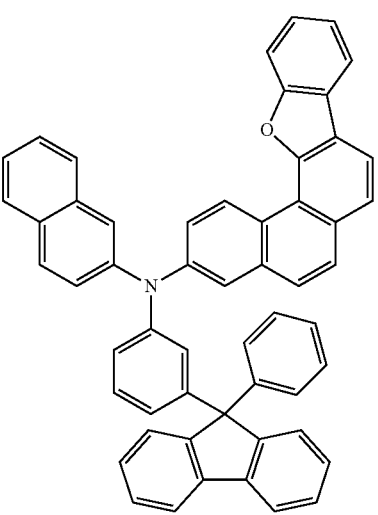

-continued
A-97
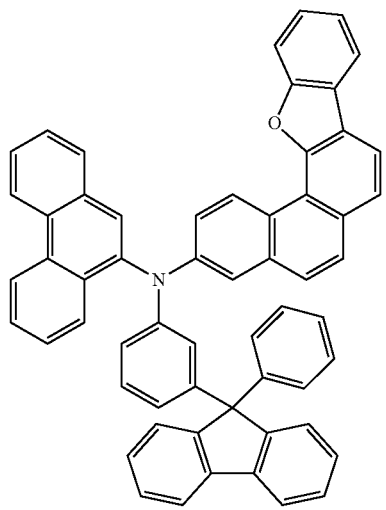
A-98
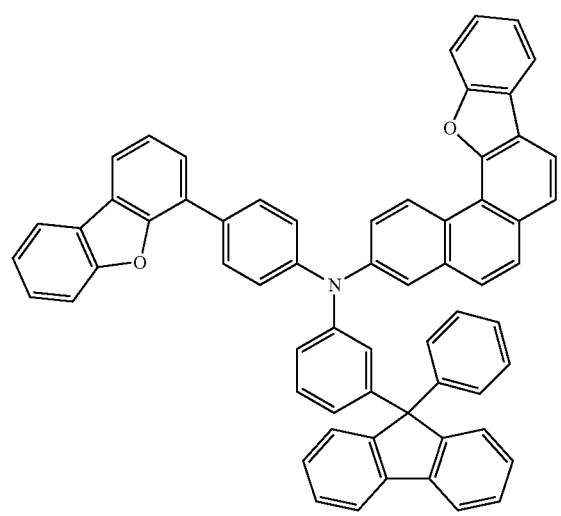
A-99
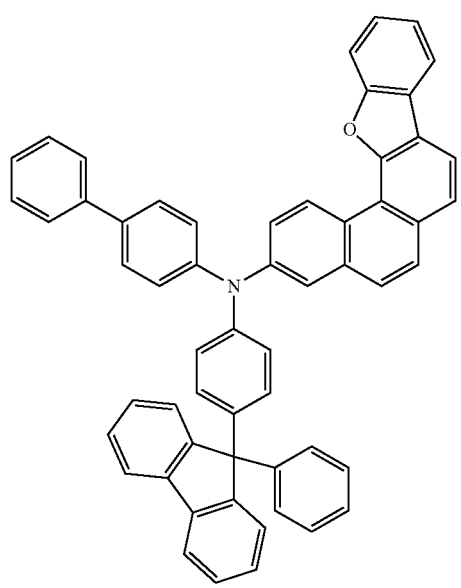
-continued
A-100
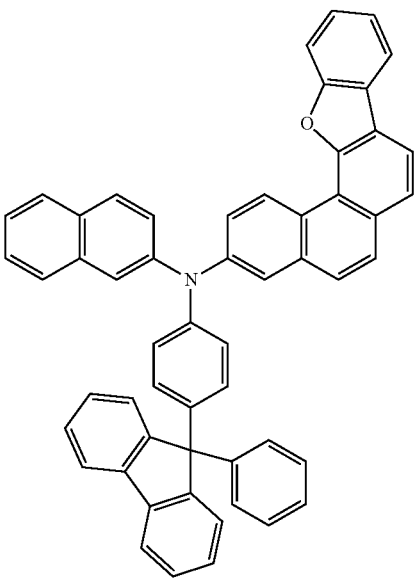
A-101
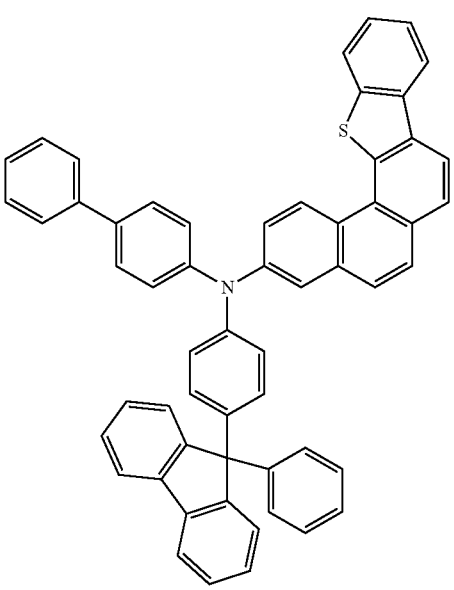
A-102
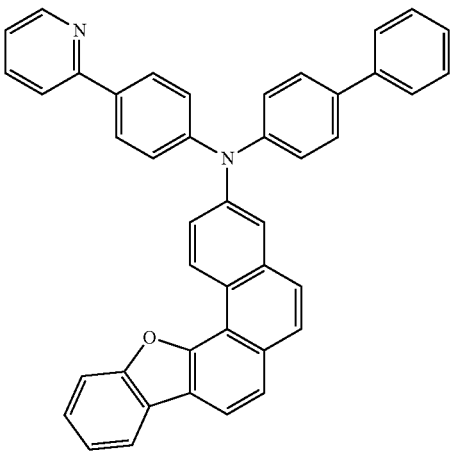

A-103
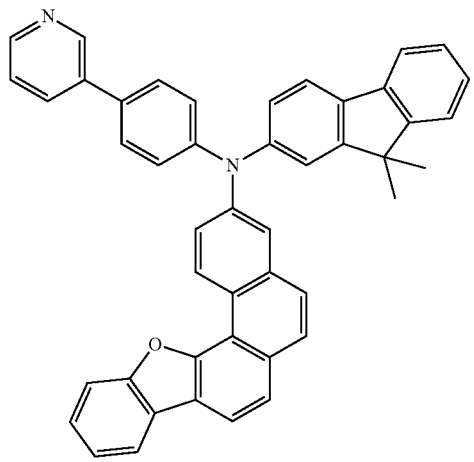
A-104
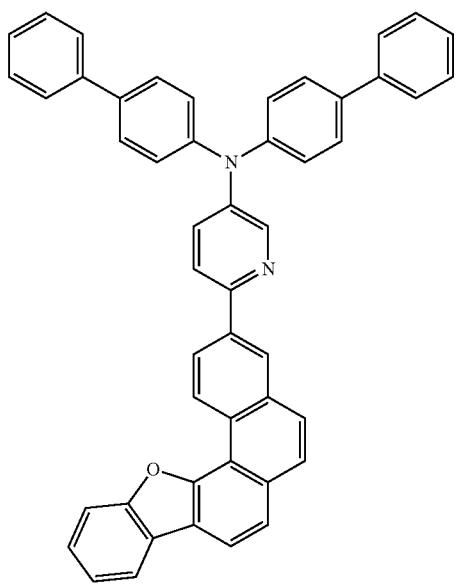
A-105
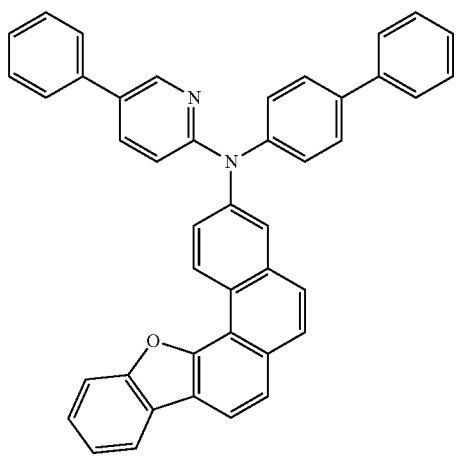
A-106
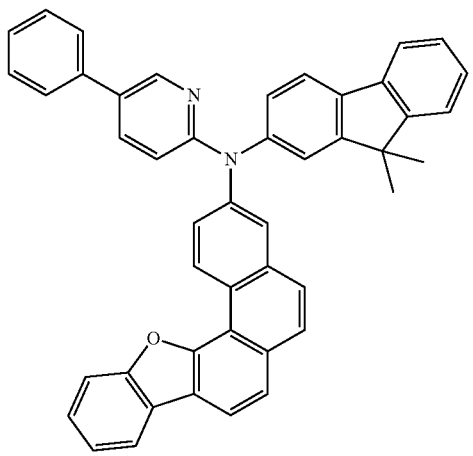
A-107
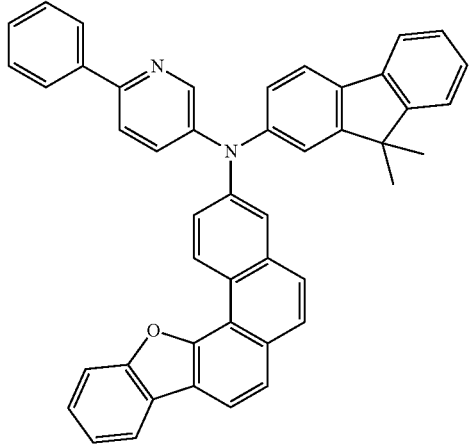
A-108
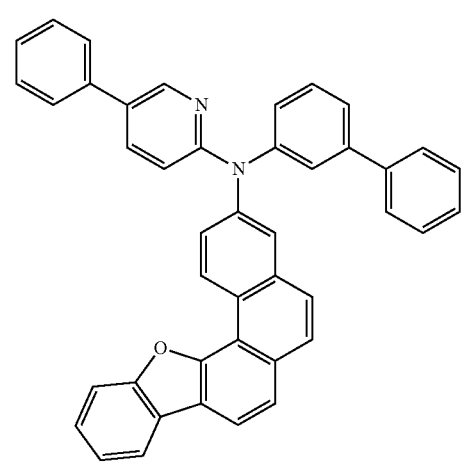

A-109
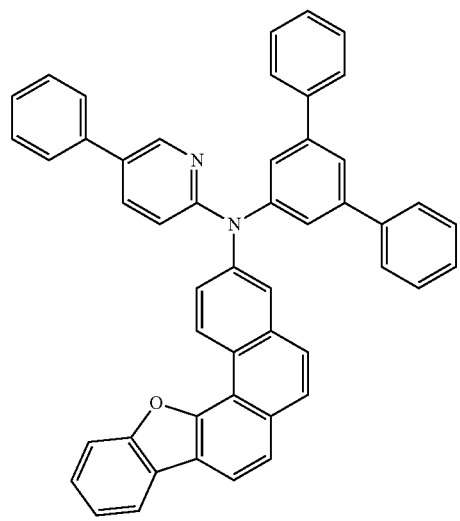
A-110
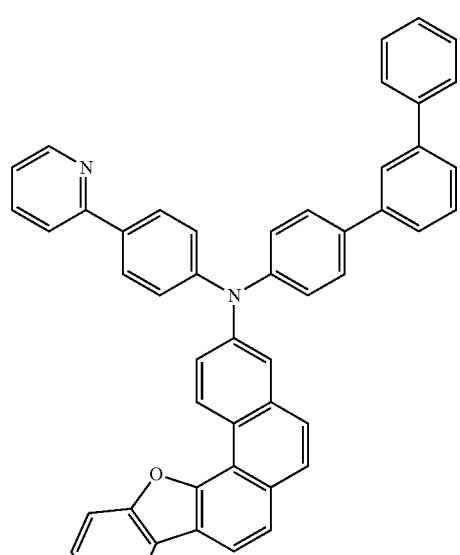
A-111
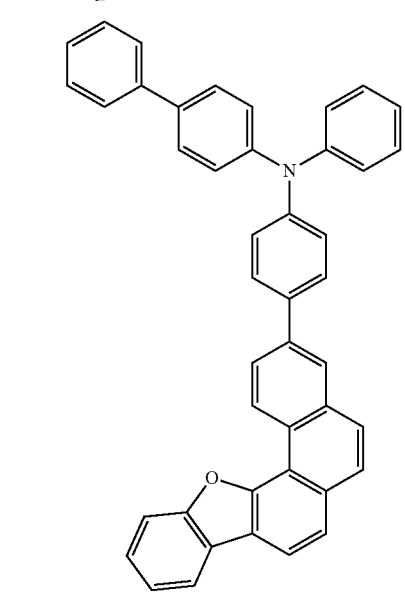
A-112
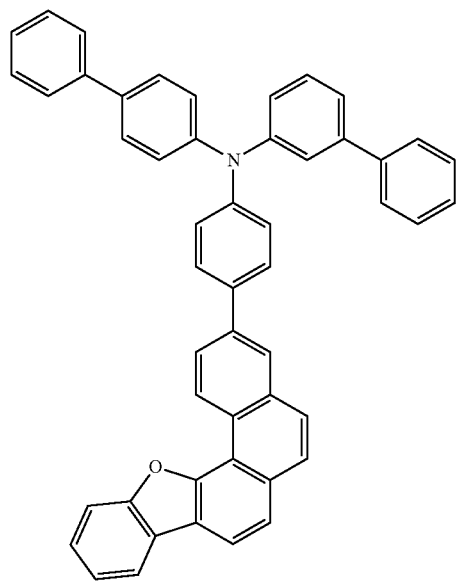
B-1
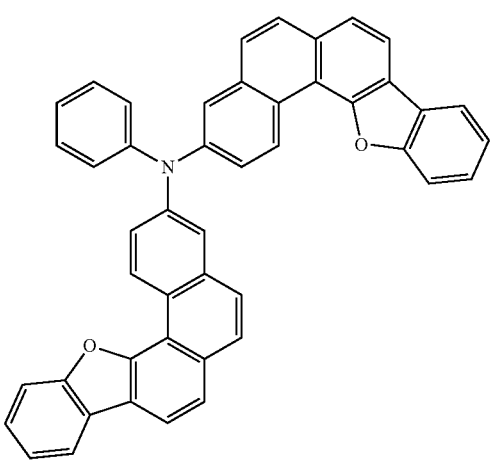
B-2
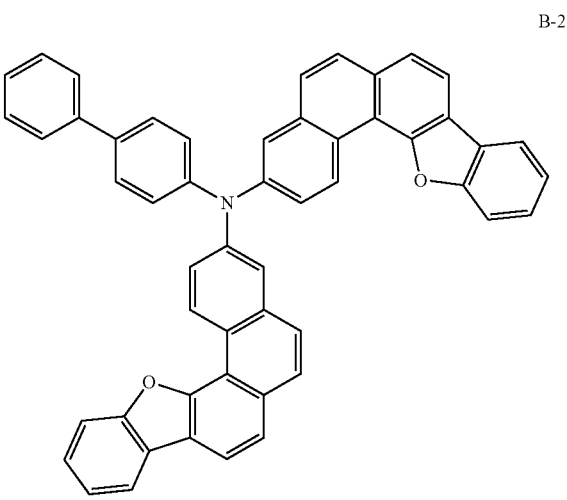

B-3
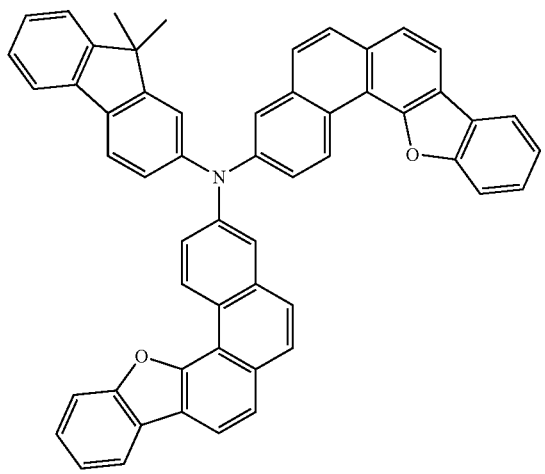
B-4
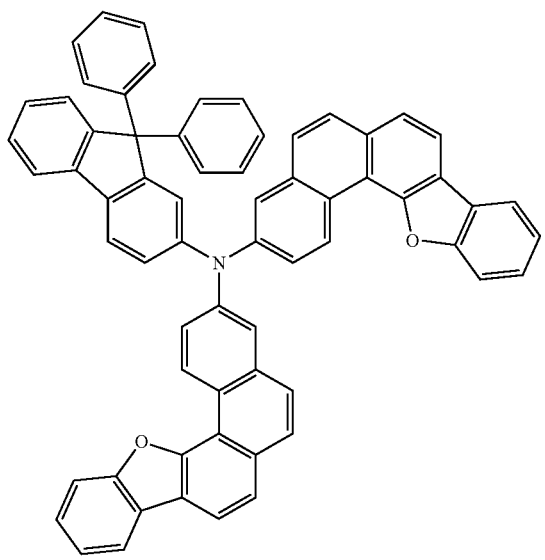
B-5
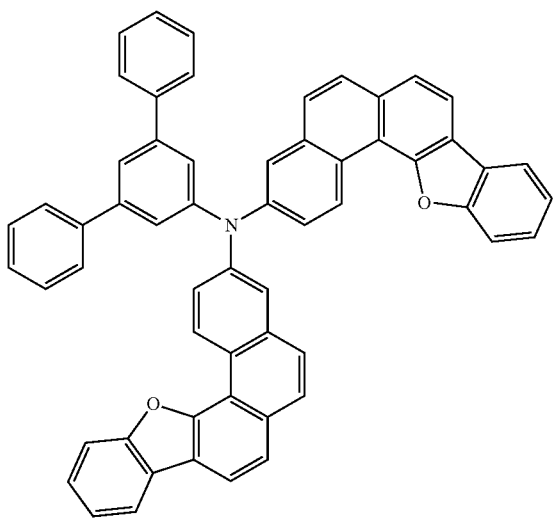
B-6
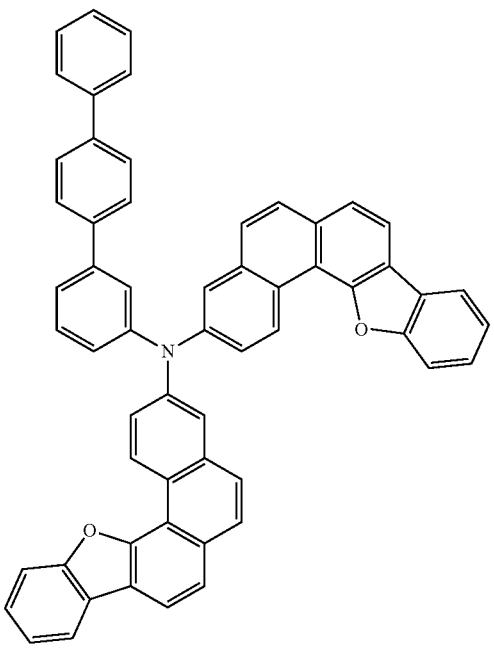
B-7
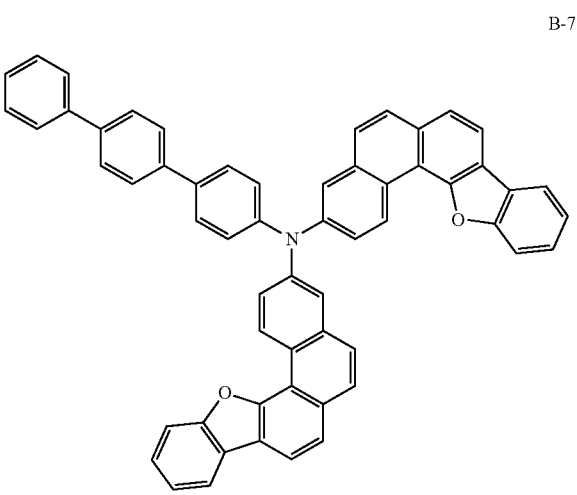
B-8
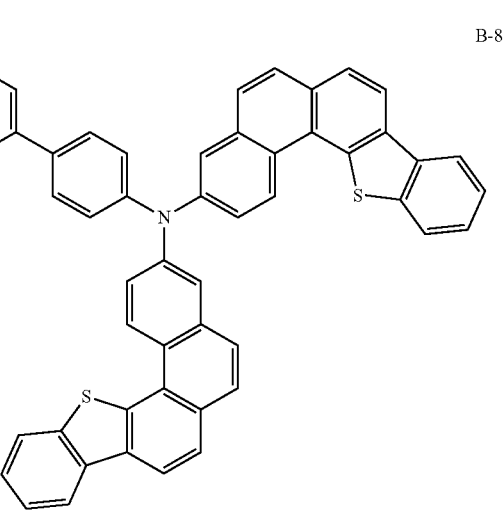

B-9
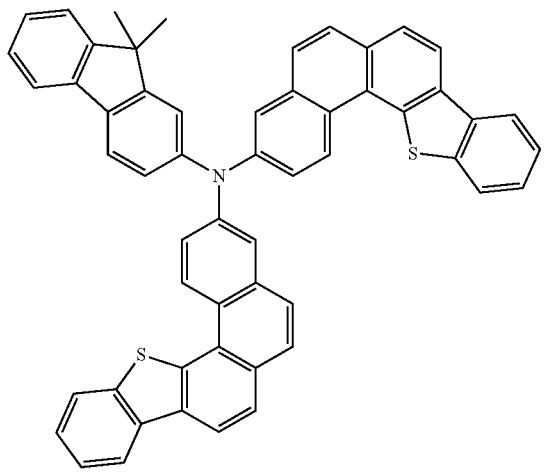
B-12
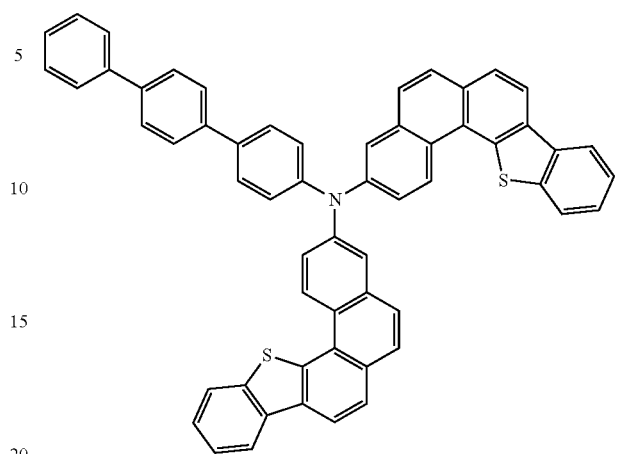
B-10
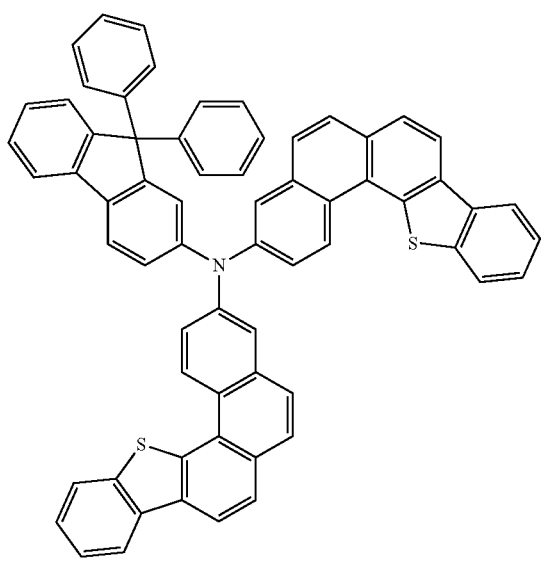
B-13
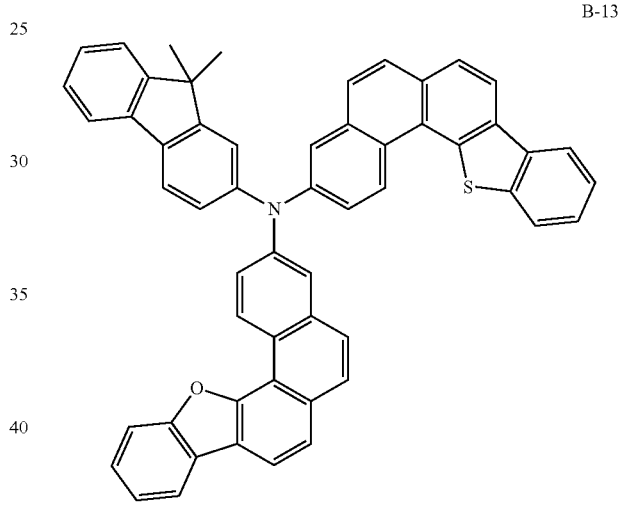
B-11
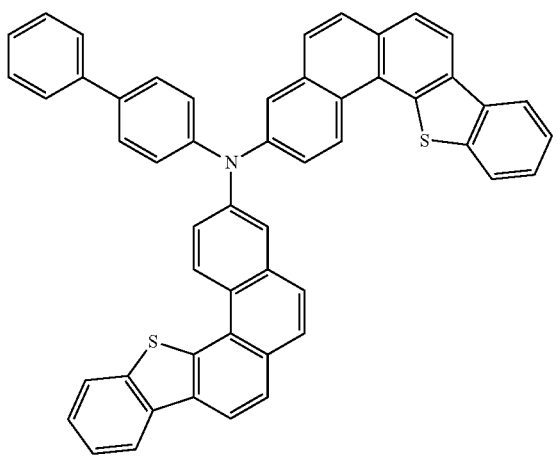
B-14
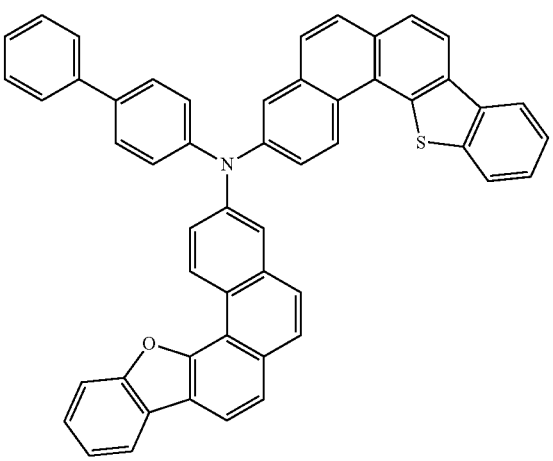

-continued
B-15
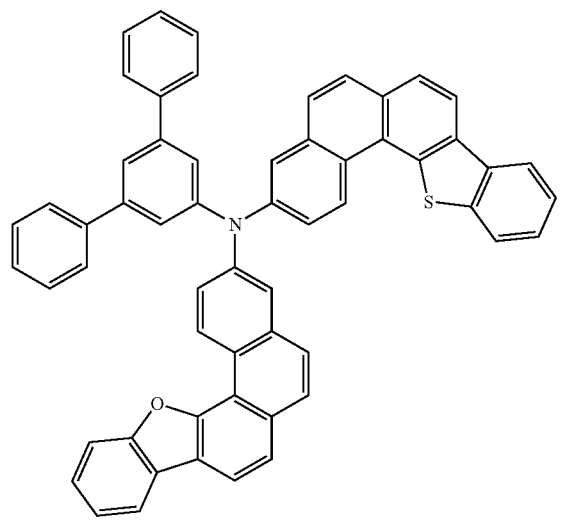
B-16
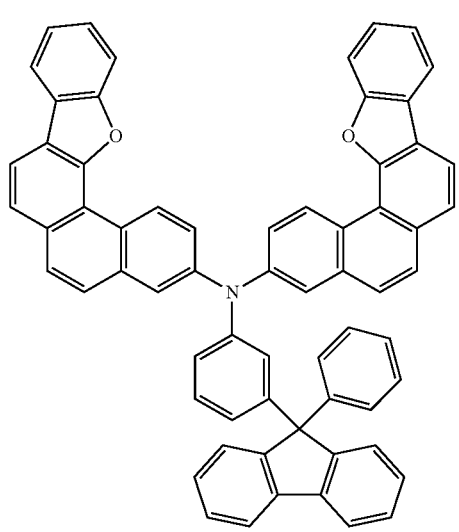
B-17
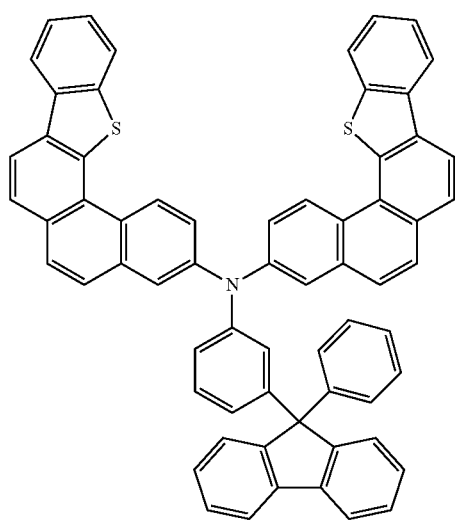
-continued
B-18
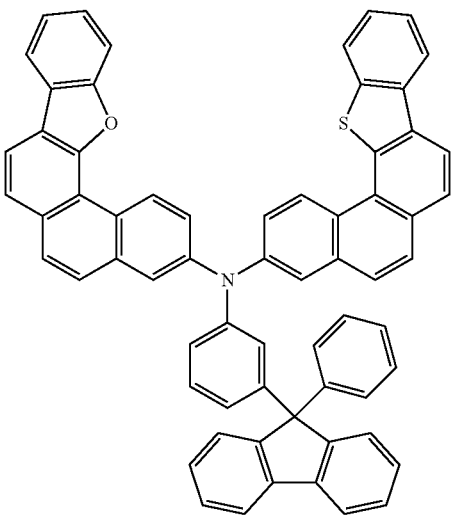
B-19
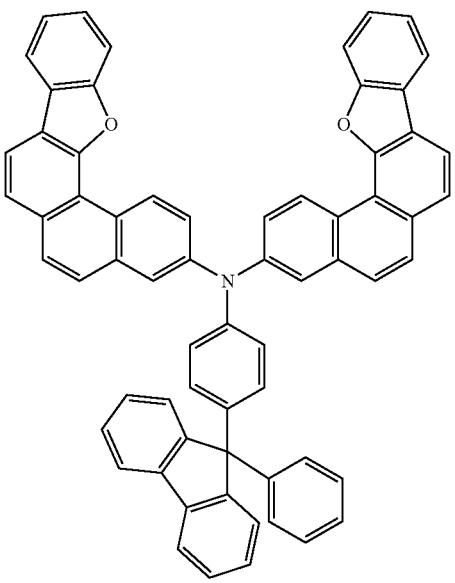
B-20
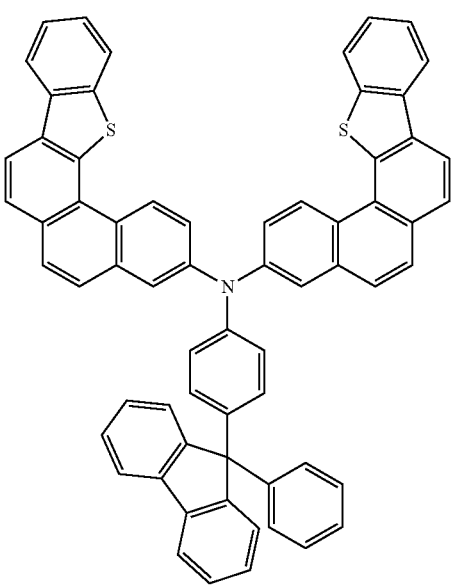

B-21
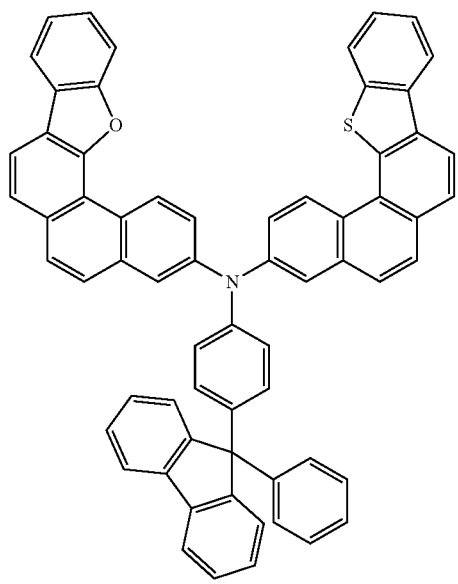
B-22
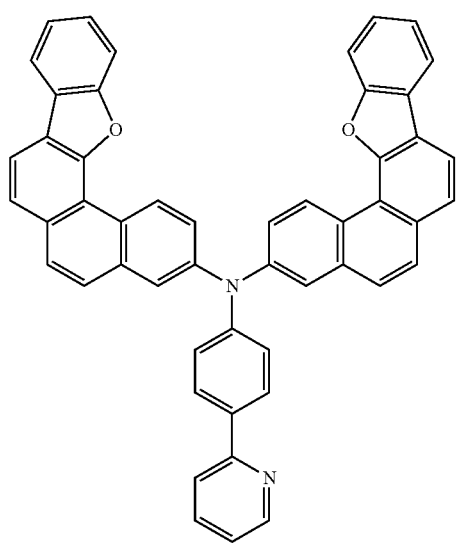
B-23
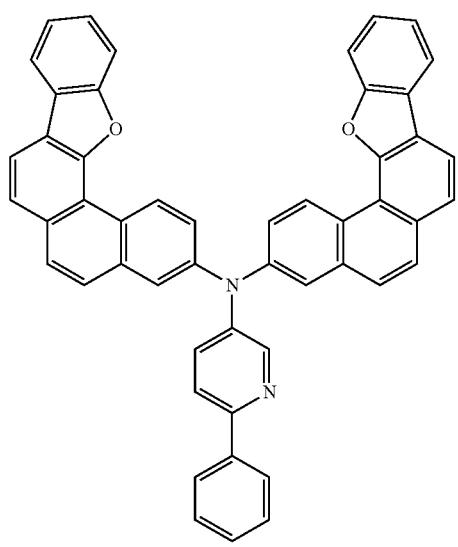
B-24
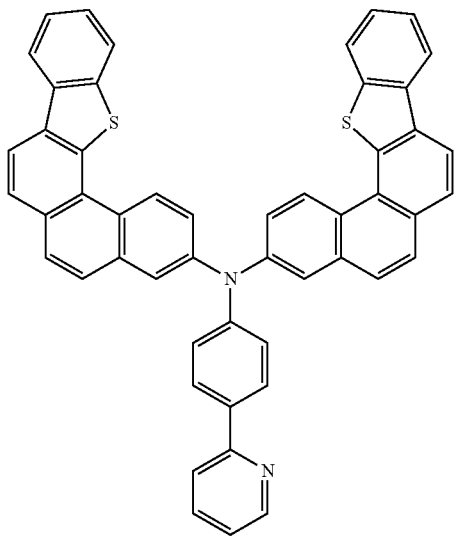
C-1
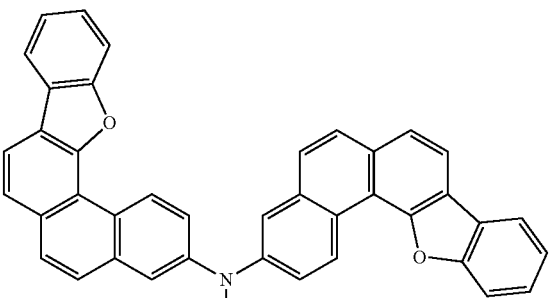
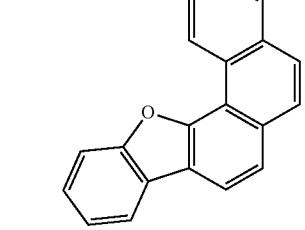
C-2
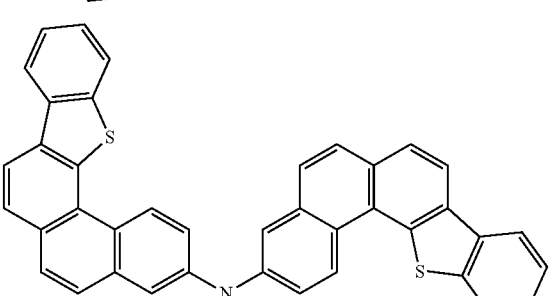
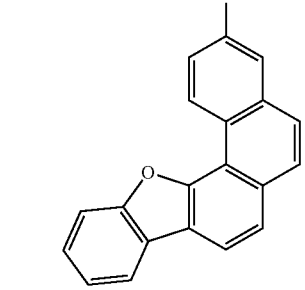

The organic compound may be used for an organic optoelectric diode.

The organic compound may be applied to an organic optoelectric diode alone or with another organic compound. When the organic compound is used with another organic compound, they may be applied in a form of a composition.

Hereinafter, an organic optoelectric diode to which the organic compound is applied is described.

The organic optoelectric diode may be any device to convert electrical energy into photoenergy and vice versa without particular limitation, and may be, for example an organic photoelectric device, an organic light emitting diode, an organic solar cell, and an organic photo-conductor drum.

The organic optoelectric diode includes an anode and a cathode facing each other, and at least one organic layer interposed between the anode and the cathode, wherein the organic layer includes the organic compound.

Herein, an organic light emitting diode as one example of an organic optoelectric diode is described with reference to drawings.

FIGS. 1 to 3 are each a cross-sectional view of an organic light emitting diode according to one embodiment.

Referring to FIG. 1, an organic light emitting diode 100 according to one embodiment includes an anode 120 and a cathode 110 facing each other and an organic layer 105 interposed between the anode 120 and cathode 110.

The anode 120 may be made of a conductor having a high work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a low work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum, silver, tin, lead, cesium, barium, and the like; a multi-layer structure material such as LiF/Al, LiO2/Al, LiF/Ca, LiF/Al and $BaF_2$/Ca, but is not limited thereto.

The organic layer 105 includes the organic compound.

Referring to FIG. 2, an organic light emitting diode 200 according to one embodiment includes an anode 120 and a cathode 110 facing each other and an organic layer 105 interposed between the anode 120 and the cathode 110, wherein the organic layer 105 includes an emission layer 130 and a hole transport layer (HTL) 140.

The hole transport layer (HTL) 140 is positioned between the anode 120 and the emission layer 130, and may include the organic compound.

Referring to FIG. 3, an organic light emitting diode 300 according to one embodiment includes an anode 120 and a cathode 110 facing each other and an organic layer 105 interposed between the anode 120 and the cathode 110.

The organic layer 105 includes an emission layer 130 and a hole transport layer (HTL) 140, and the hole transport layer (HTL) 140 includes a first hole transport layer (1-HTL) 141 positioned near the anode 120 and a second hole transport layer (2-HTL) 142 positioned near the emission layer 130.

The organic compound may be included in the second hole transport layer (2-HTL) 142 positioned near the emission layer 130.

The first hole transport layer (1-HTL) 141 may include, for example a compound represented by the following Chemical Formula 5.

[Chemical Formula 5]

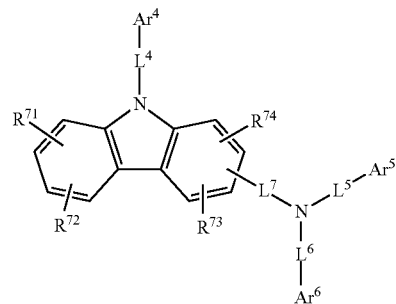

In Chemical Formula 5, $R^{71}$ to $R^{74}$ are each independently hydrogen, deuterium, a substituted or unsubstituted C1 to C10 alkyl group, a substituted or unsubstituted C6 to C30 aryl group, a substituted or unsubstituted C2 to C30 heterocyclic group, or a combination thereof, $R^{71}$ and $R^{72}$ are each independently present or are fused to each other to form a fused ring, $R^{73}$ and $R^{74}$ are each independently present or are fused to each other to form a fused ring, $Ar^4$ to $Ar^6$ are each independently a substituted or unsubstituted C6 to C30 aryl group or a substituted or unsubstituted C2 to C30 heterocyclic group, and $L^4$ to $L^7$ are independently a single bond, a substituted or unsubstituted C2 to C10 alkylene group, a substituted or unsubstituted C2 to C10 alkenylene group, a substituted or unsubstituted C2 to C10 alkynylene group, a substituted or unsubstituted C6 to C30 arylene group, a substituted or unsubstituted C2 to C30 heterocyclic group or a combination thereof.

For example, $Ar^4$ of Chemical Formula 5 may be a substituted or unsubstituted phenyl group, or a substituted or unsubstituted biphenyl group, and $Ar^5$ and $Ar^6$ of Chemical Formula 5 may be independently one of a substituted or unsubstituted phenyl group, a substituted or unsubstituted biphenyl group, a substituted or unsubstituted fluorene group, a substituted or unsubstituted bisfluorene group, a substituted or unsubstituted triphenylene group, a substituted or unsubstituted anthracene group, a substituted or unsubstituted terphenyl group, a substituted or unsubstituted dibenzofuran group or a substituted or unsubstituted dibenzothiophenyl group.

The compound represented by Chemical Formula 5 may be, for example one of the compounds represented by the following J-1 to J-144, but is not limited thereto.

-continued
[J-1]
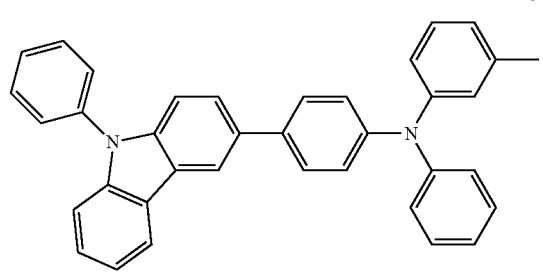
[J-2]
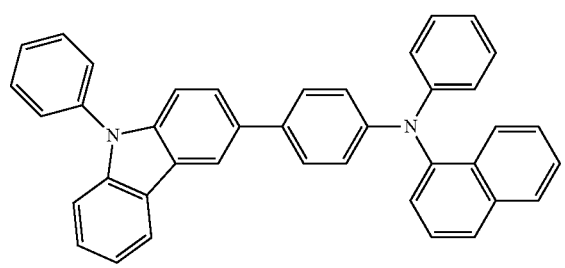
[J-3]
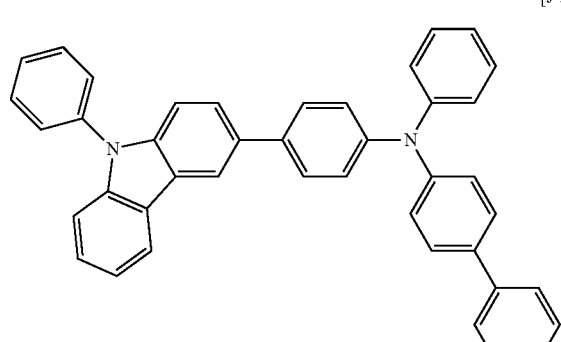
[J-4]
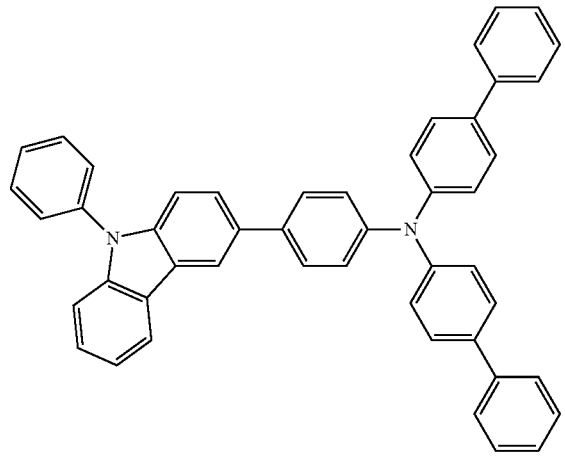
[J-5]
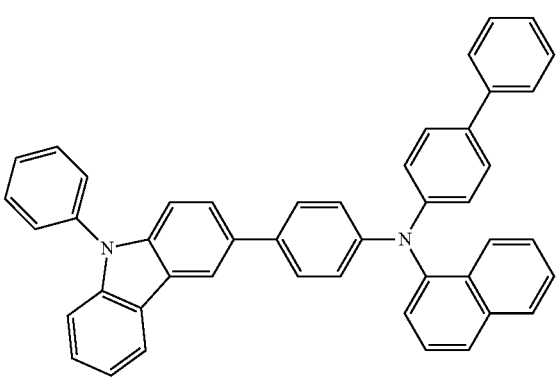
[J-6]
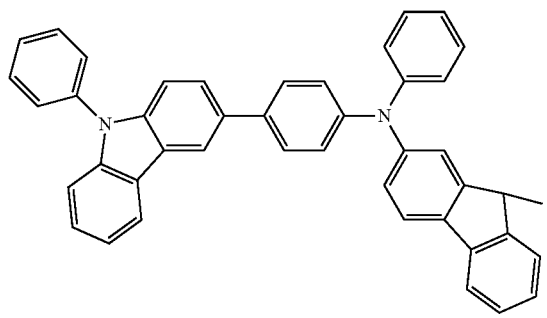
[J-7]
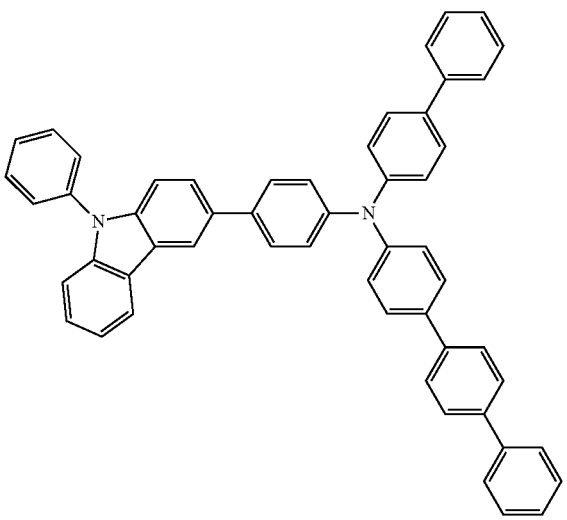
[J-8]
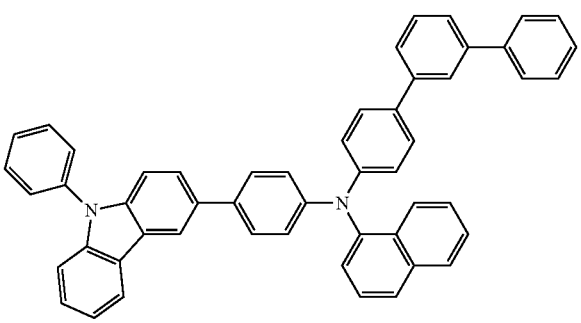

[J-9]
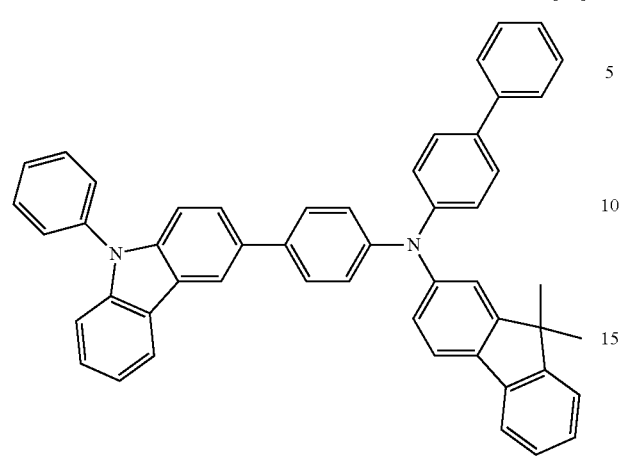
[J-10]
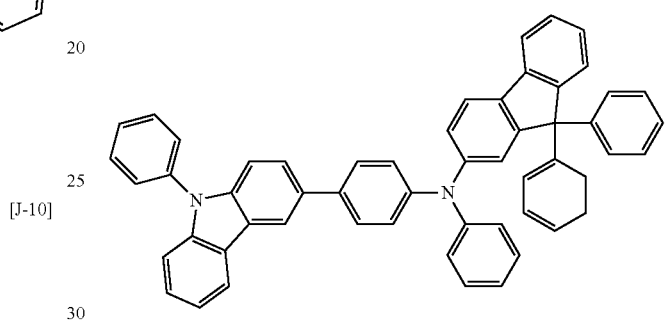
[J-11]
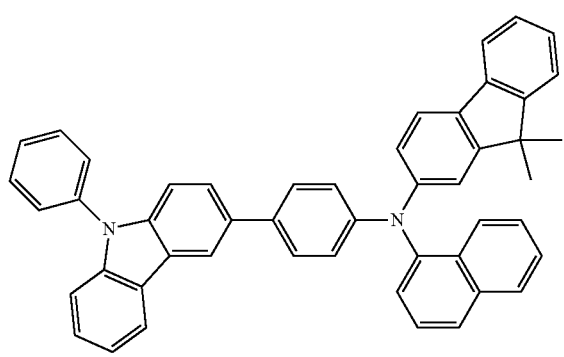
[J-12]
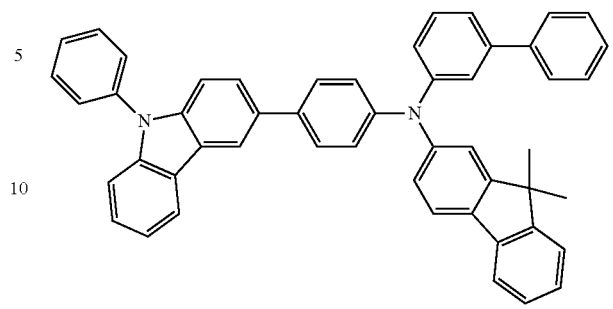
[J-13]
[J-14]
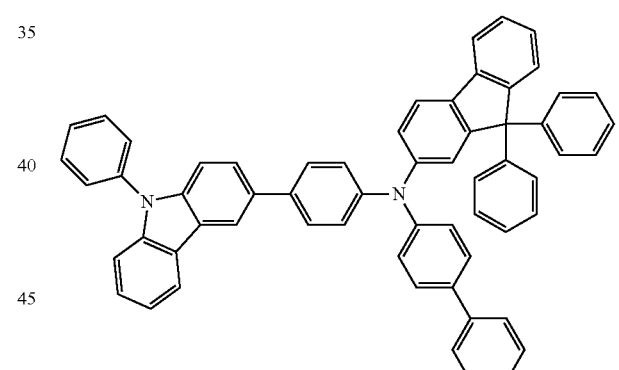
[J-15]
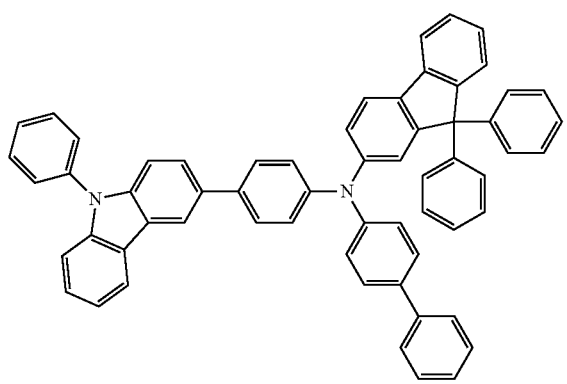

[J-16]
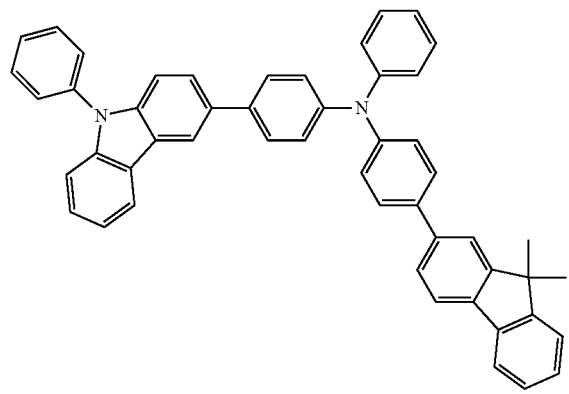
[J-17]
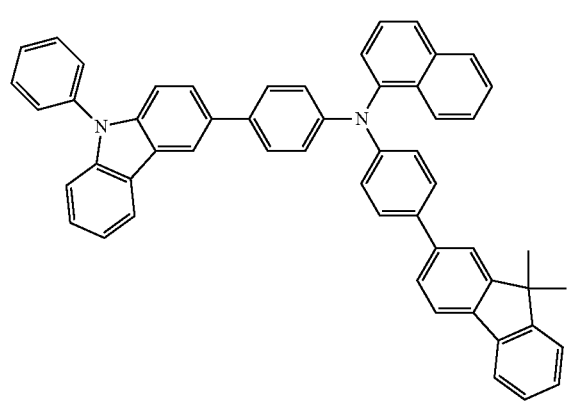
[J-18]
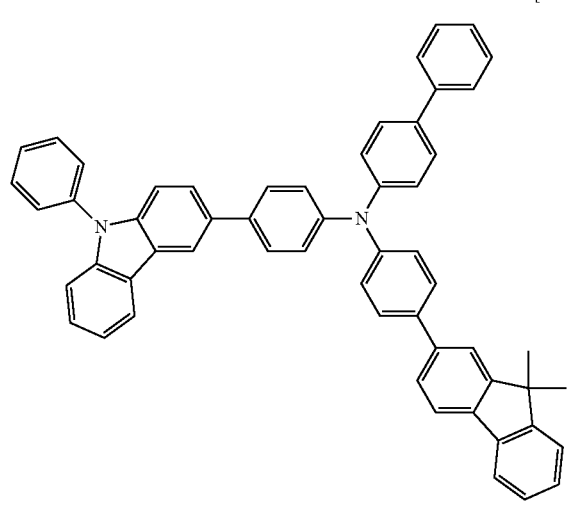
[J-19]
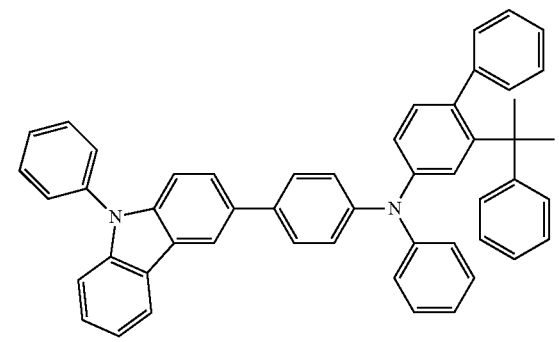
[J-20]
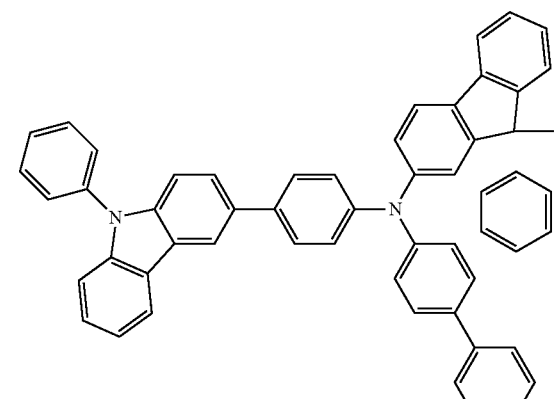
[J-21]
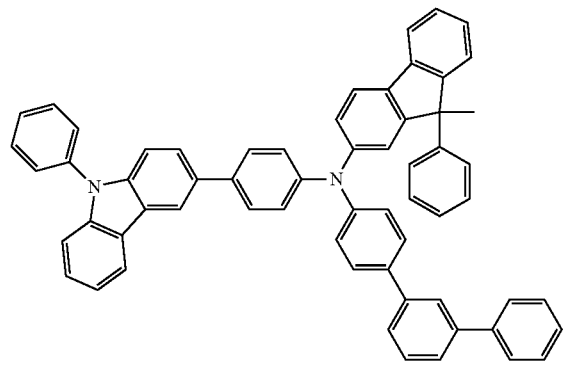
[J-22]
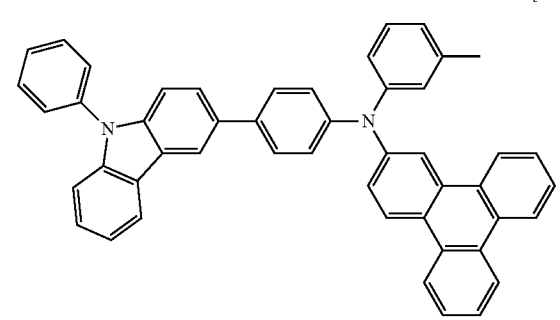

[J-23]
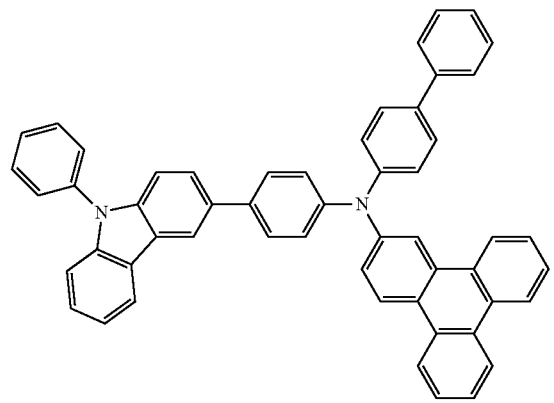
[J-27]
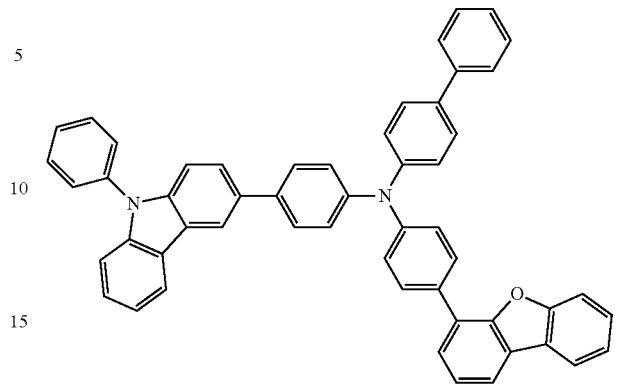
[J-24]
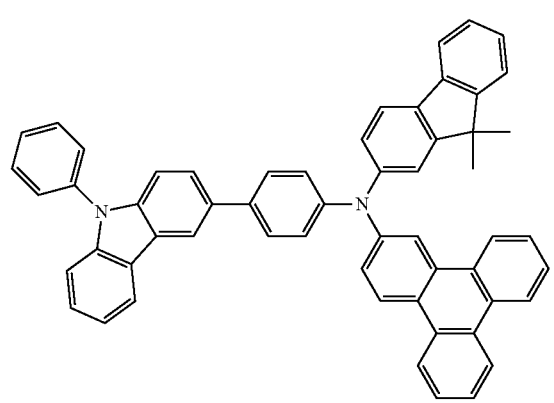
[J-28]
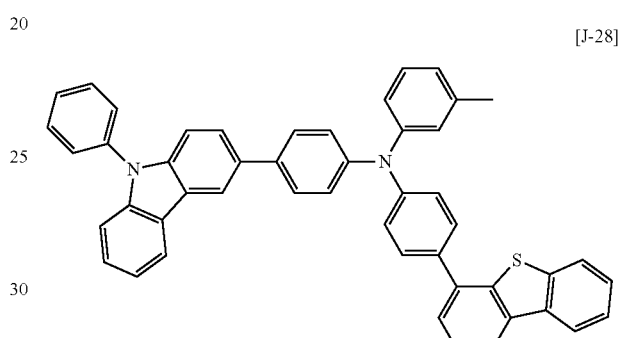
[J-25]
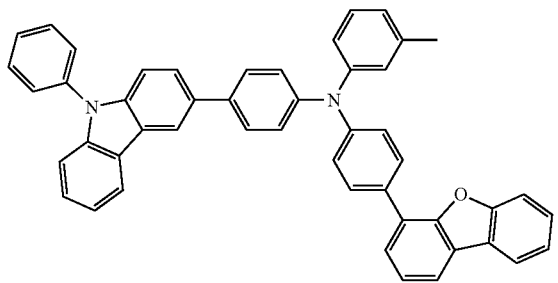
[J-29]
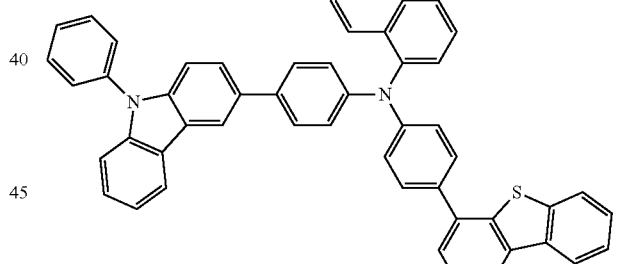
[J-26]
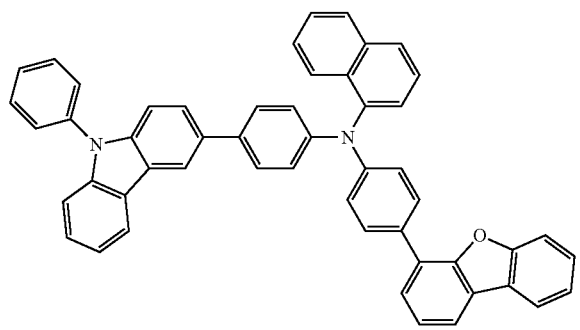
[J-30]
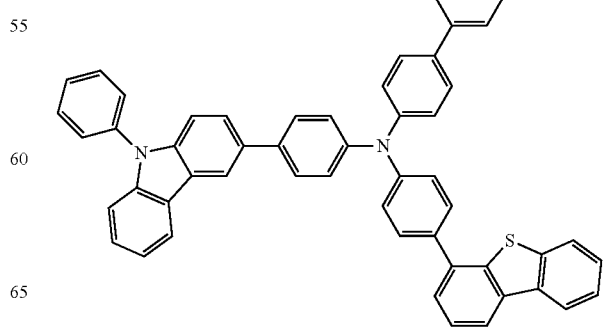

[J-31]
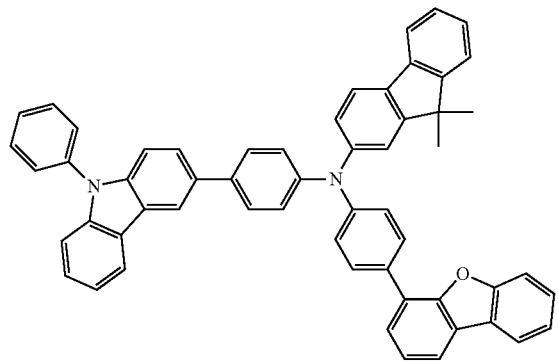
[J-32]
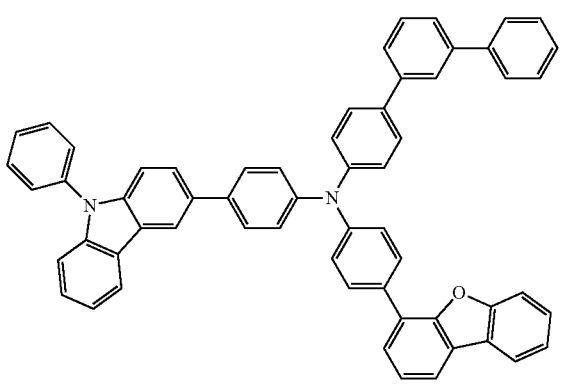
[J-33]
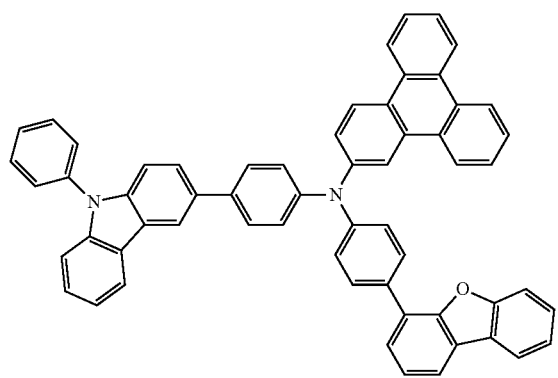
[J-34]
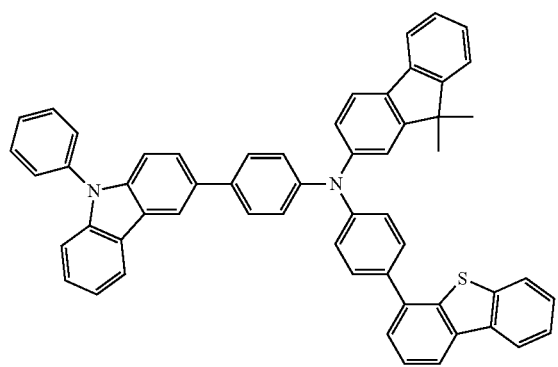
[J-35]
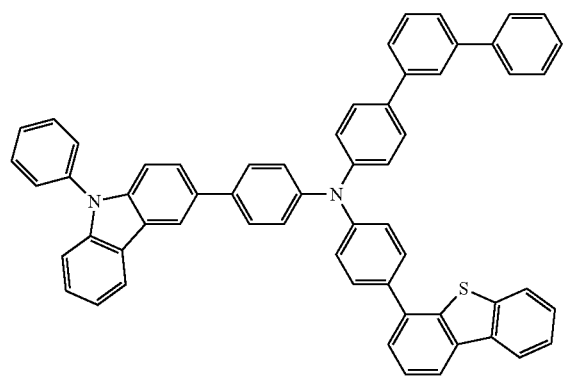
[J-36]
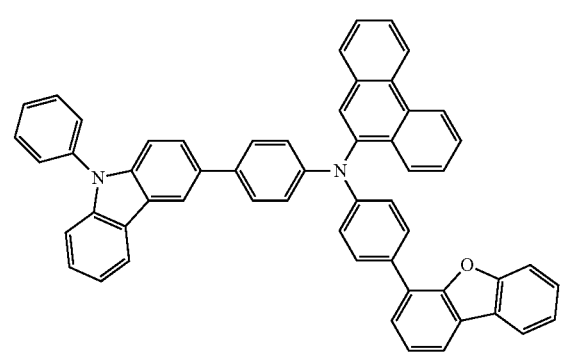
[J-37]
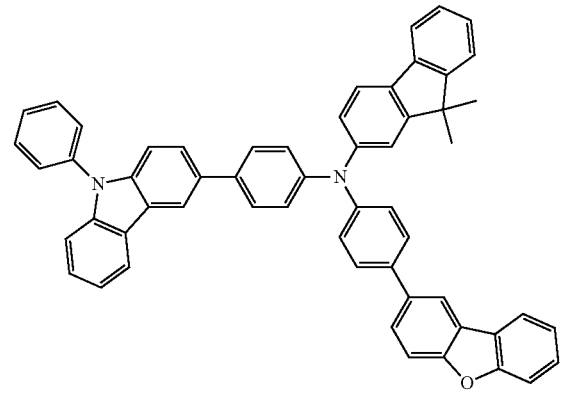
[J-38]
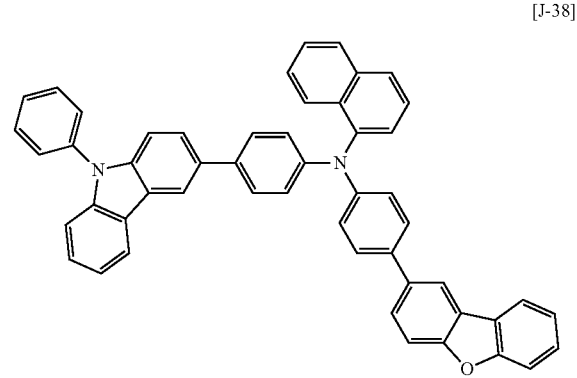

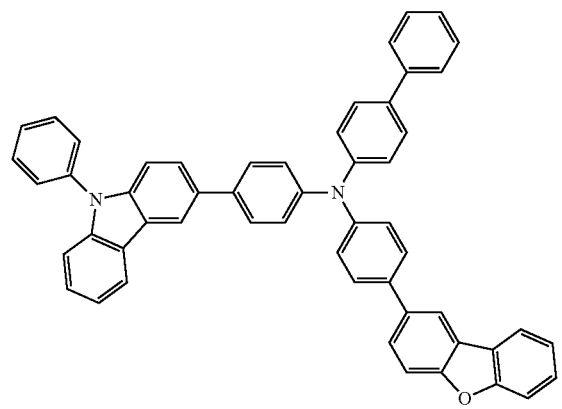
[J-39]
[J-40]
[J-41]
[J-42]
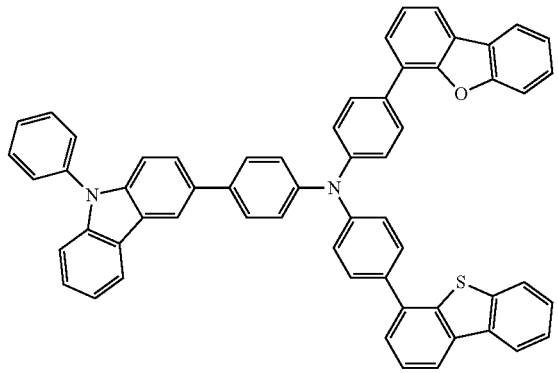
[J-43]
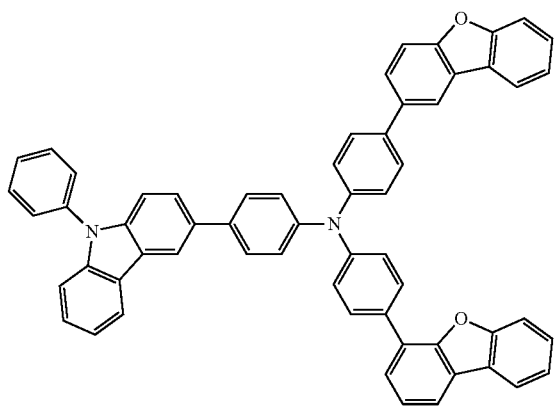
[J-44]
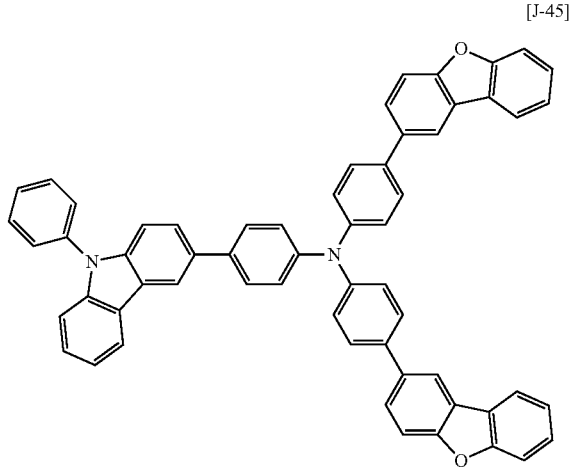
[J-45]
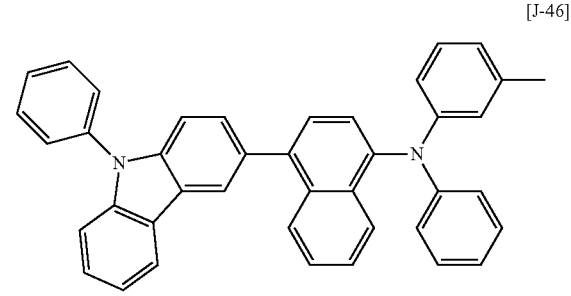
[J-46]

[J-47]
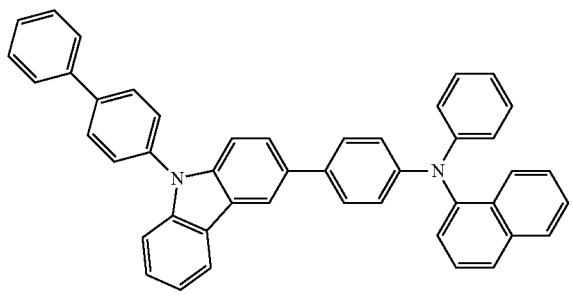
[J-48]
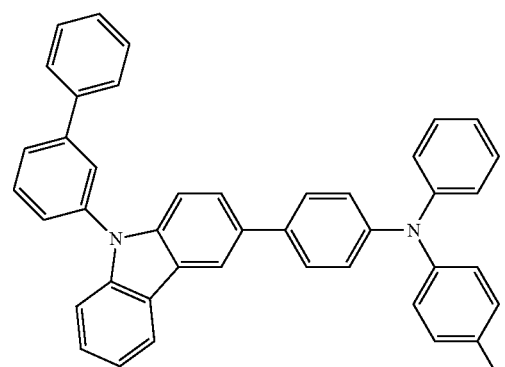
[J-49]
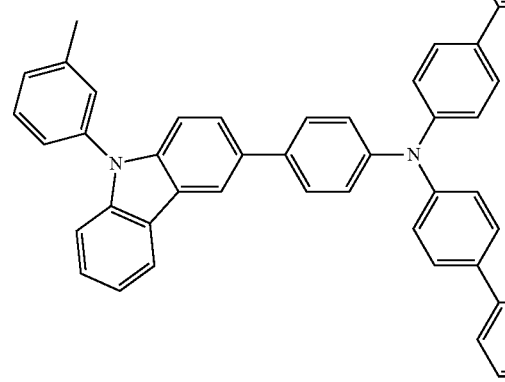
[J-50]
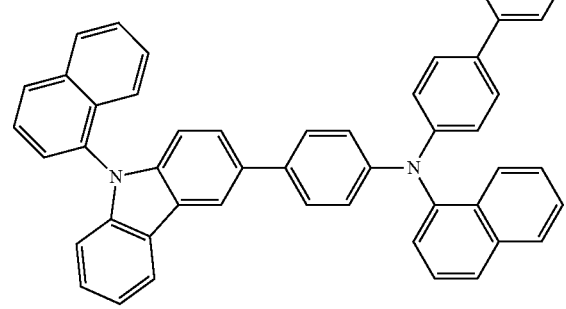
[J-51]
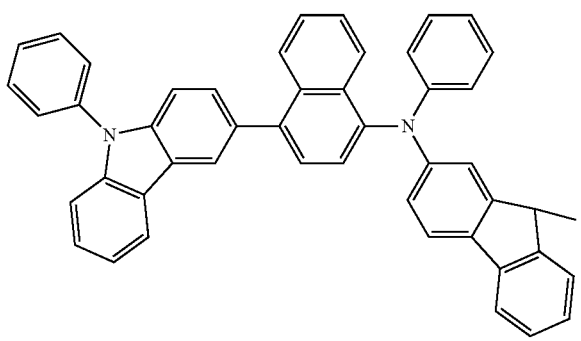
[J-52]
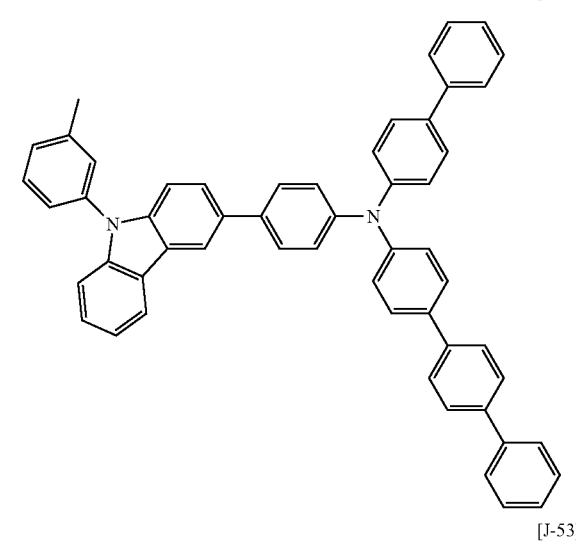
[J-53]
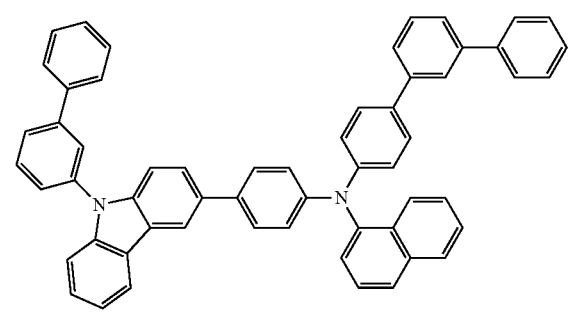
[J-54]
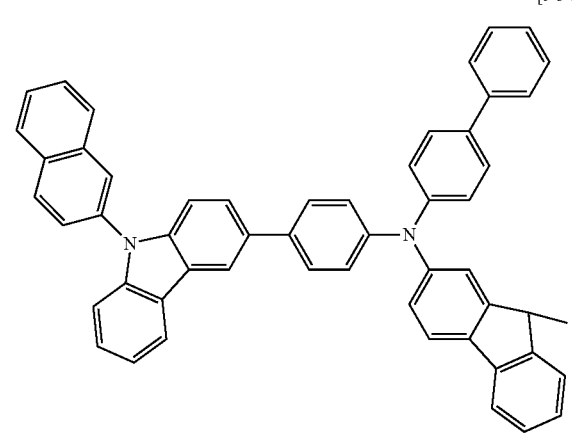

[J-55]
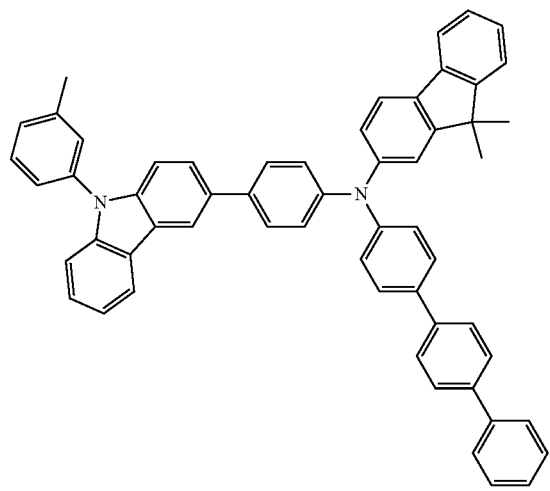
[J-56]
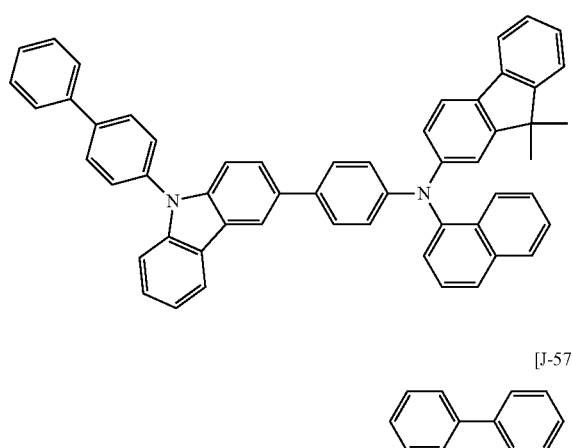
[J-57]
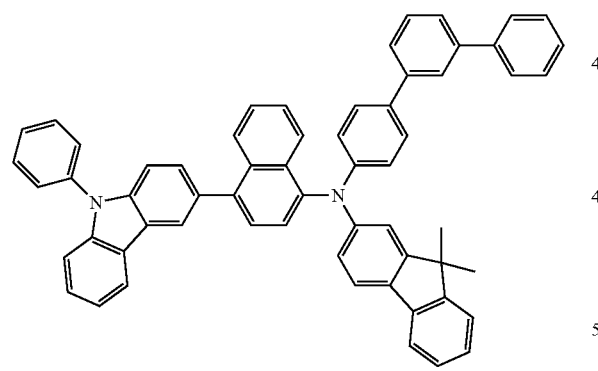
[J-58]
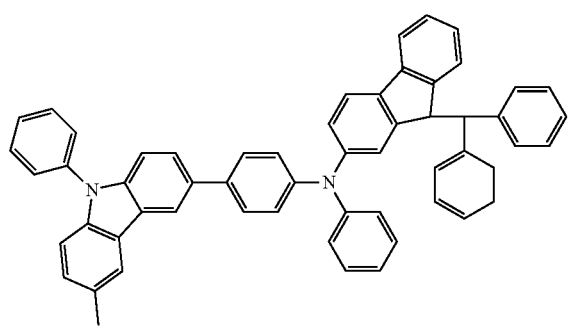
[J-59]
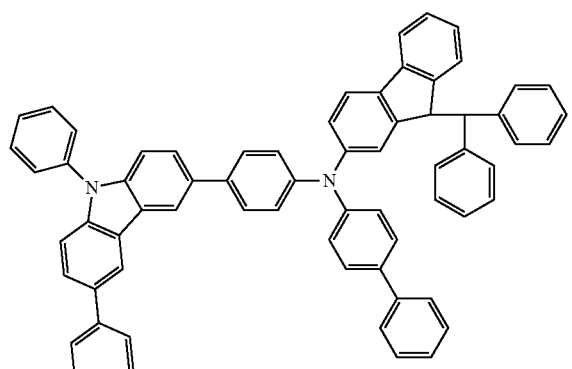
[J-60]
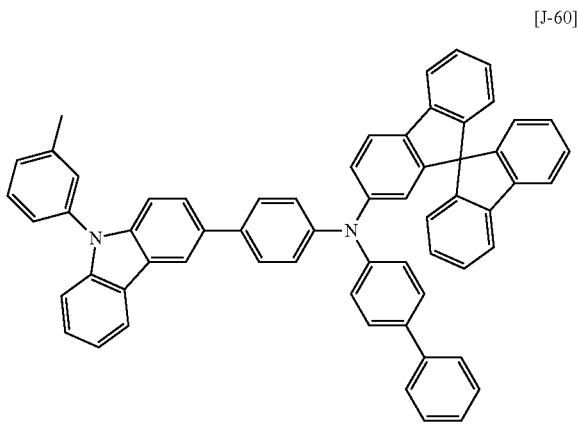
[J-61]
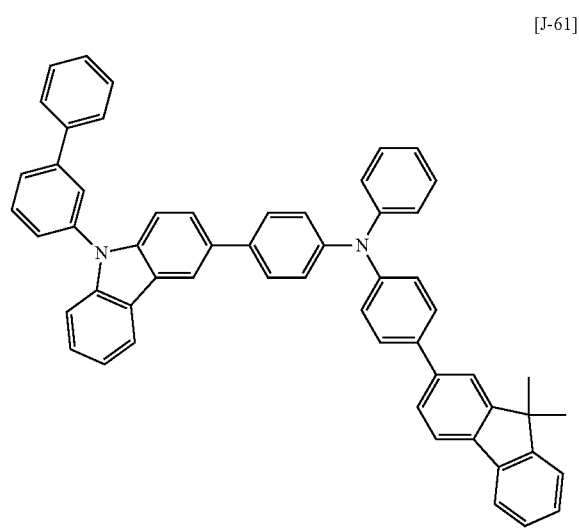

[J-62]
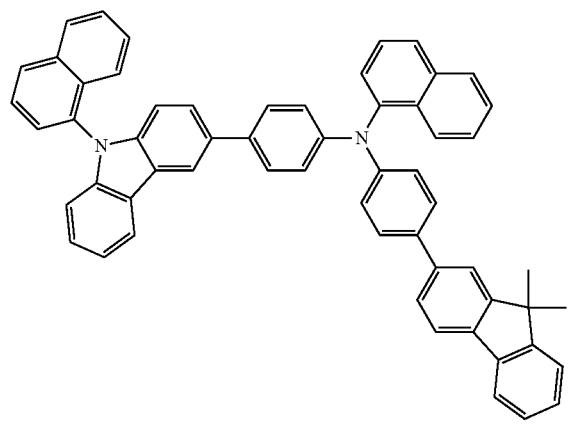
[J-63]
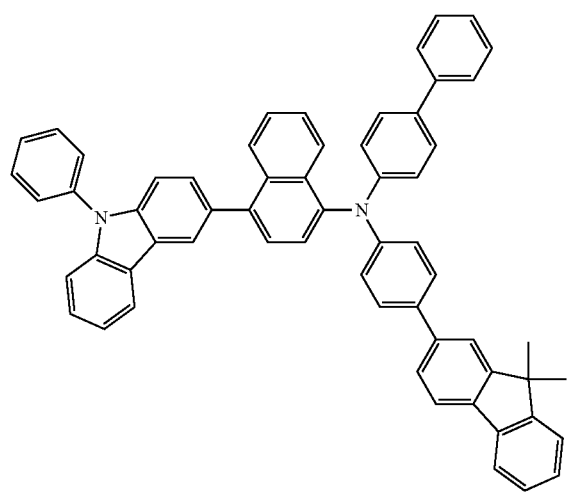
[J-64]
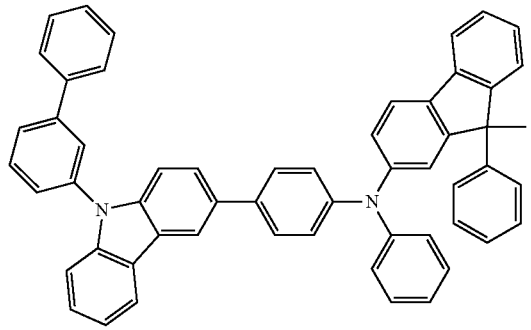
[J-65]
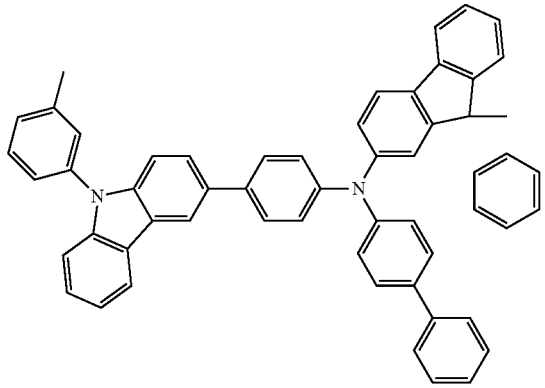
[J-66]
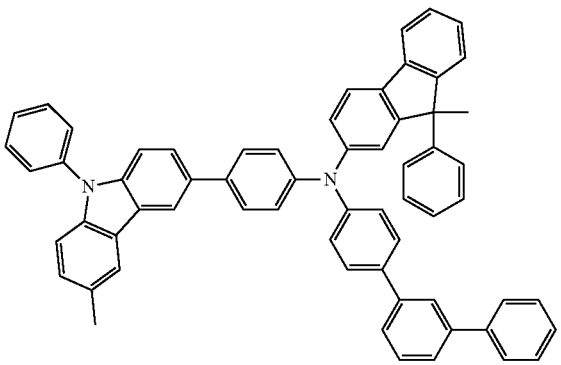
[J-67]
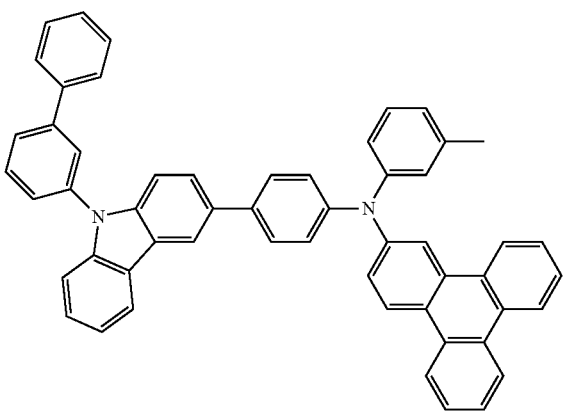
[J-68]
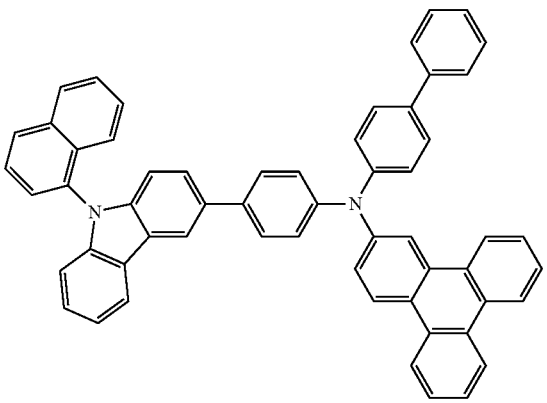

-continued
[J-69]
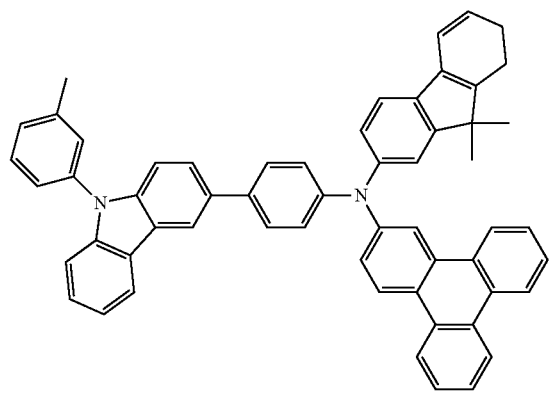
[J-70]
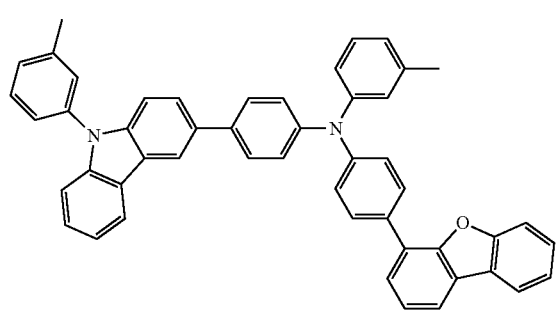
[J-73]
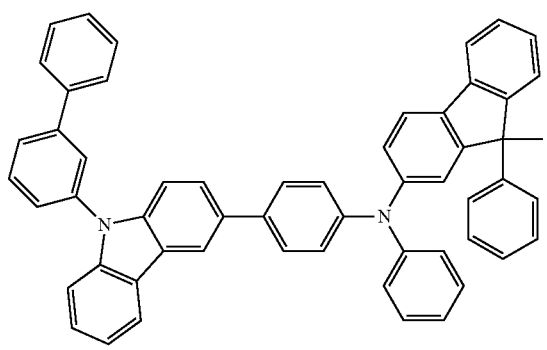
[J-74]
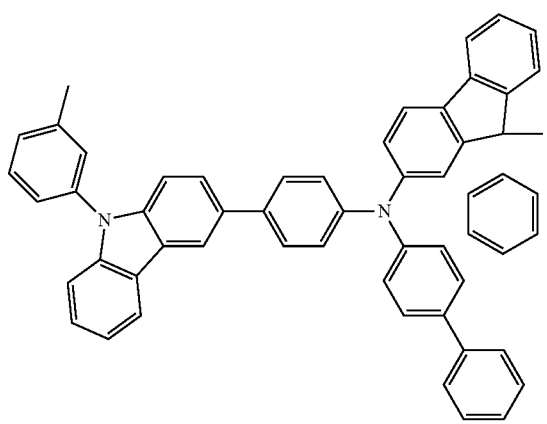
[J-71]
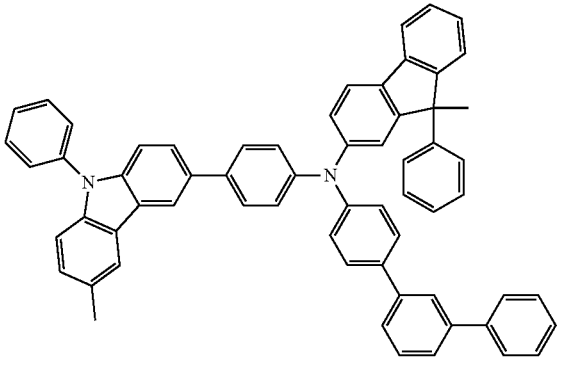
[J-75]
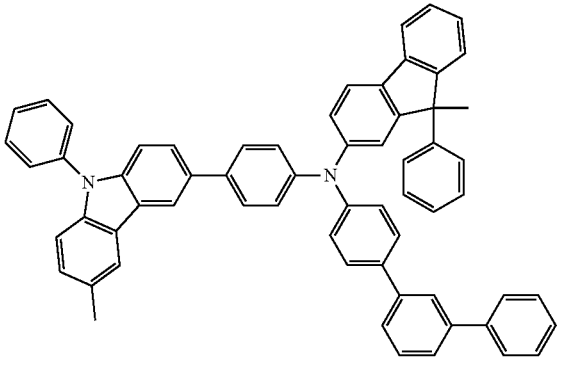
[J-72]
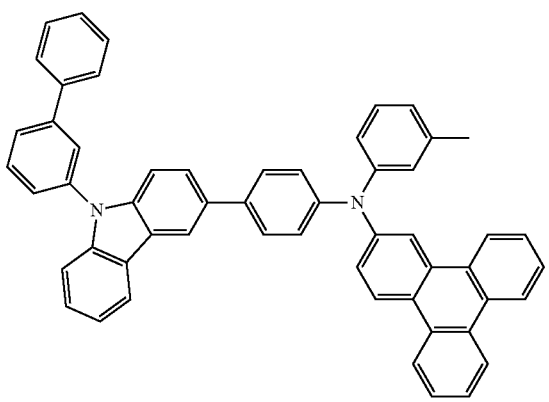
[J-76]
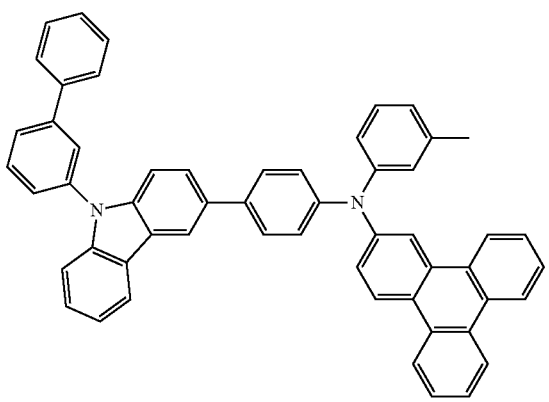

[J-77]
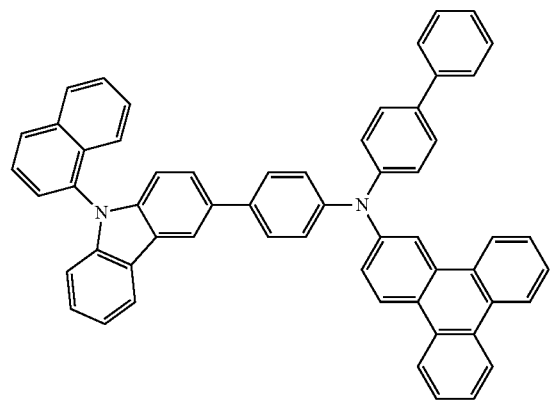
[J-81]
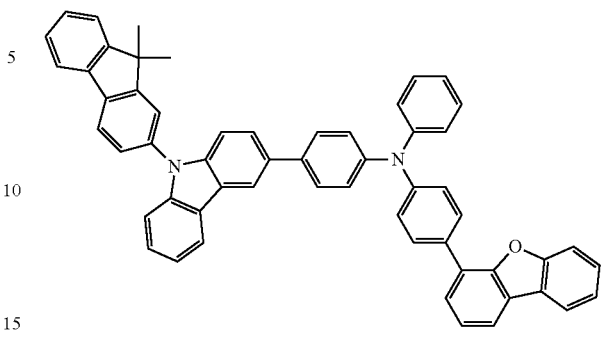
[J-78]
[J-82]
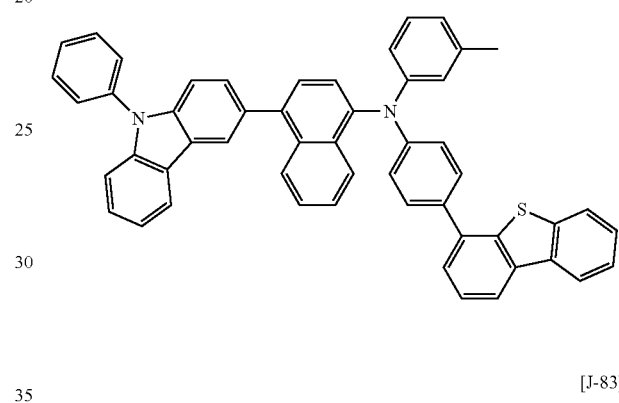
[J-79]
[J-83]
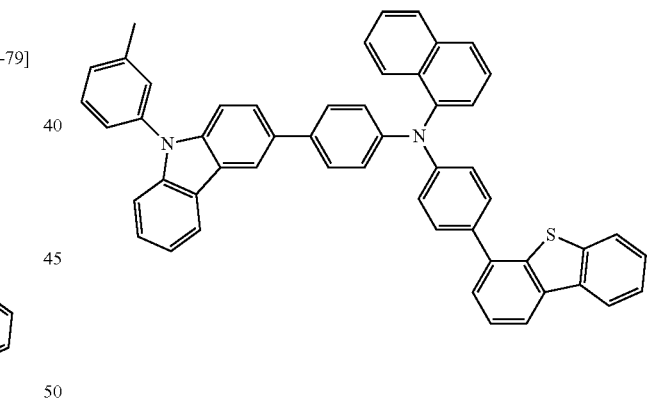
[J-80]
[J-84]
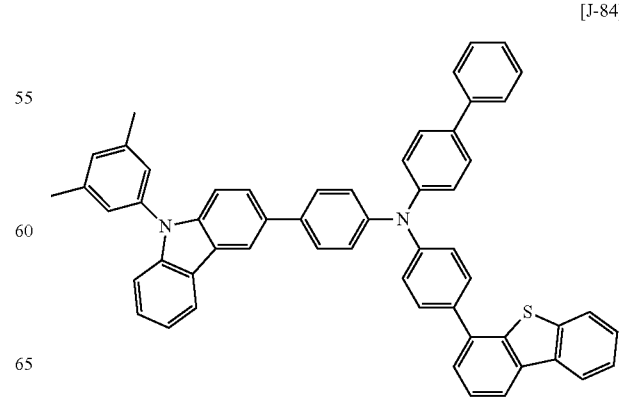

[J-85]
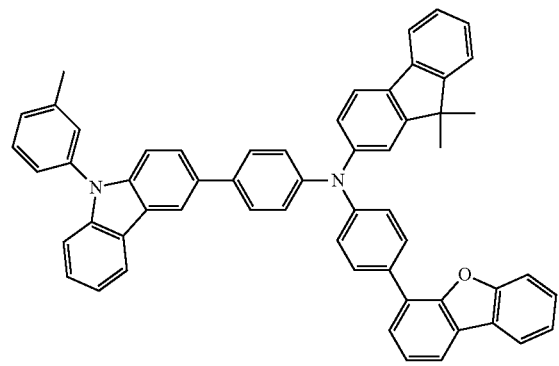
[J-89]
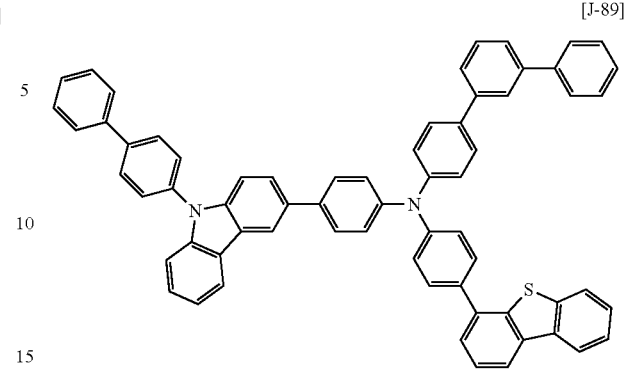
[J-86]
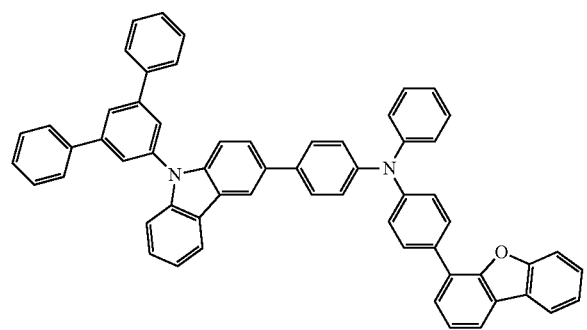
[J-90]
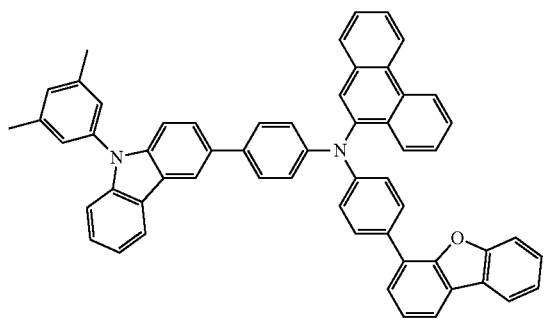
[J-87]
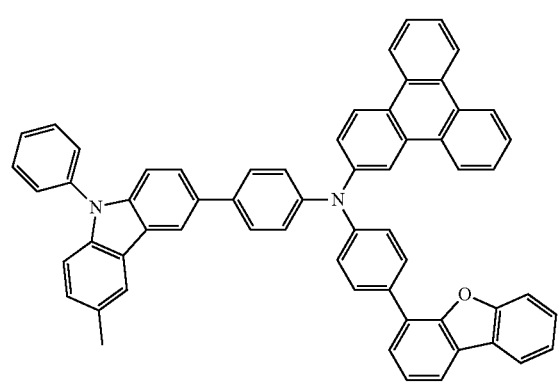
[J-91]
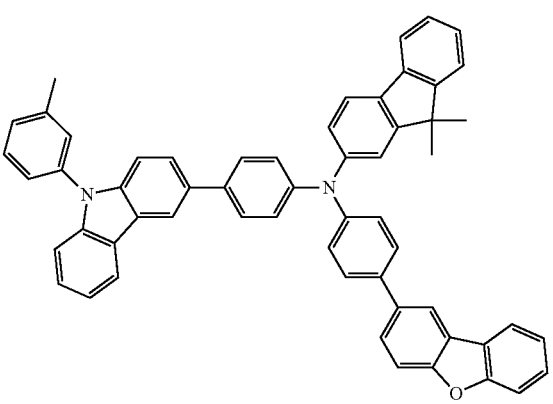
[J-88]
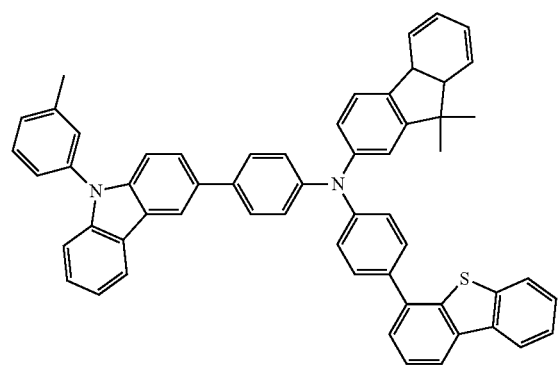
[J-92]
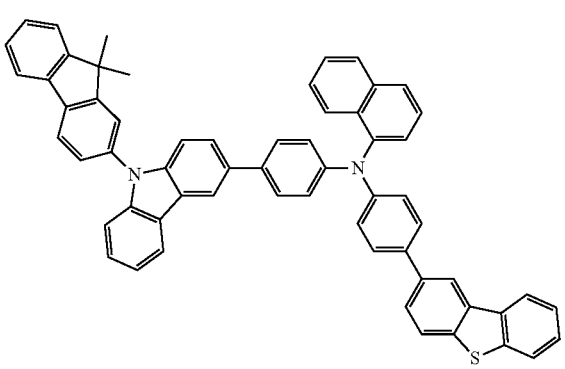

-continued
[J-93]
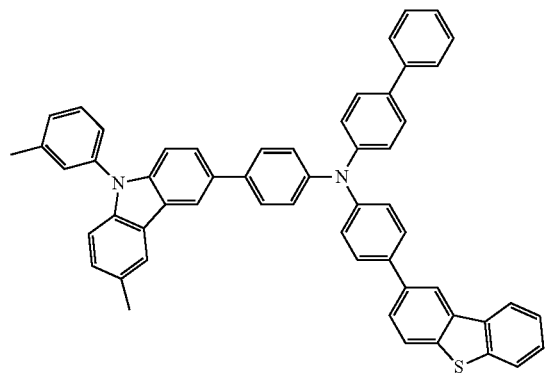
[J-94]
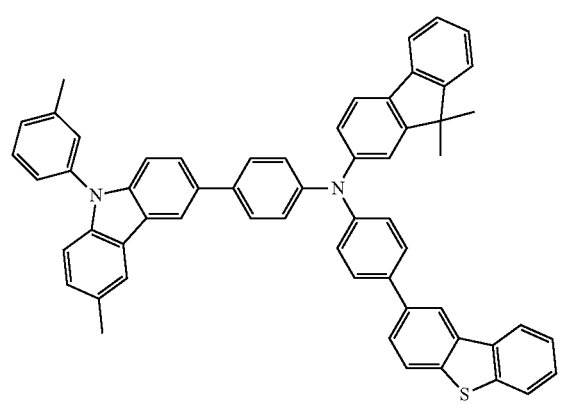
[J-95]
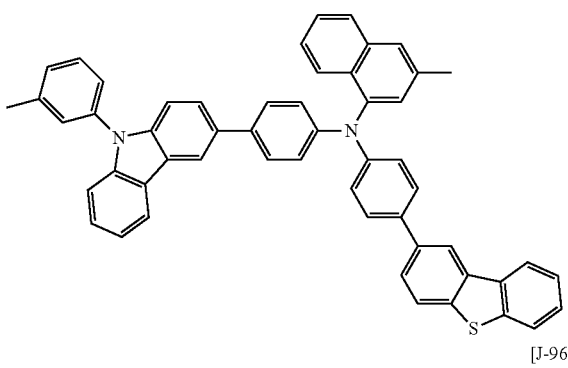
[J-96]
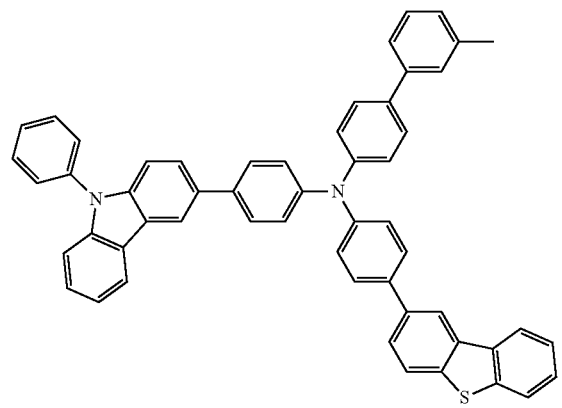
-continued
[J-97]
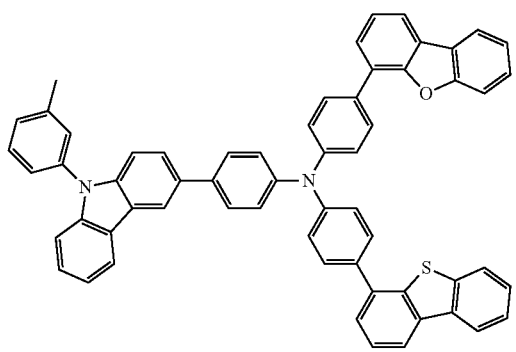
[J-98]
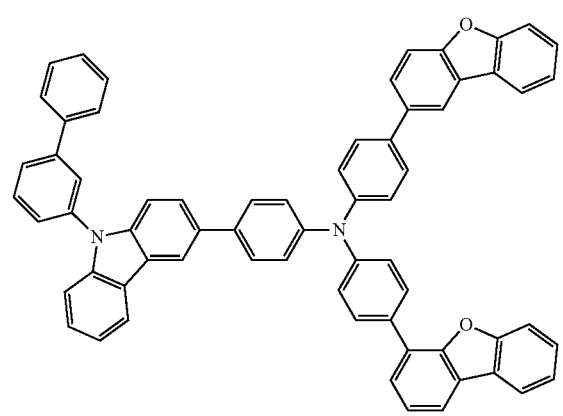
[J-99]
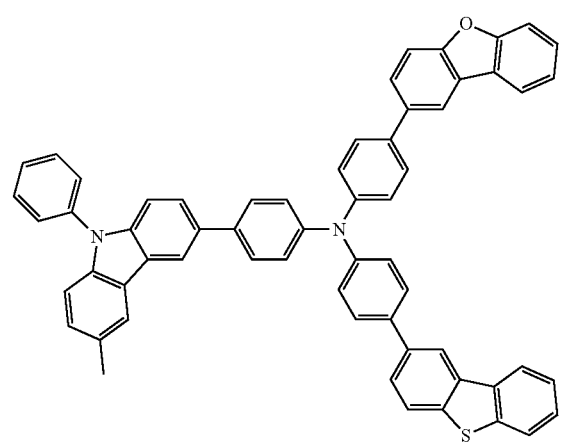
[J-100]
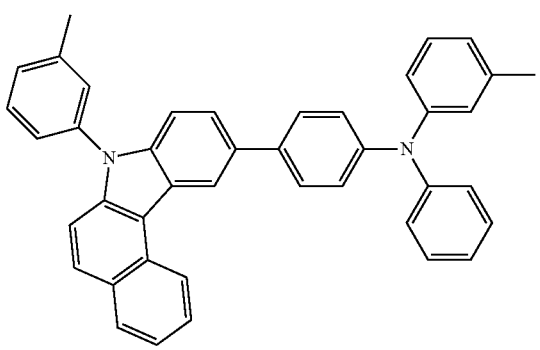

[J-101]
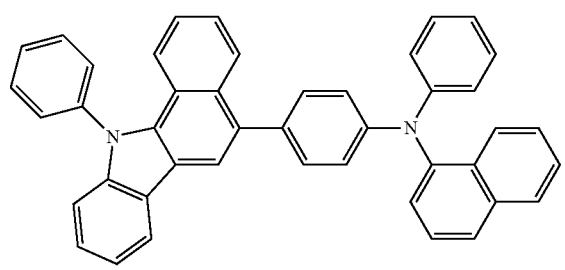
[J-102]
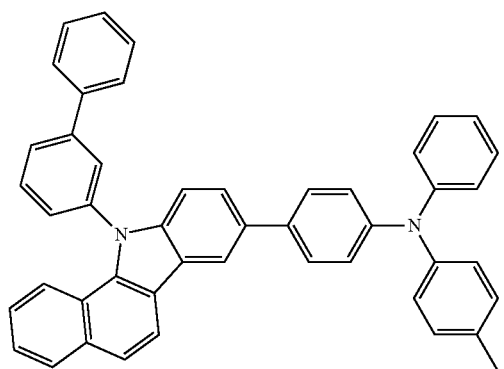
[J-105]
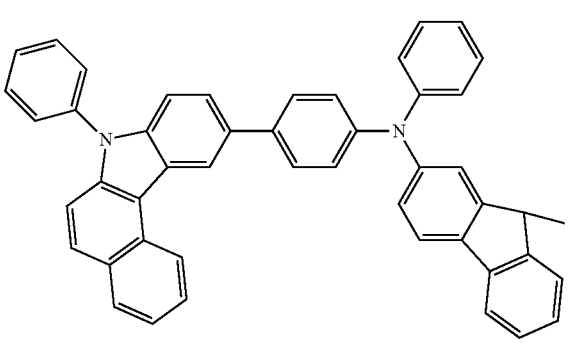
[J-106]
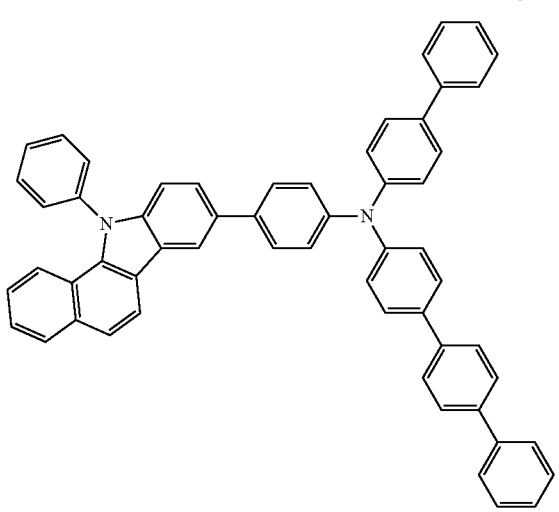
[J-103]
[J-104]
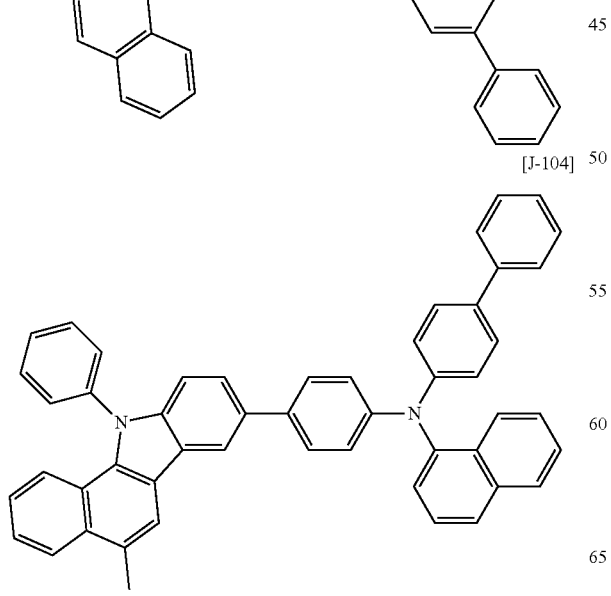
[J-107]

[J-108]
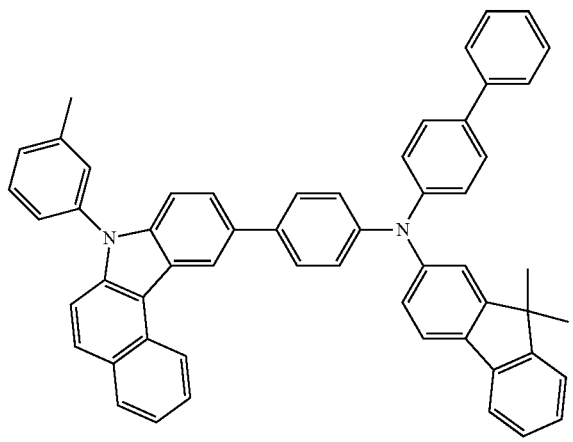
[J-111]
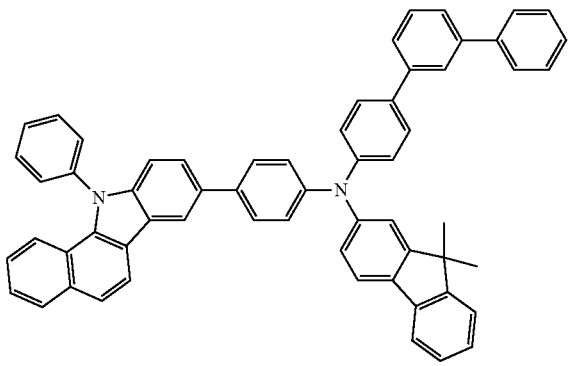
[J-109]
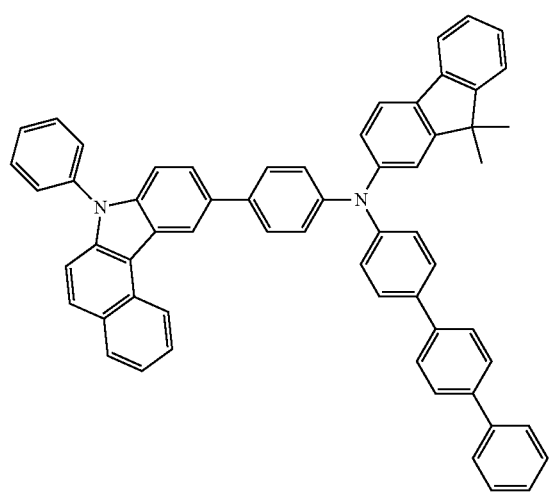
[J-112]
[J-113]
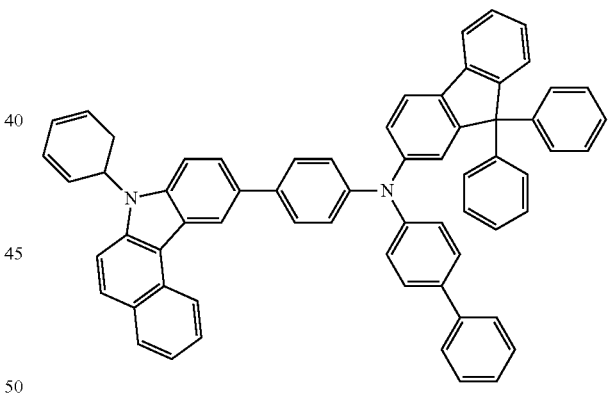
[J-110]
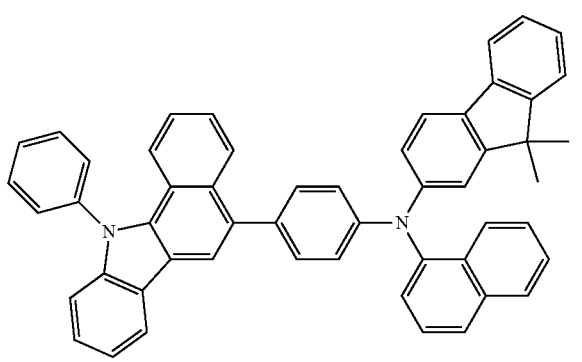
[J-114]
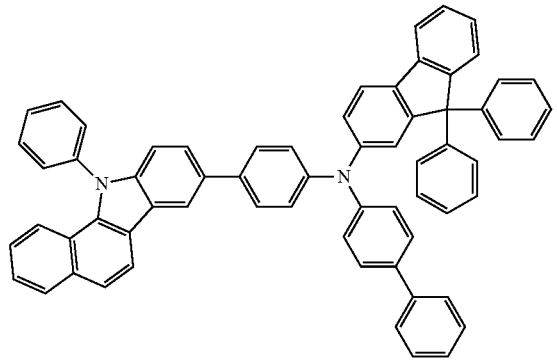

[J-115]
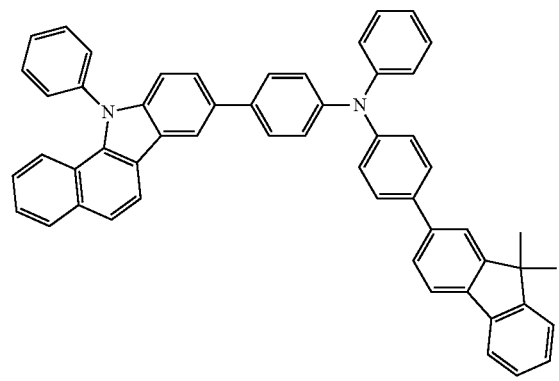
[J-118]
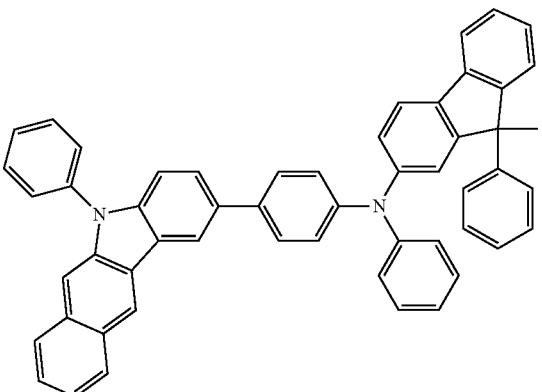
[J-116]
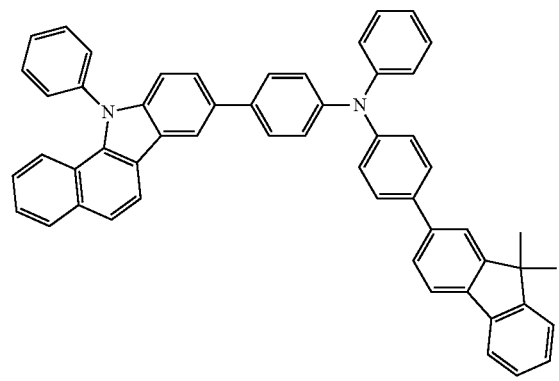
[J-119]
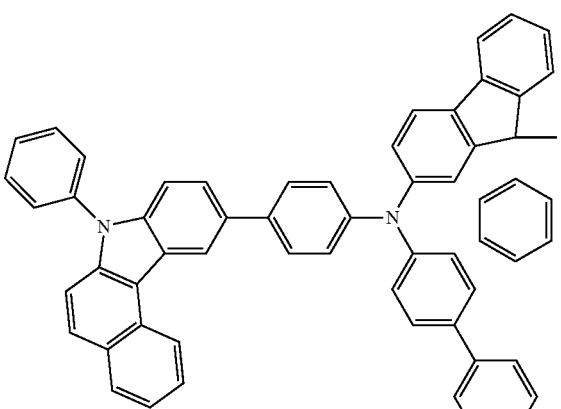
[J-120]
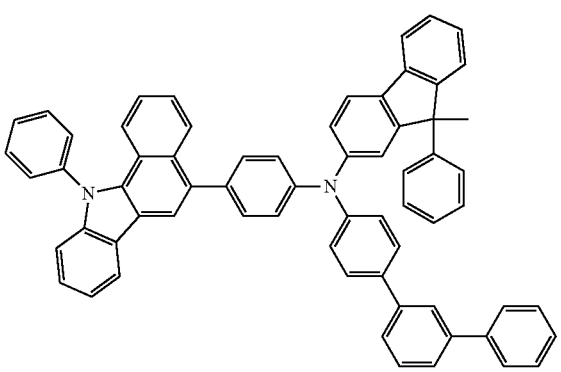
[J-117]
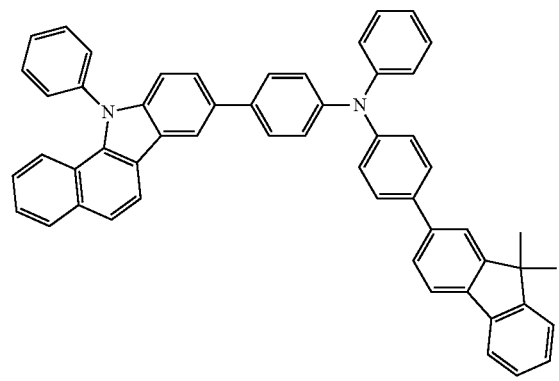
[J-121]
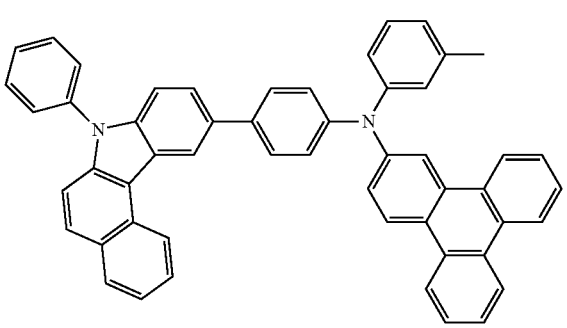

-continued
[J-122]
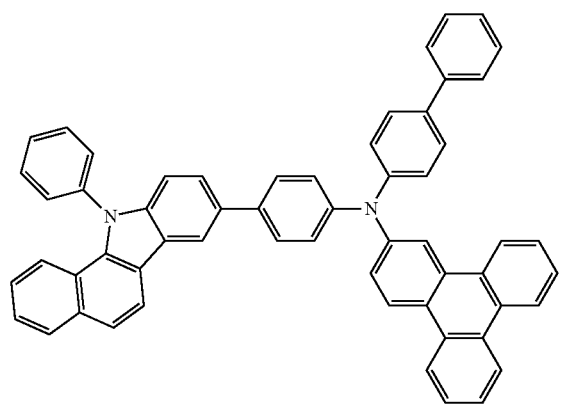
[J-123]
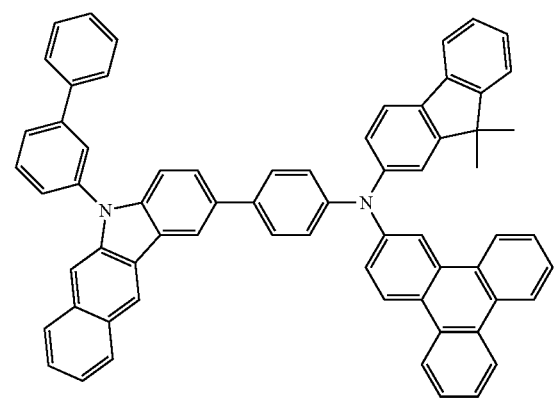
[J-124]
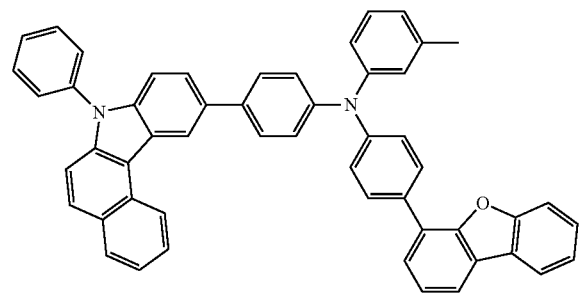
[J-125]
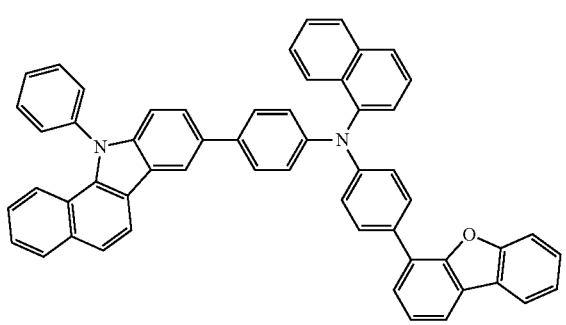
-continued
[J-126]
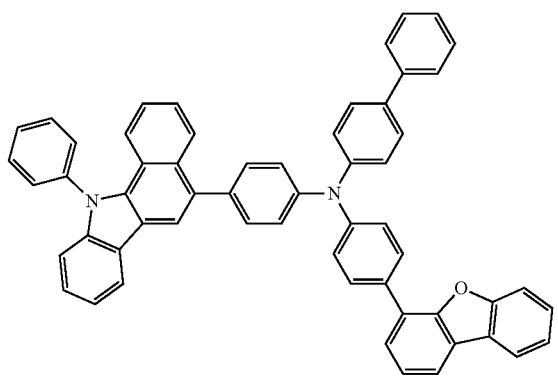
[J-127]
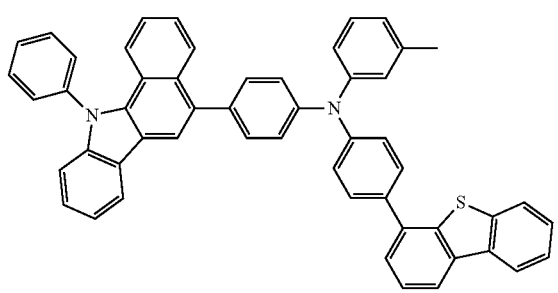
[J-128]
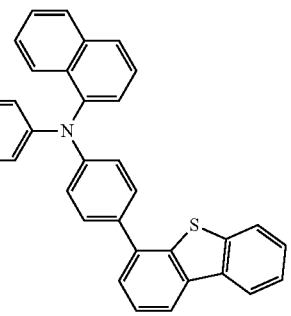
[J-129]
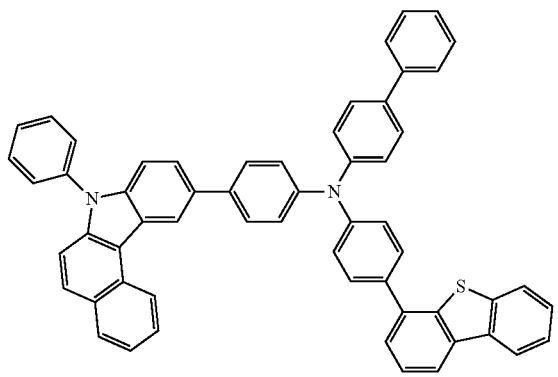

-continued
[J-130]
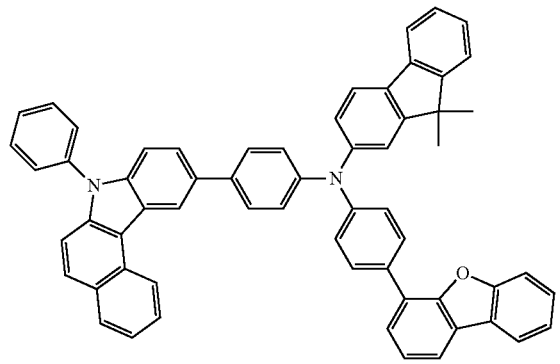
[J-131]
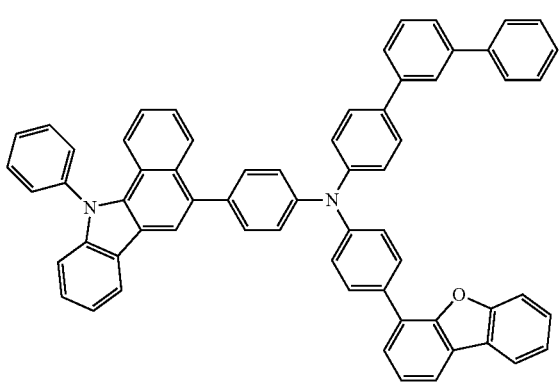
[J-132]
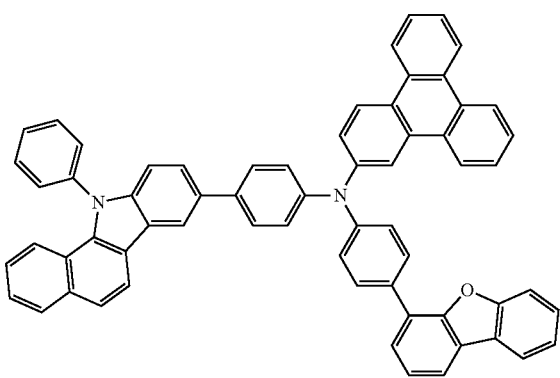
[J-133]
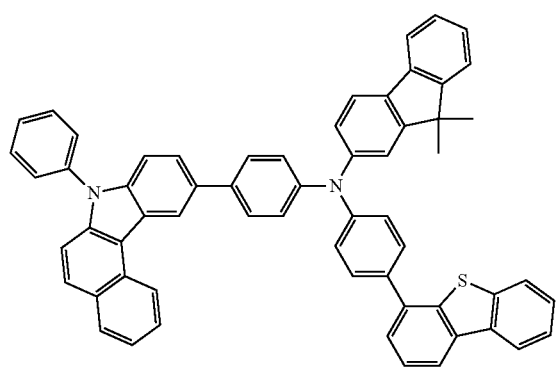
-continued
[J-134]
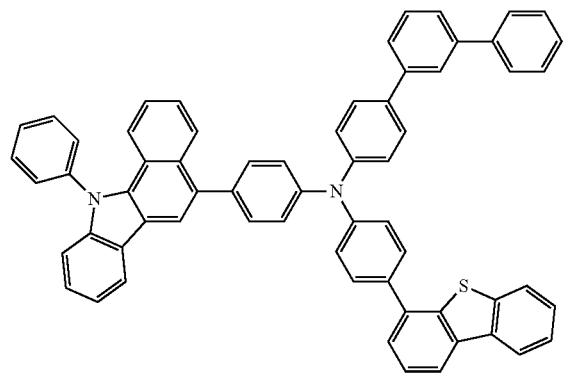
[J-135]
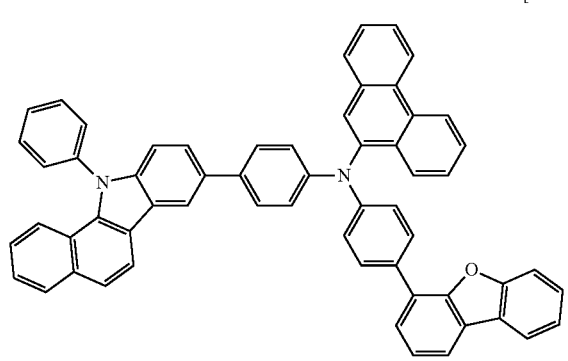
[J-136]
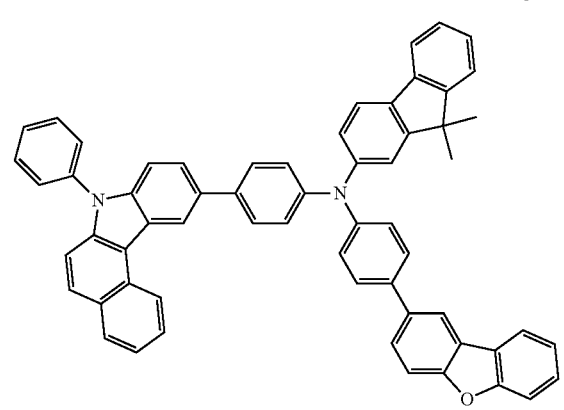
[J-137]
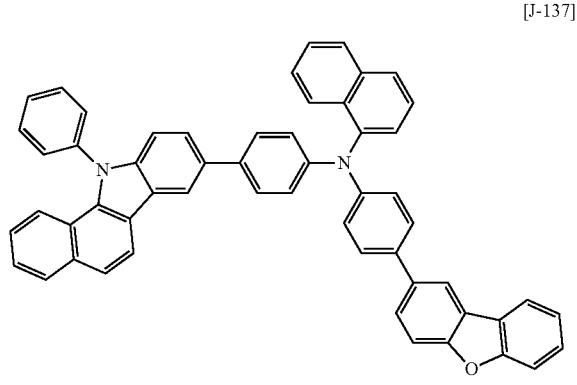

[J-138]
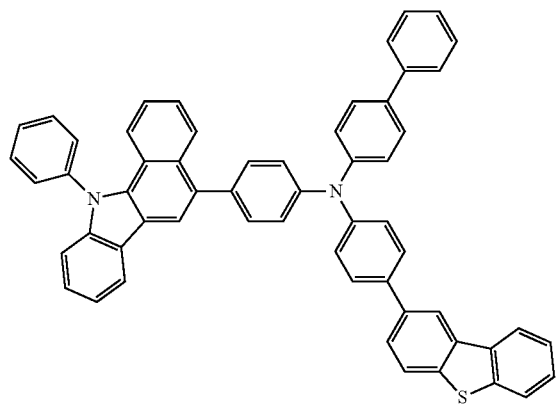

[J-139]
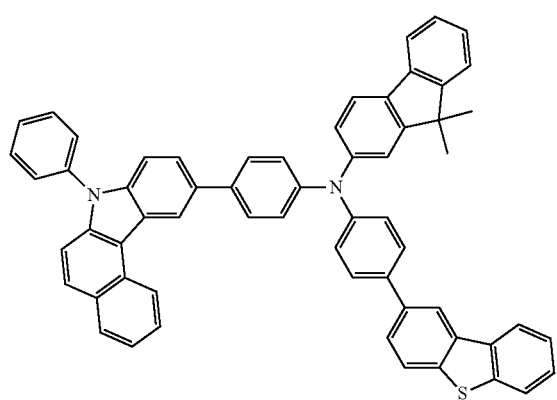

[J-140]
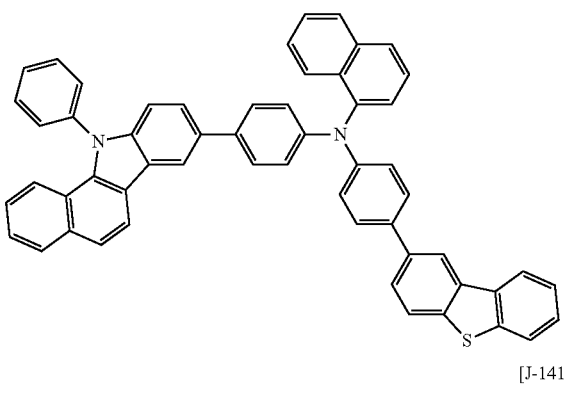

[J-141]
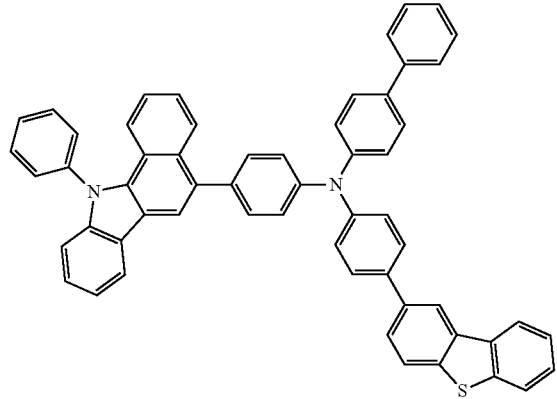

[J-142]
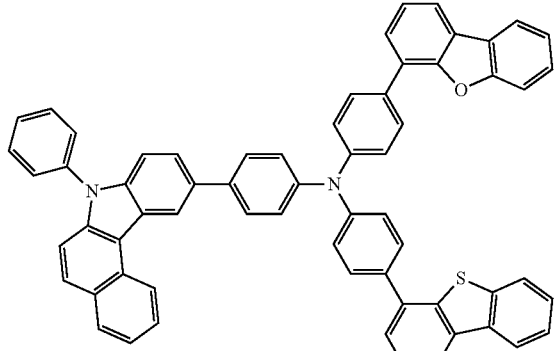

[J-143]
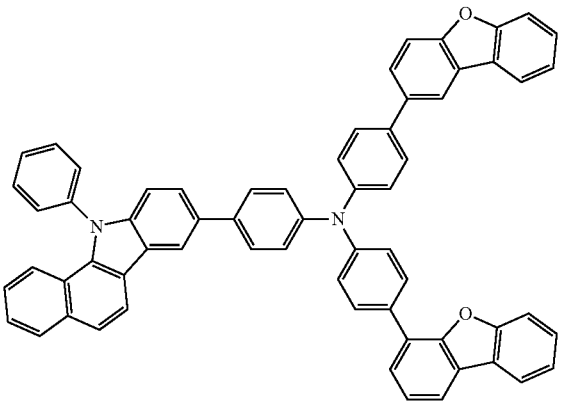

[J-144]
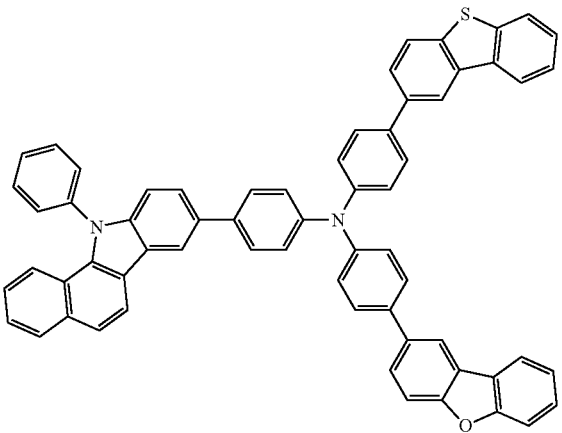

In FIGS. 1 to 3, the organic layer 105 may further include a hole injection layer (HIL), an electron blocking layer, an electron transport layer (ETL), an electron injection layer (EIL) and/or a hole blocking layer beside the emission layer 130 and the hole transport layer (HTL) 140.

The organic light emitting diodes 100, 200, and 300 may be manufactured by forming an anode or a cathode on a substrate, forming an organic layer in accordance with a dry coating method such as evaporation, sputtering, plasma plating, and ion plating, and forming a cathode or an anode thereon.

The organic light emitting diode may be applied to an organic light emitting diode display.

MODE FOR INVENTION

Hereinafter, the embodiments are illustrated in more detail with reference to examples. These examples, however, are not in any sense to be interpreted as limiting the scope of the invention.

Hereinafter, a starting material and a reaction material used in Examples and Synthesis Examples were purchased from Sigma-Aldrich Co. Ltd. or TCI Inc. unless otherwise mentioned.

Synthesis of Intermediates
Synthesis of Intermediate K-1

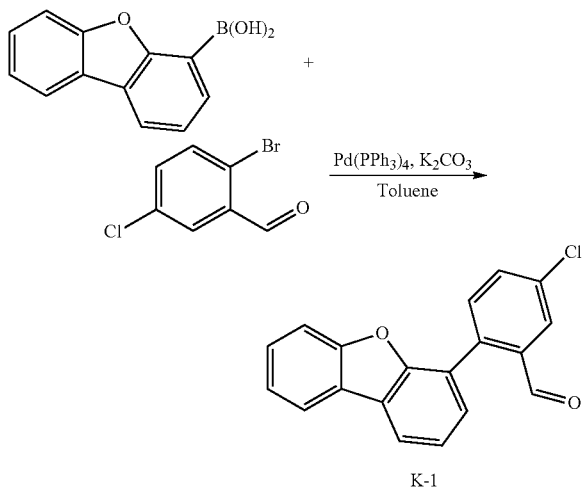

53.15 g (250.61 mmol) of 4-dibenzofuranboronic acid, 50 g (227.83 mmol) of 2-bromo-5-chloro-benzaldehyde, 62.98 g (455.66 mmol) of potassium carbonate and 7.89 g (6.84 mmol) of tetrakistriphenylphosphine palladium were put in a round-bottomed flask and then, suspended in 1000 ml of toluene and 500 ml of distilled water and refluxed and agitated under a nitrogen atmosphere for 12 hours. When the reaction was terminated, the resultant was extracted with toluene, and the extracted solution was dried with magnesium sulfate, filtered with silica gel, and concentrated under a reduced pressure. Then, 300 ml of methanol was added to the concentrated solution, and a solid produced therein was agitated for one hour and filtered, obtaining 64.64 g of a compound K-1 (a yield of 93%).

LC-Mass (a theoretical value: 306.74 g/mol, a measured value: M+=306.79 g/mol)

Synthesis of Intermediate K-2

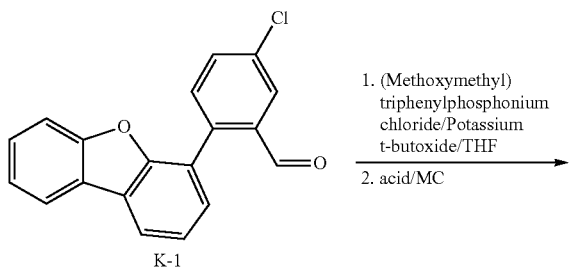

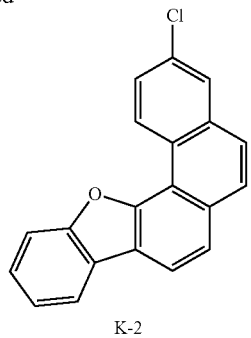

64.64 g (210.73 mmol) of the compound K-1 and 79.46 g (231.80 mmol) of (methoxymethyl)triphenyl phosphonium chloride were suspended in 600 ml of tetrahydrofuran in a round-bottomed flask and then, maintained at 0° C. Subsequently, 28.38 g (252.87 mmol) of potassium t-butoxide was slowly added thereto at 0° C., and the mixture was agitated for 12 hours at room temperature. When the reaction was terminated, 600 ml of distilled water was added thereto, the mixture was extracted, and the extracted solution was concentrated, suspended in 500 ml of methylene chloride and dried with magnesium sulfate, filtered with silica gel, and then, concentrated again. The concentrated reaction solution was dissolved in 400 ml of methylene chloride, 20 g of methoic acid was slowly added thereto, and the mixture was agitated for 12 hours at room temperature. When the reaction was terminated, a solid produced therein was filtered, washed with 200 ml of distilled water and 200 ml of methanol, and dried, obtaining 48.4 g of a compound K-2 (a yield of 76%).

LC-Mass (a theoretical value: 302.75 g/mol, a measured value: M+=303.84 g/mol)

Synthesis of Intermediate K-4

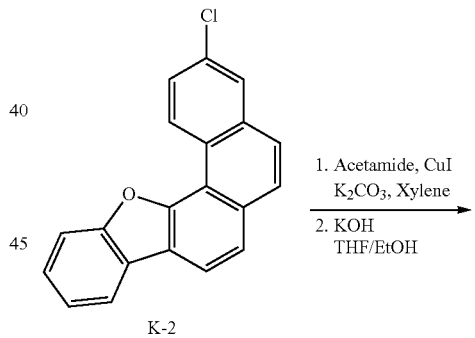

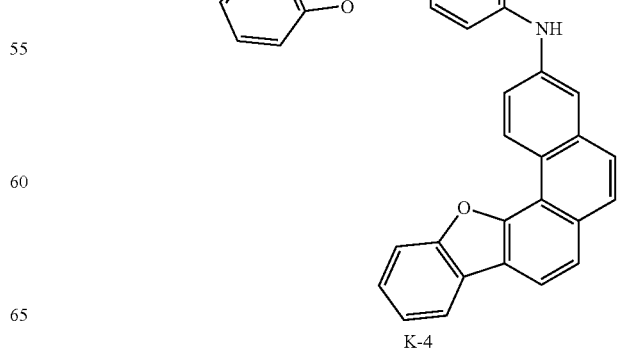

10 g (33.03 mmol) of the synthesized intermediate K-2, 1.74 g (14.86 mmol) of acetamide, and 8.21 g (59.45 mmol) of potassium carbonate were added to 130 ml of xylene and dissolved therein in a round-bottomed flask. 1.13 g (5.94 mmol) of copper iodide (I) and 1.04 g (11.8 mmol) of N,N-dimethylethylene diamine were sequentially added thereto and agitated under a nitrogen atmosphere for 4 days. When the reaction was terminated, the resultant was extracted with toluene and distilled water, and the extracted organic layer was dried with magnesium sulfate, filtered, and concentrated under a reduced pressure. The product was recrystallized with toluene and dried, and 6 g (10.14 mmol) of the synthesized material and 4.59 g (30.42 mmol) of potassium hydroxide were added to 80 ml of tetrahydrofuran and 80 ml of ethanol and dissolved therein in a round-bottomed flask. The resultant was refluxed and agitated under a nitrogen atmosphere for 12 hours. When the reaction was terminated, the resultant was concentrated under reduced pressure, extracted with dichloromethane and distilled water and the extracted organic layer was dried with magnesium sulfate, filtered, and concentrated under reduced pressure. The resultant was recrystallized with toluene, obtaining 5 g of the compound K-4 (a yield of 61%).

Synthesis of Intermediate K-5

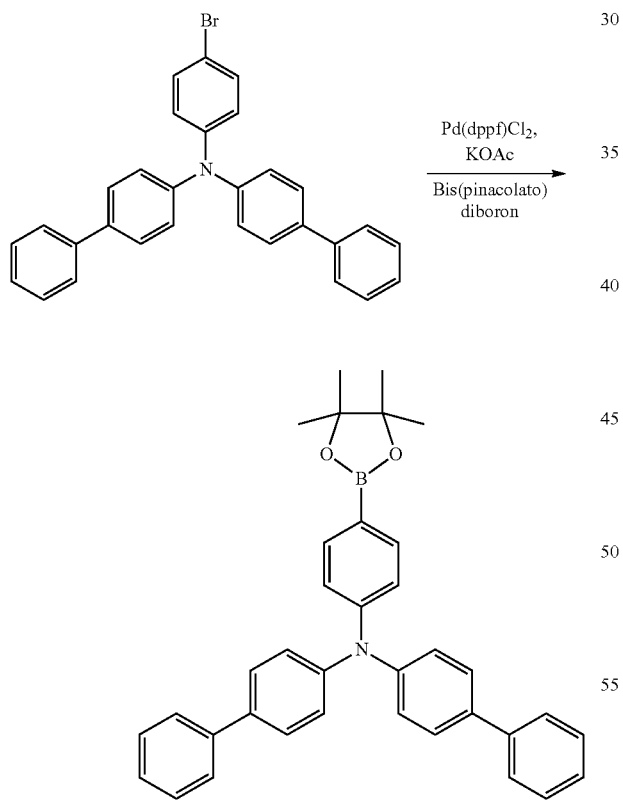

20 g (476.41 mmol) of N-(4-bromophenyl)-N,N-bis(1,1'-biphenyl-4-yl)amine and 1.03 g (1.26 mmol) of Pd(dppf)Cl$_2$, 12.8 g (50.38 mmol) of bis(pinacolato)diboron, and 12.36 g (125.94 mmol) of potassium acetate were suspended in 210 ml of toluene in a round-bottomed flask and refluxed and agitated for 12 hours. When the reaction was terminated, the resultant was cooled to room temperature, and filtered with a silica gel and concentrated. The resultant was recrystallized with acetone, obtaining 17 g of compound K-5 (a yield of 77%).

Synthesis of Intermediate K-2-1

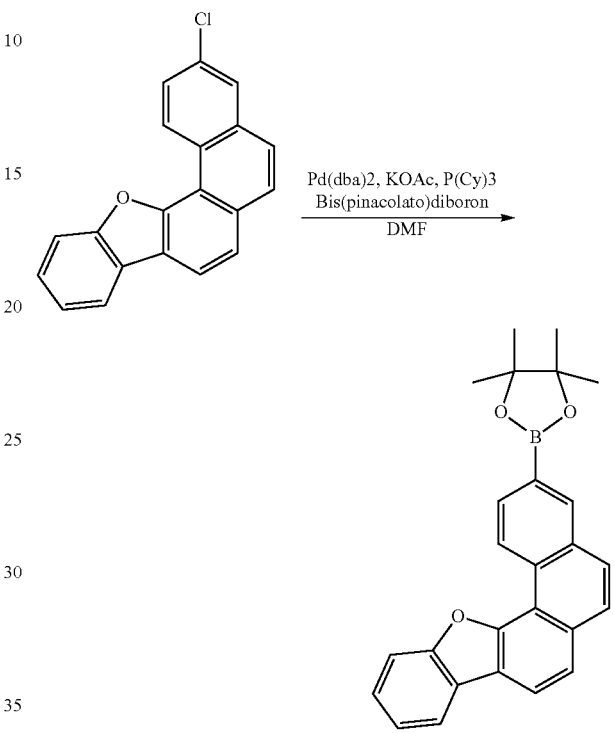

11 g (36.33 mmol) of the synthesized compound K-2, 1.25 g (2.18 mmol) of Pd(dba)$_2$, 10.7 g (109.00 mmol) of KOAc, 2.45 g (8.72 mmol) of P(Cy)3, and 11.07 g (43.60 mmol) of bis(pinacolato)diboron were suspend in 150 ml of DMF in a round-bottomed flask, and refluxed and agitated for 12 hours. When the reaction was terminated, the resultant was cooled to room temperature, 300 ml of distilled water was added and the resultant was agitated for 1 hour. During agitation, the produced solid was filtered and was washed with methanol, heat-dissolved in 300 ml of toluene, filtered with silica gel, and the filtered solution was concentrated and recrystallized with toluene, obtaining 9.05 g of a compound K-2-1 (a yield of 63%).

Synthesis of Intermediate K-6

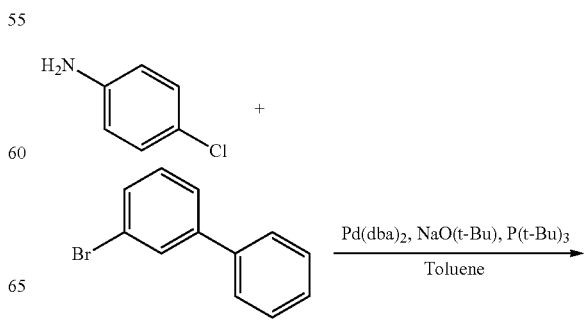

-continued

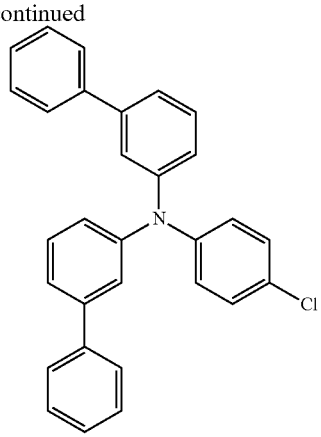

15 g (117.58 mmol) of 4-chloroaniline, 65.78 g (282.20 mmol) of 3-bromobiphenyl, 3.38 g (5.88 mmol) of Pd(dba)2, 2.38 g (11.76 mmol) of P(t-Bu)3, and 33.9 g of NaO(t-Bu) were suspended in 500 ml of toluene in a round-bottomed flask, and refluxed and agitated for 12 hours. When the reaction was terminated, distilled water was added, the resultant was agitated for 30 minutes, and an extracted organic layer was columned with silica gel column (hexane/dichloromethane=9:1 (v/v)), obtaining 31 g of a compound K-6 (a yield of 61%).

Synthesis of Intermediate K-7

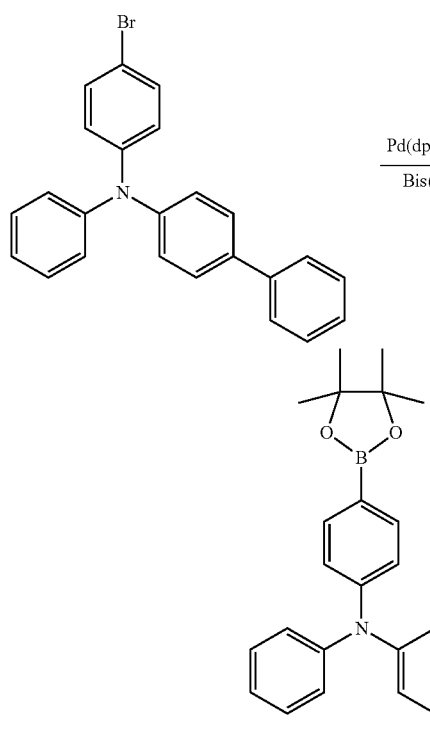

20 g (49.96 mmol) of N-(4-bromophenyl)-N-phenylbiphenyl-4-amine, 1.22 g (1.50 mmol) of Pd(dppf)Cl₂, 15.22 g (59.95 mmol) of bis(pinacolato)diboron, and 14.71 g (149.88 mmol) of potassium acetate were suspended in 250 ml of toluene in a round-bottomed flask, and refluxed and agitated for 12 hours. When the reaction was terminated, the resultant was cooled to room temperature, and a filtered solution was filtered by silica gel, and concentrated. The resultant was recrystallized with acetone, obtaining 7.18 g of a compound K-7 (a yield of 81%).

Synthesis of Intermediate K-8

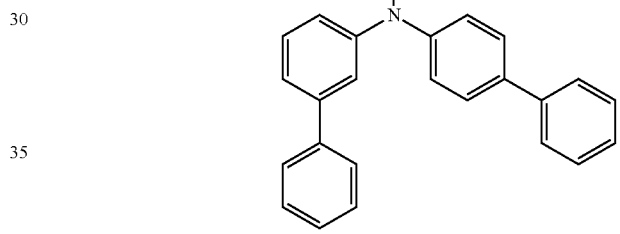

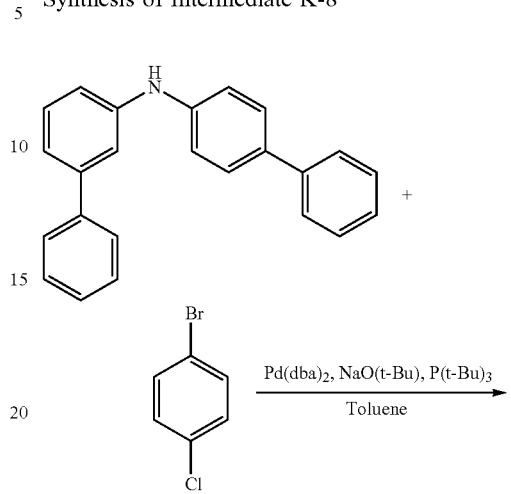

22.96 g (71.43 mmol) of N-(biphenyl-3-yl)biphenyl-4-amine, 1.23 g (2.14 mmol) of Pd(dba)2, 0.43 g (2.14 mmol) of P(t-Bu)3, and 10.29 g (107.15 mmol) of NaO(t-Bu) were suspend in 500 ml of DMF at 60° C. in a round-bottomed flask, and refluxed and agitated for 12 hours. When the reaction was terminated, distilled water was added, the resultant was agitated for 30 minutes, and an extracted organic layer was columned with silica gel (hexane/dichloromethane=9:1 (v/v)), obtaining 24 g of a compound K-8 (a yield of 78%).

Synthesis of Organic Compound

Synthesis Example 1: Synthesis of Compound A-1

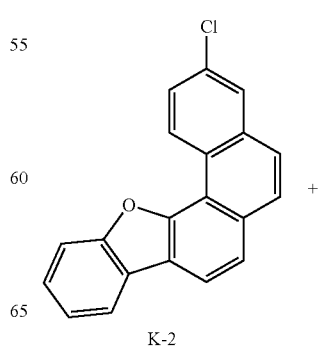

K-2

-continued

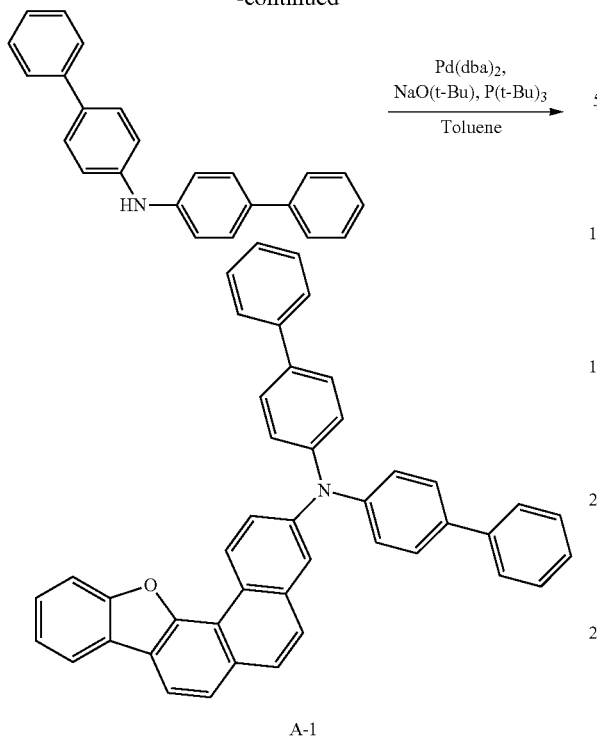

A-1

-continued

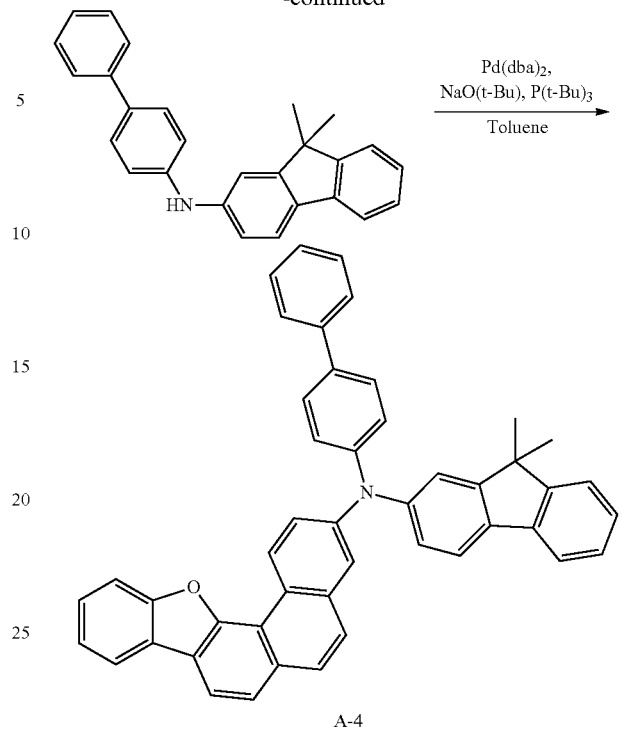

A-4

9.8 g (32.34 mmol) of the compound, 10.4 g (32.34 mmol) of K-2 bis(4-biphenyl)amine and 6.22 g (64.67 mmol) of sodium t-butoxide were put in a round-bottomed flask and dissolved in 160 ml of toluene. Next, 0.56 g (0.97 mmol) of di(dibenzylideneacetone)palladium (0) Pd(dba)$_2$) and 0.4 g (1.94 mmol) of tri-t-butylphosphine were sequentially added thereto, and the mixture was refluxed and agitated under a nitrogen atmosphere for 12 hours. When the reaction was terminated, the resultant was extracted with toluene and distilled water, and an organic layer obtained therefrom was dried with magnesium sulfate and filtered and then, concentrated under reduced pressure. Then, 200 ml of acetone was added to the concentrated solution, and a solid produced therein was filtered and recrystallized with methylene chloride, obtaining 13.0 g of a compound A-1 (a yield of 68%).

LC-Mass (a theoretical value: 587.71 g/mol, a measured value: M+=587.95 g/mol)

Synthesis Example 2: Synthesis of Compound A-4

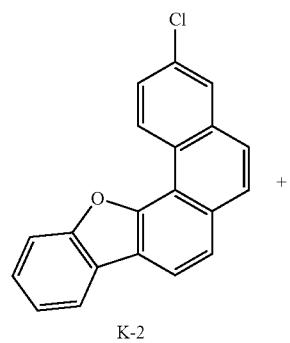

K-2

10 g (33.03 mmol) of the compound K-2, 11.94 g (33.03 mmol) of biphenyl-4-yl-(9,9-dimethyl-9H-fluoren-2-yl)-amine, and 6.35 g (66.06 mmol) of sodium t-butoxide were put in a round-bottomed flask and dissolved in 160 ml of toluene. Then, 0.57 g (0.99 mmol) of Pd(dba)$_2$ and 0.4 g (1.98 mmol) of tri-t-butylphosphine were sequentially added thereto, and the mixture was refluxed and agitated under a nitrogen atmosphere for 12 hours. When the reaction was terminated, the resultant was extracted with toluene and distilled water, and an organic layer obtained therefrom was dried with magnesium sulfate and filtered and then, concentrated under a reduced pressure. Then, 200 ml of acetone was added to the concentrated solution, the mixture was agitated, and a solid produced therein was filtered and recrystallized with methylene chloride and ethylacetate, obtaining 15.3 g of a compound A-4 (a yield of 74%).

LC-Mass (a theoretical value: 627.77 g/mol, a measured value: M+=628.14 g/mol)

Synthesis Example 3: Synthesis of Compound B-2

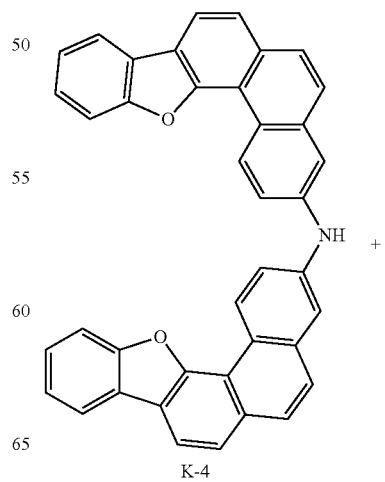

K-4

-continued

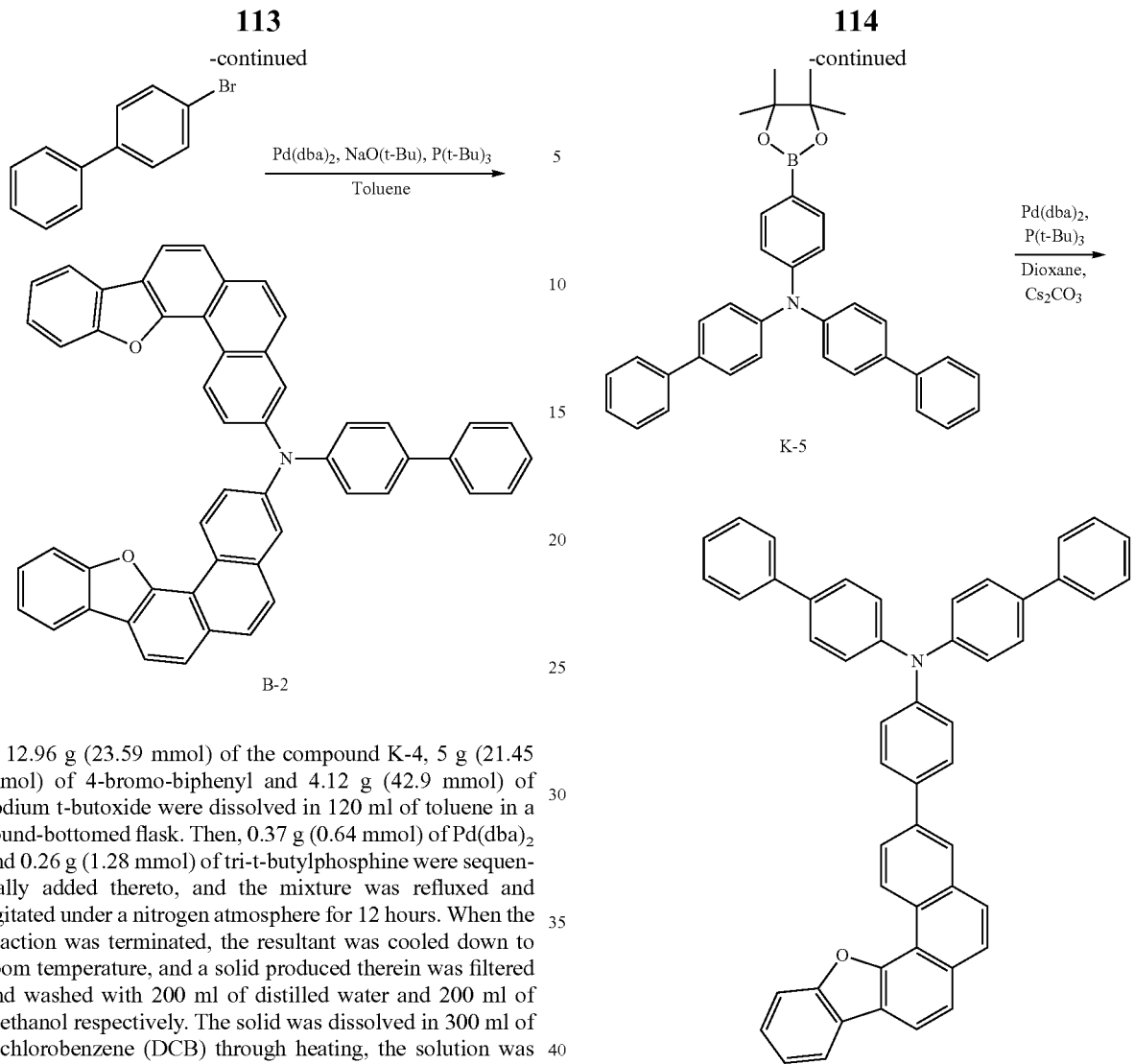

12.96 g (23.59 mmol) of the compound K-4, 5 g (21.45 mmol) of 4-bromo-biphenyl and 4.12 g (42.9 mmol) of sodium t-butoxide were dissolved in 120 ml of toluene in a round-bottomed flask. Then, 0.37 g (0.64 mmol) of $Pd(dba)_2$ and 0.26 g (1.28 mmol) of tri-t-butylphosphine were sequentially added thereto, and the mixture was refluxed and agitated under a nitrogen atmosphere for 12 hours. When the reaction was terminated, the resultant was cooled down to room temperature, and a solid produced therein was filtered and washed with 200 ml of distilled water and 200 ml of methanol respectively. The solid was dissolved in 300 ml of dichlorobenzene (DCB) through heating, the solution was filtered through silica gel, 300 ml of methanol was added thereto, and the mixture was agitated for one hour. Then, a solid produced therein was filtered and washed with 200 ml of acetone, obtaining 14.4 g of a compound B-2 (a yield of 87%).

LC-Mass (a theoretical value: 701.81 g/mol, a measured value: M+=701.94 g/mol)

Synthesis Example 4: Synthesis of Compound A-26

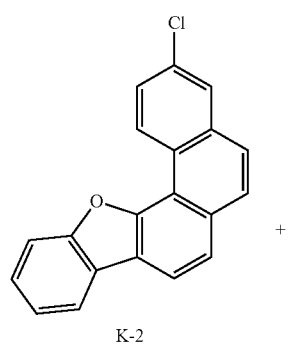

15 g (49.55 mmol) of the compound K-2, 27.2 g (52.02 mmol) of the compound K-5, and 32.3 g (99.09 mmol) of cesium carbonate were added to a round-bottomed flask, and 250 ml of 1,4-dioxane was added and dissolved. 0.85 g (1.49 mmol) of $Pd(dba)_2$ and 0.7 g (3.47 mmol) of tri-t-butylphosphine were sequentially added and refluxed and agitated under a nitrogen atmosphere for 12 hours. When the reaction was terminated, the resultant was cooled to room temperature, distilled water was added, the resultant was agitated for 30 minutes, the produced solid was filtered and was washed with each of 200 ml of distilled water and methanol. The solid was heat-dissolved in 300 ml of dichlorobenzene (DCB), filtered with silica gel, 300 ml of methanol was added and the resultant was agitated for 1 hour. The produced solid was filtered and washed with 200 ml of acetone, obtaining 17.2 g of the compound A-26 (a yield of 52%).

LC-Mass (a theoretical value: 663.8 g/mol, a measured value: M+=663.4 g/mol)

Synthesis Example 5: Synthesis of Compound A-38

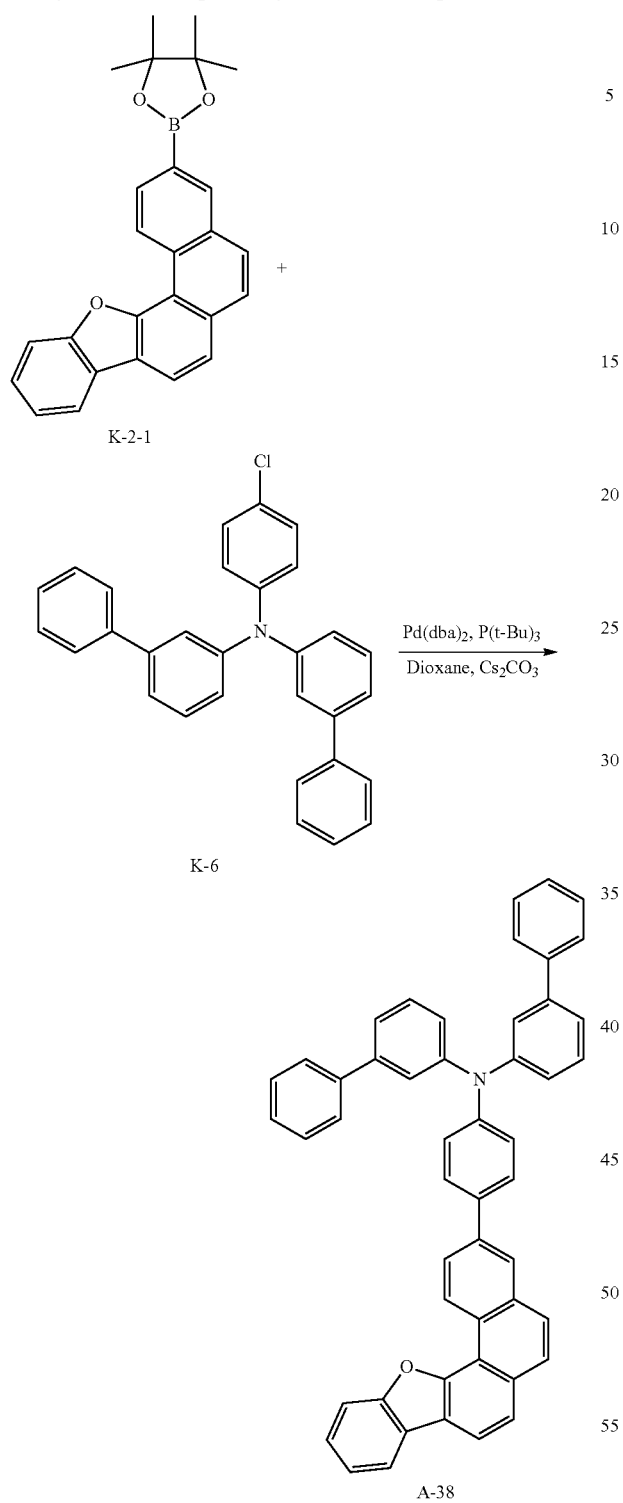

9.05 g (22.95 mmol) of the synthesized compound K-2-1, 9.92 g (22.95 mmol) of the compound K-6 and 14.96 g (45.91 mmol) of cesium carbonate were added to 150 ml of 1,4-dioxane and dissolved in a round-bottomed flask. 0.4 g (0.69 mmol) of Pd(dba)$_2$ and 0.33 g (1.61 mmol) of tri-t-butylphosphine were sequentially added and refluxed and agitated under a nitrogen atmosphere for 12 hours. When the reaction was terminated, the resultant was cooled to room temperature, distilled water was added, the resultant was agitated for 30 minutes, the produced solid was filtered and was washed with each of 200 ml of distilled water and methanol. The solid was heat-dissolved in 300 ml of toluene (DCB), filtered with silica gel, and recrystallized with acetone, obtaining 11.28 g of the target compound, the compound A-38 (a yield of 74 OA).

LC-Mass (a theoretical value: 663.8 g/mol, a measured value: M+=663.9 g/mol)

Synthesis Example 6: Synthesis of Compound A-111

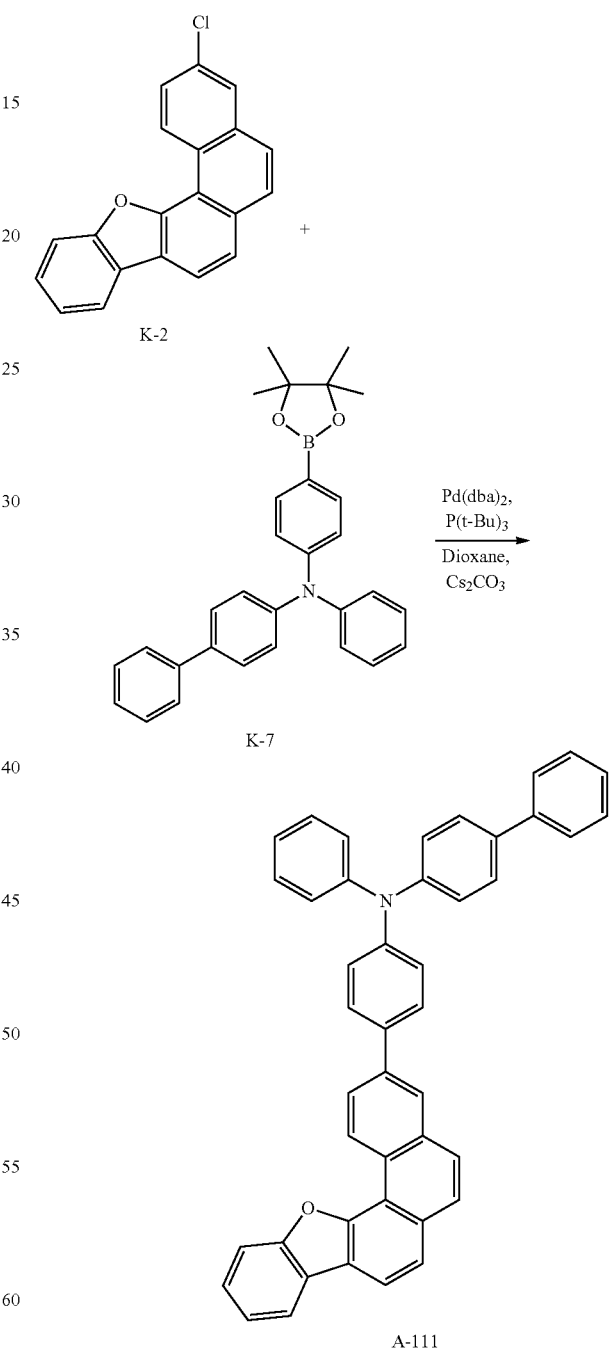

10 g (33.03 mmol) of the compound K-2, 14.77 g (33.03 mmol) of compound K-7, and 21.52 g (66.06 mmol) of cesium carbonate were added to 200 ml of 1,4-dioxane and dissolved in a round-bottomed flask. 0.57 g (0.99 mmol) of Pd(dba)$_2$ and 0.4 g (1.98 mmol) of tri-t-butylphosphine were sequentially added and refluxed and agitated under a nitrogen atmosphere for 12 hours. When the reaction was terminated, the resultant was cooled to room temperature, distilled water was added, the resultant was agitated for 30 minutes, the produced solid was filtered and was washed with each of 200 ml of distilled water and methanol. The solid was heat-dissolved in 300 ml of toluene (DCB), filtered with silica gel, and recrystallized with acetone, obtaining 11.28 g of the target compound, the compound A-111 (a yield of 56%).

LC-Mass (a theoretical value: 587.7 g/mol, a measured value: M+=587.4 g/mol)

Synthesis Example 7: Synthesis of Compound A-112

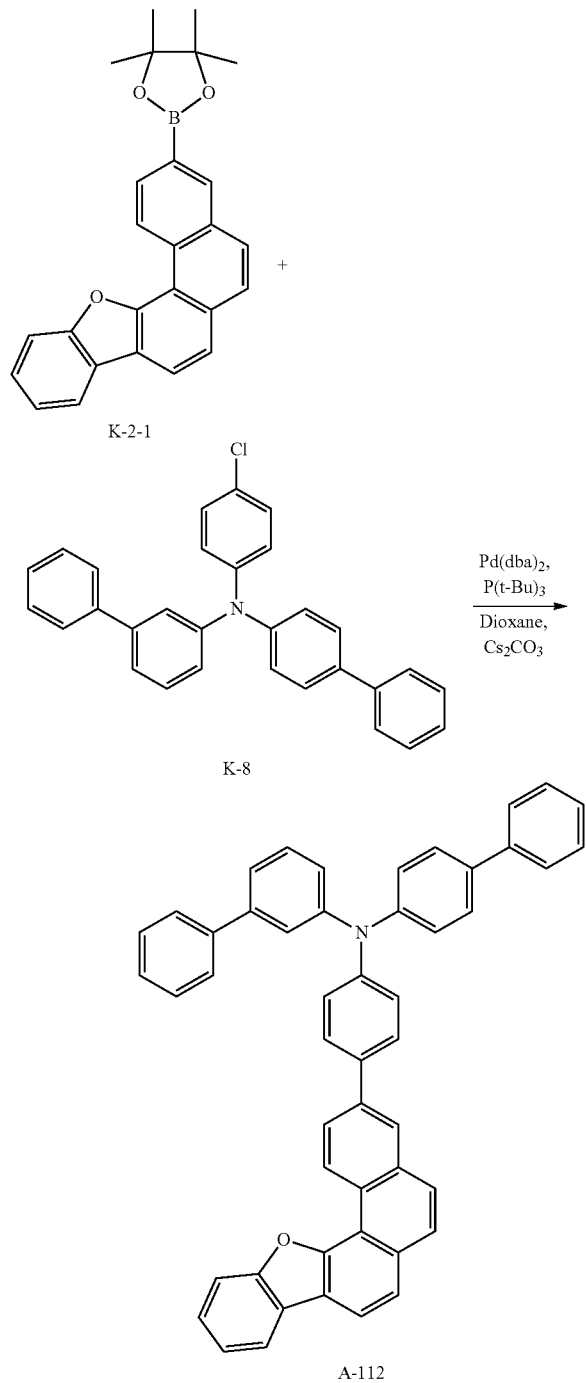

9.27 g (23.51 mmol) of the compound K-2-1, 10.16 g (23.51 mmol) of compound K-8 and cesium carbonate 15.32 g (47.02 mmol) were added to 150 ml of 1,4-dioxane and dissolved in a round-bottomed flask. 0.41 g (0.71 mmol) of Pd(dba)$_2$ and 0.33 g (1.65 mmol) of tri-t-butylphosphine were sequentially added and refluxed and agitated under a nitrogen atmosphere for 12 hours. When the reaction was terminated, the resultant was cooled to room temperature, distilled water was added, the resultant was agitated for 30 minutes, the produced solid was filtered and was washed with each of 200 ml of distilled water and methanol. The solid was heat-dissolved in 300 ml of toluene (DCB), and adsorption-columned with silica gel, obtaining 8.1 g of the target compound, the compound A-112 (a yield of 52%).

LC-Mass (a theoretical value: 663.8 g/mol, a measured value: M+=663.2 g/mol)

Manufacture of Organic Light Emitting Diode

Example 1

ITO (indium tin oxide) was coated to be 1500 Å thick on a glass substrate, and the coated glass was ultrasonic wave-washed with distilled water. After washing with distilled water, the washed glass substrate was ultrasonic wave-washed with a solvent such as isopropyl alcohol, acetone, methanol, and the like, and was moved to a plasma cleaner to clean the substrate by using oxygen plasma for 5 minutes and moved to a vacuum depositor. This ITO transparent electrode was used as an anode, 4,4'-bis[N-[4-{N,N-bis(3-methylphenyl)amino}-phenyl]-N-phenylamino]biphenyl (DNTPD) was vacuum-deposited on an ITO substrate to form a 600 Å-thick hole injection layer (HIL). Subsequently, the compound represented by Chemical Formula J-9 was vacuum-deposited to form a 250 Å-thick first hole transport layer (1-HTL) and then the compound A-1 synthesized in the Synthesis Example 1 was vacuum-deposited to form a 50 Å-thick second hole transport layer (2-HTL). On the hole transport layer (HTL), 9,10-di-(2-naphthyl)anthracene (ADN) was used as a host and 3 wt % of 2,5,8,11-tetra(tert-butyl)perylene (TBPe) was doped by vacuum deposition to form a 250 Å-thick emission layer.

Subsequently, on the emission layer, Alq3 was vacuum-deposited to form a 250 Å-thick electron transport layer (ETL). On the electron transport layer (ETL), 10 Å LiF and 1000 Å Al were sequentially vacuum-deposited to form a cathode, manufacturing an organic light emitting diode.

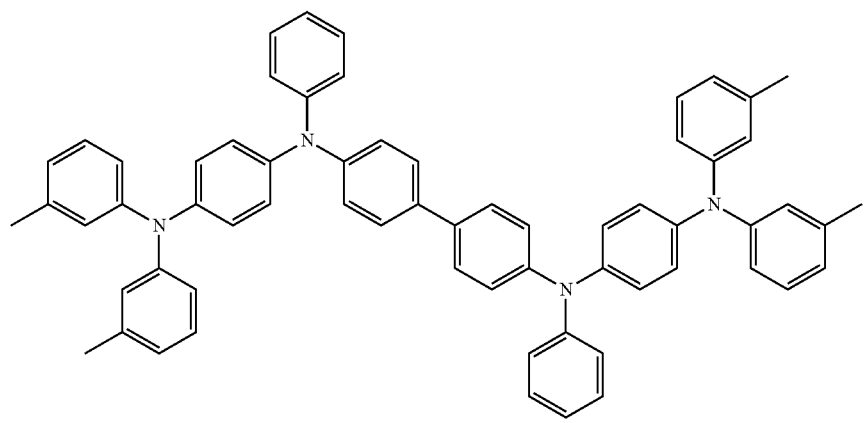

[DNTPD]

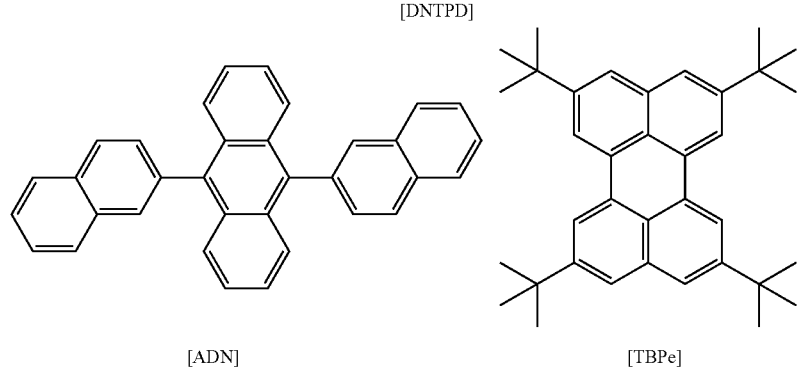

[ADN]  [TBPe]

Example 2

An organic light emitting diode was manufactured according to the same method as Example 1 except for forming a second hole transport layer (2-HTL) by using the compound A-4 of Synthesis Example 2 instead of the compound A-1 of Synthesis Example 1.

Example 3

An organic light emitting diode was manufactured according to the same method as Example 1 except for forming a second hole transport layer (2-HTL) by using the compound B-2 of Synthesis Example 3 instead of the compound A-1 of Synthesis Example 1.

Example 4

An organic light emitting diode was manufactured according to the same method as Example 1 except for forming a second hole transport layer (HTL) by using the compound A-26 of Synthesis Example 4 instead of the compound A-1 of Synthesis Example 1.

Example 5

An organic light emitting diode was manufactured according to the same method as Example 1 except for forming a second hole transport layer (HTL) by using the compound A-38 of Synthesis Example 5 instead of the compound A-1 of Synthesis Example 1.

Example 6

An organic light emitting diode was manufactured according to the same method as Example 1 except for forming a second hole transport layer (HTL) by using the compound A-111 of Synthesis Example 6 instead of the compound A-1 of Synthesis Example 1.

Example 7

An organic light emitting diode was manufactured according to the same method as Example 1 except for forming a second hole transport layer (HTL) by using the compound A-112 of Synthesis Example 7 instead of the compound A-1 of Synthesis Example 1.

Comparative Example 1

An organic light emitting diode was manufactured according to the same method as Example 1 except for forming a 300 Å-thick first hole transport layer (HTL) without forming the second hole transport layer (2-HTL).

Evaluation

Current density and luminance changes depending on a voltage and luminous efficiency of each organic light emitting diode according to Examples 1 to 7 and Comparative Example 1 were measured.

The measurements were specifically performed in the following method, and the results were provided in the following Table 2.

(1) Measurement of Current Density Change Depending on Voltage Change

Current values in the unit device of the manufactured organic light emitting diodes were measured, while the voltage was increased from 0 V to 10 V using a current-voltage meter (Keithley 2400), and the measured current values were divided by an area to provide the results.

(2) Measurement of Luminance Change Depending on Voltage Change

Luminance of the manufactured organic light emitting diodes was measured, while the voltage was increased from 0 V to 10 V using a luminance meter (Minolta Cs-1000A).

(3) Measurement of Current Efficiency

Current efficiencies (cd/A) at the same current density (10 mA/cm$^2$) were calculated by using the luminance, current density, and voltages (V) from items (1) and (2).

TABLE 2

| Devices | Compound used in second hole transport layer (HTL) | Driving voltage (V) | Color (EL color) | Efficiency (cd/A) | Half-life life-span (h) @ 1000 cd/m$^2$ |
|---|---|---|---|---|---|
| Example 1 | A-1 | 6.1 | Blue | 6.5 | 2,030 |
| Example 2 | A-4 | 6.2 | Blue | 6.6 | 2,170 |
| Example 3 | B-2 | 6.1 | Blue | 6.4 | 1,840 |
| Example 4 | A-26 | 6.1 | Blue | 6.6 | 2,260 |
| Example 5 | A-38 | 6.1 | Blue | 6.8 | 1,570 |
| Example 6 | A-111 | 6.0 | Blue | 6.4 | 2,310 |
| Example 7 | A-112 | 6.1 | Blue | 6.5 | 1,790 |
| Comparative Example 1 | None | 6.4 | Blue | 5.9 | 1,380 |

*Current density: 10 mA/cm$^2$

Referring to Table 2, the organic light emitting diodes according to Examples 1 to 7 showed a lower driving voltage, and improved efficiency and life-span characteristics compared with the organic light emitting diode according to Comparative Example 1.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200, 300: organic light emitting diode
105: organic layer
110: cathode
120: anode
130: emission layer
140: hole transport layer
141: first hole transport layer
142: second hole transport layer

The invention claimed is:

1. An organic compound represented by the following Chemical Formula 1:

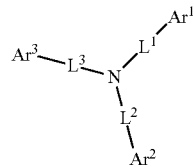

[Chemical Formula 1]

wherein, in Chemical Formula 1,
L$^1$ to L$^3$ are each independently a single bond or an unsubstituted C6 to C30 arylene group,
Ar$^1$ to Ar$^3$ are each independently a substituted or unsubstituted C6 to C30 aryl group, or a group represented by the following Chemical Formula A, and one or two of Ar$^1$ to Ar$^3$ is a group represented by the following Chemical Formula A,

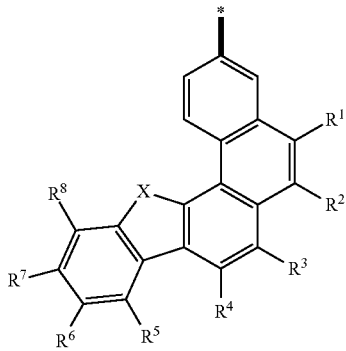

[Chemical Formula A]

wherein, in Chemical Formula A,
X is O or S,
R$^1$ to R$^8$ are each hydrogen, and
* indicates a linking point.

2. The organic compound of claim 1, wherein the organic compound is represented by one of the following Chemical Formulae 2-I, 3-I, and 4-I:

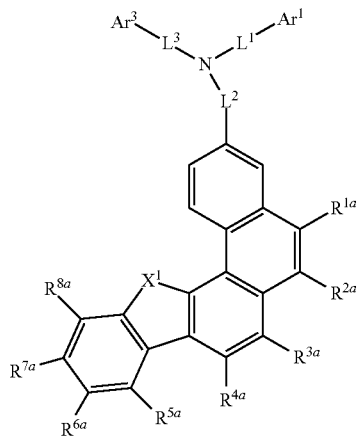

[Chemical Formula 2-I]

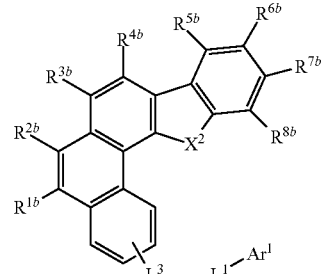

[Chemical Formula 3-I]

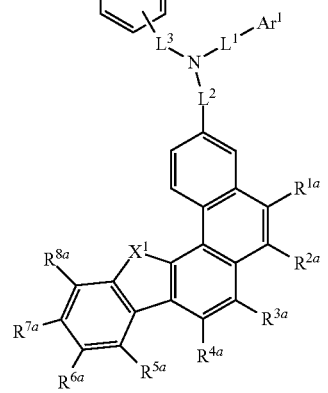

-continued

[Chemical Formula 4-I]

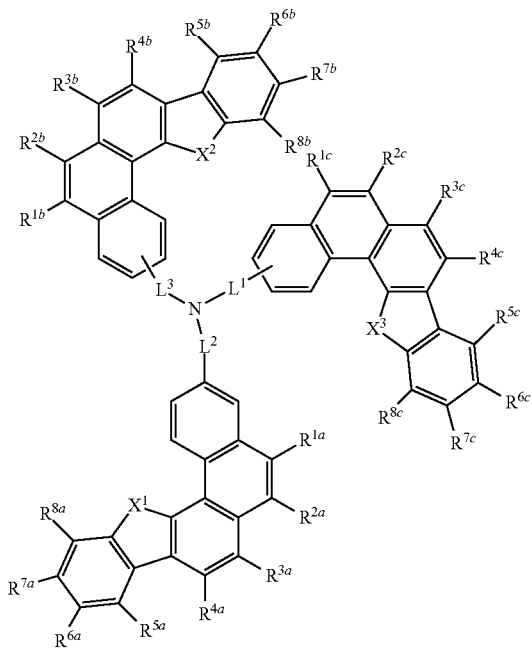

wherein, in the Chemical Formulae 2-I, 3-I, and 4-I, $X^1$ to $X^3$ are each independently O or S, $L^1$ to $L^3$ are each independently a single bond or an unsubstituted C6 to C30 arylene group, $Ar^1$ and $Ar^a$ are each independently a substituted or unsubstituted C6 to C30 aryl group, and $R^{1a}$ to $R^{8a}$, $R^{1b}$ to $R^{8b}$ and $R^{1c}$ to $R^{8c}$ are each hydrogen.

3. The organic compound of claim 1, wherein $Ar^1$ to $Ar^3$ are each independently groups listed in the following Group 1 or the group represented by Chemical Formula A, and one or two of $Ar^1$ to $Ar^3$ is the group represented by Chemical Formula A

[Group 1]

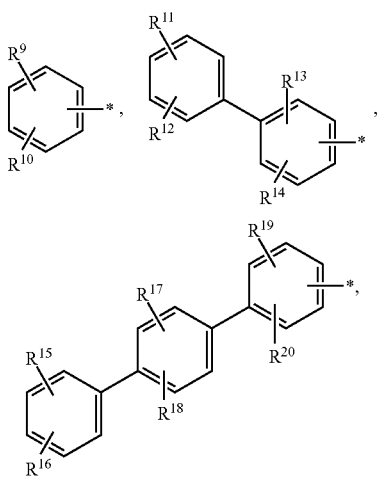

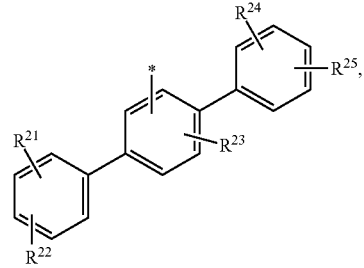

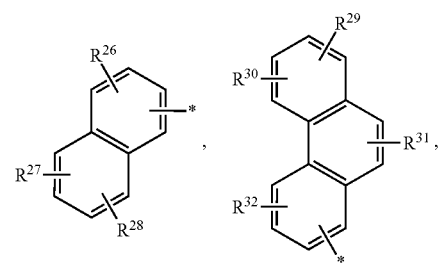

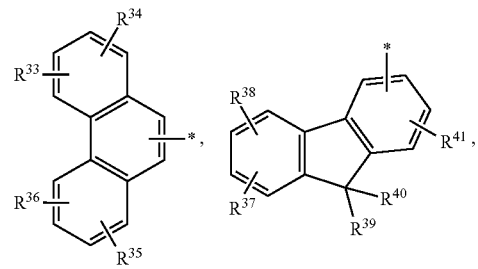

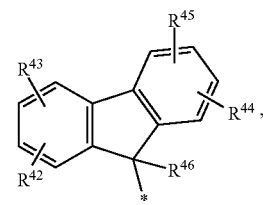

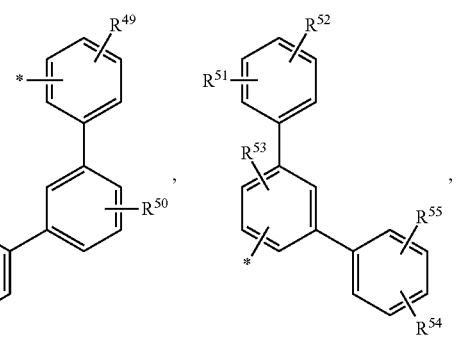

wherein, in Group 1, $R^9$ to $R^{70}$ are independently hydrogen or a C6 to C30 aryl group, and

* indicates a linking point.

4. An organic compound, wherein the organic compound is one of the compounds listed in the following Group 2:

[Group 2]
A-1
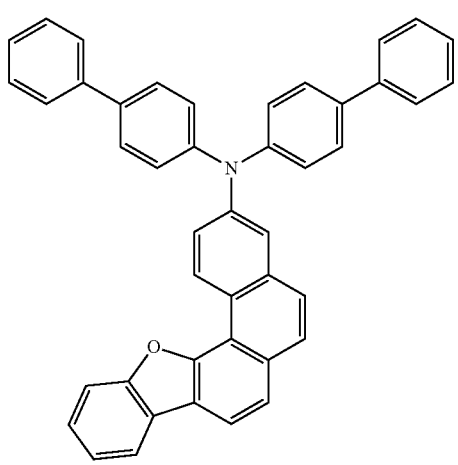
A-4
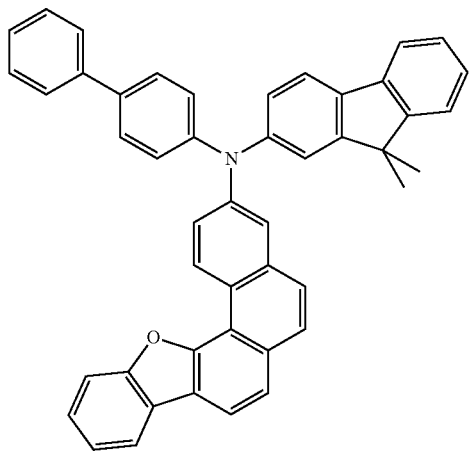
A-2
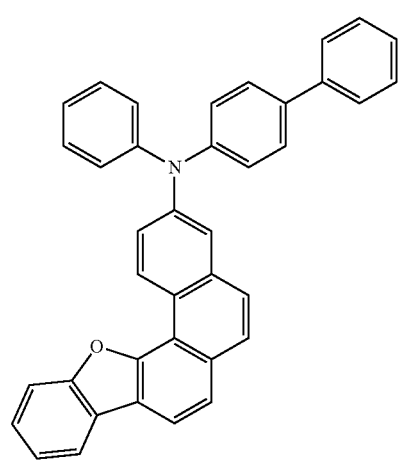
A-5
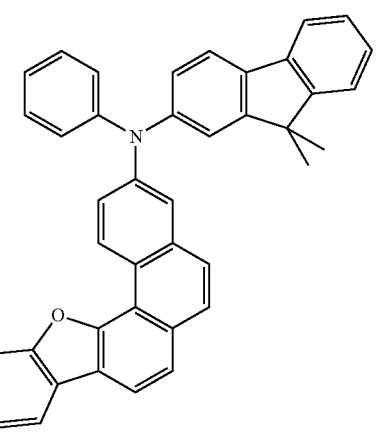
A-3
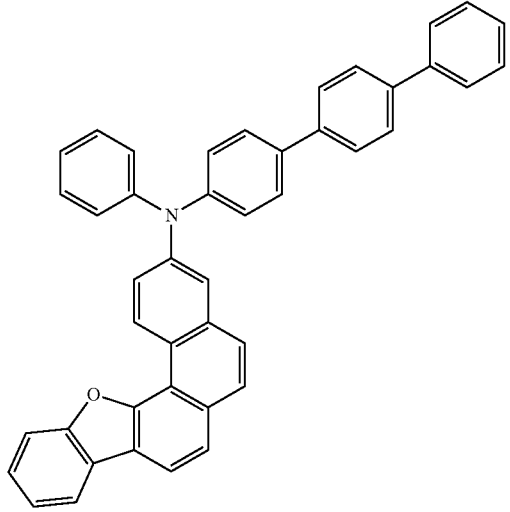
A-6
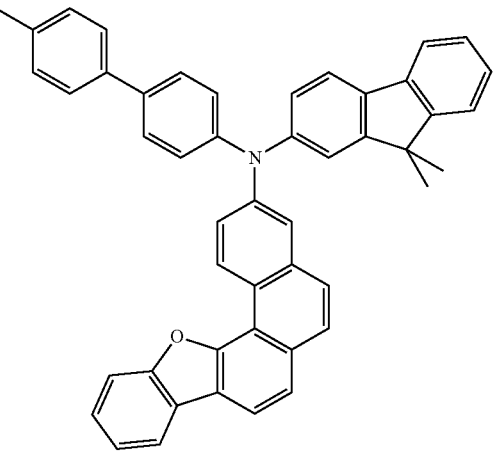

A-7
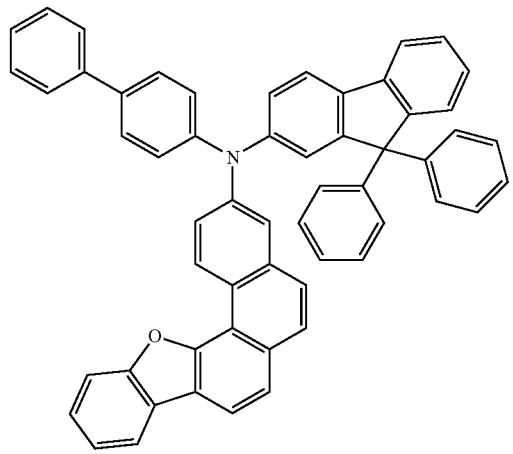
A-8
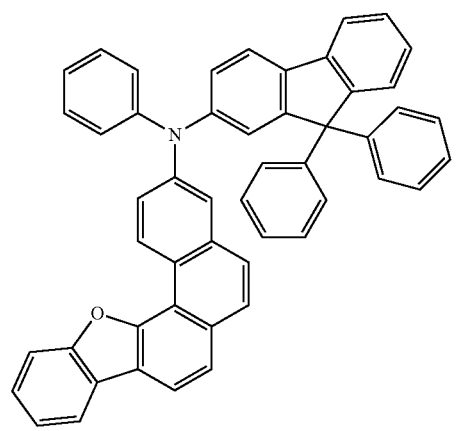
A-9
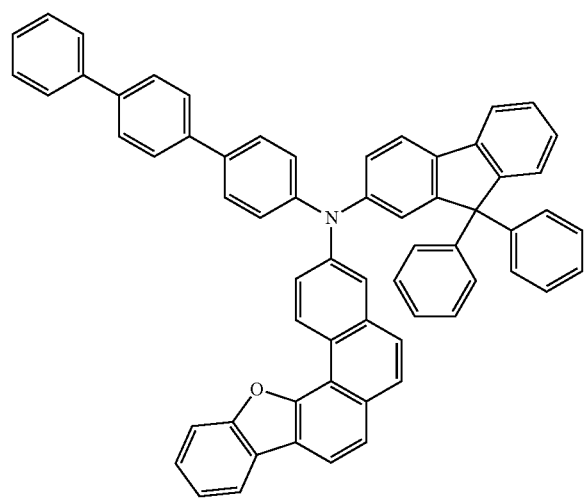
A-10
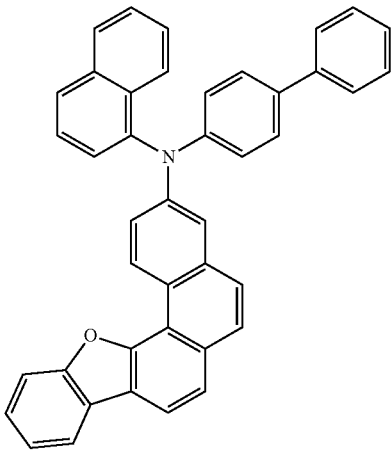
A-11
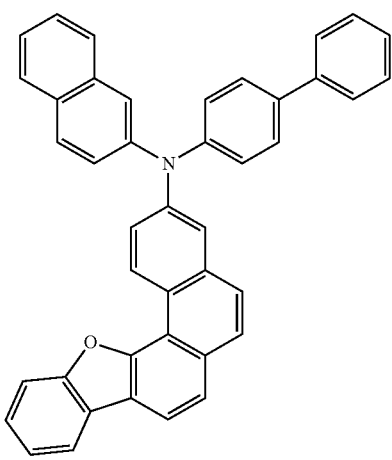
A-12
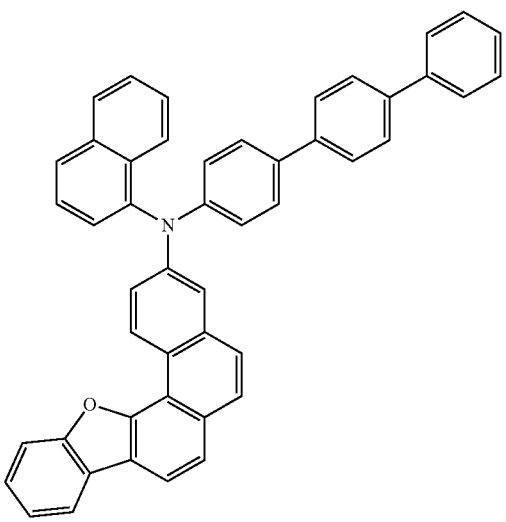

A-13
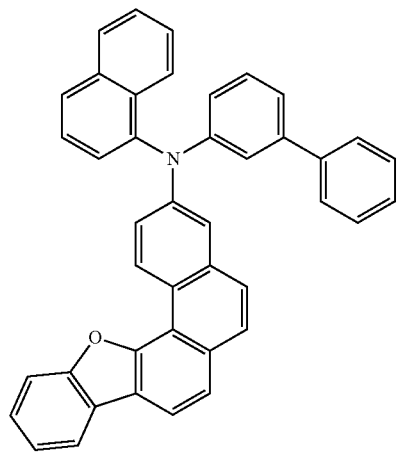
A-14
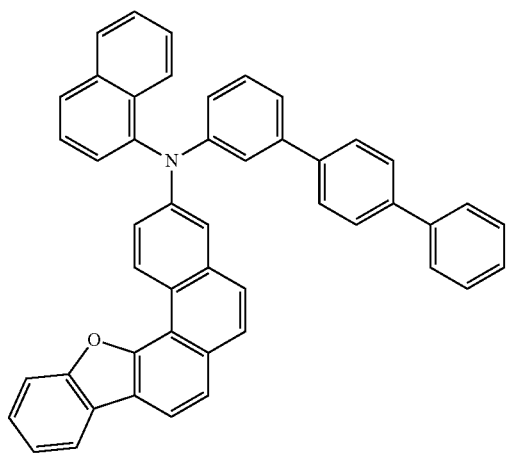
A-15
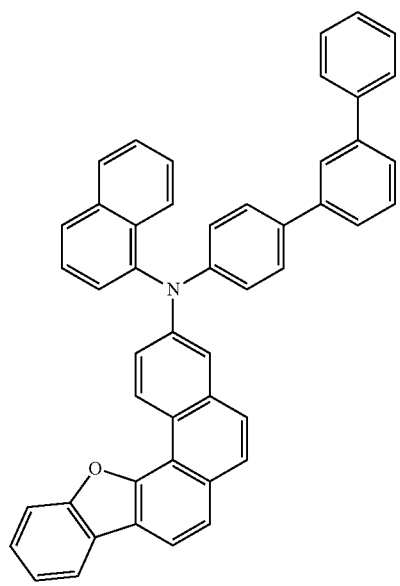
A-16
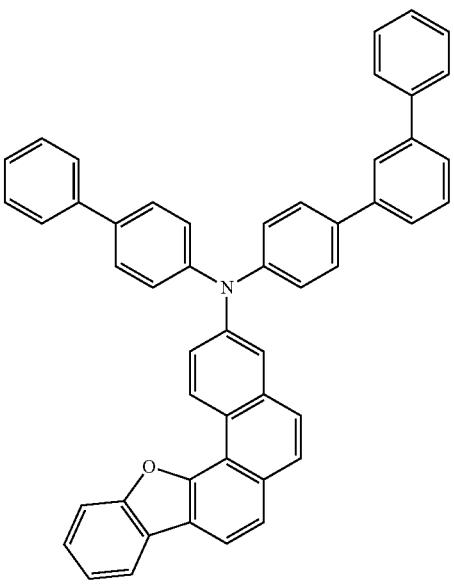
A-18
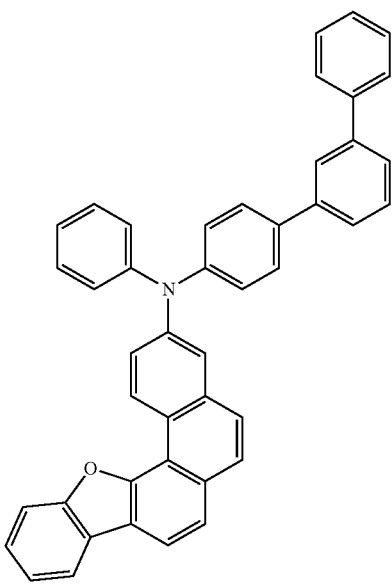

A-19
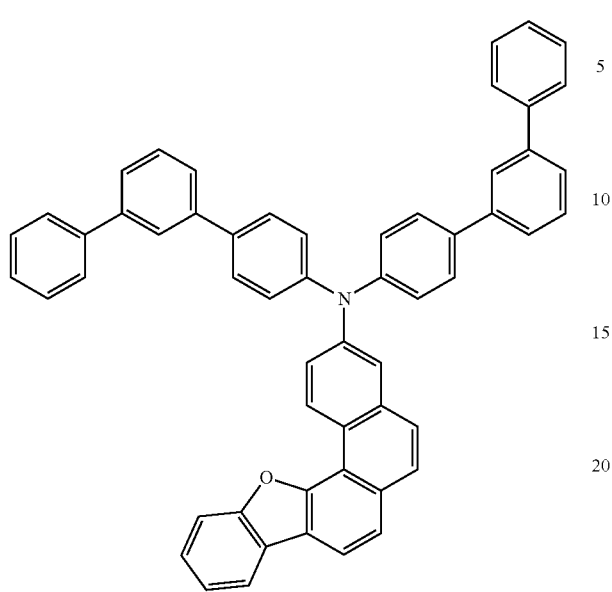
A-20
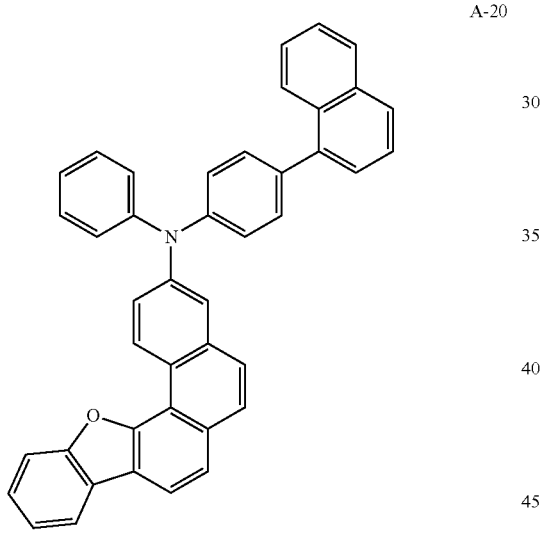
A-21
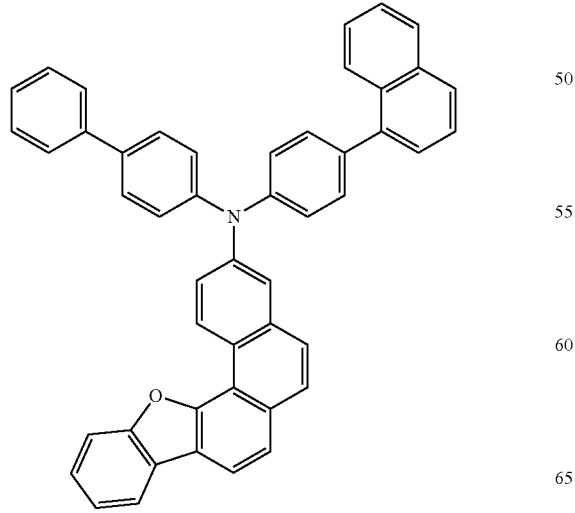
A-22
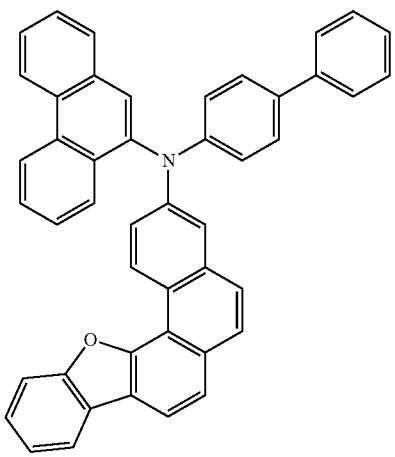
A-23
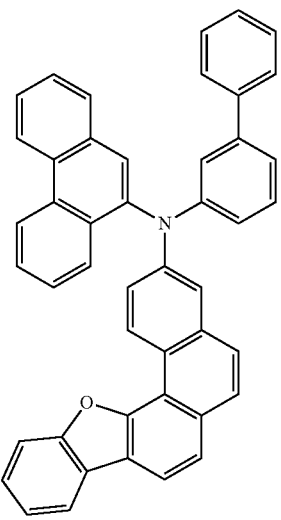
A-25
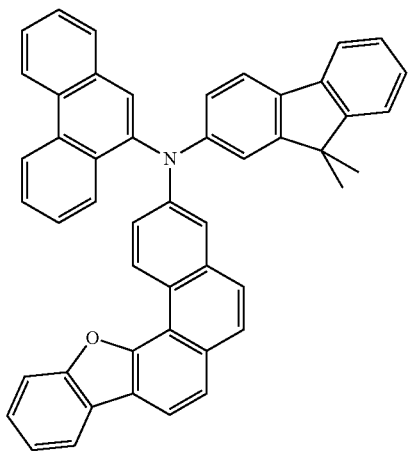

-continued
A-26
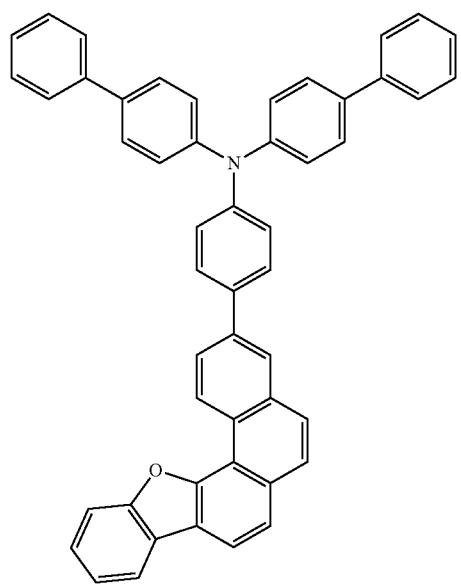
A-27
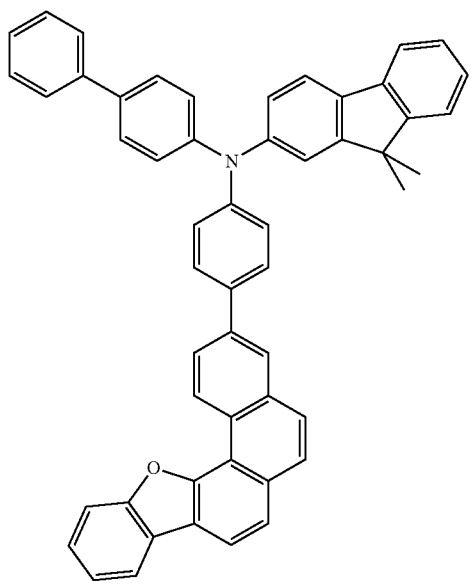
-continued
A-28
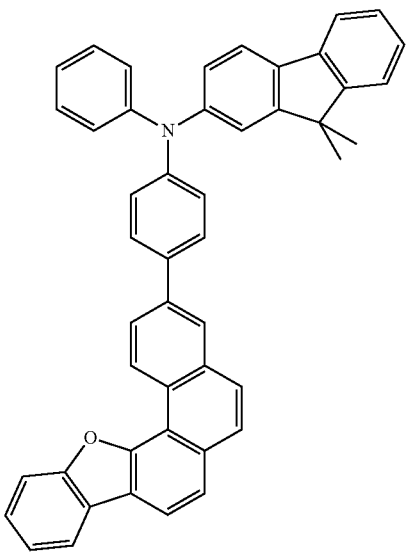
A-29
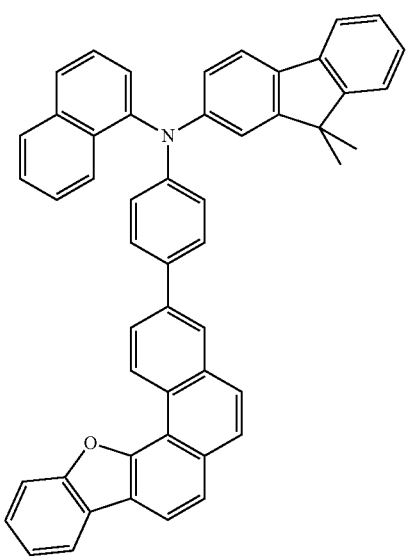
A-30
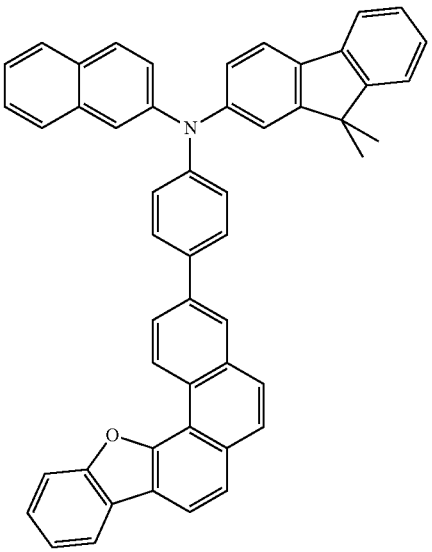

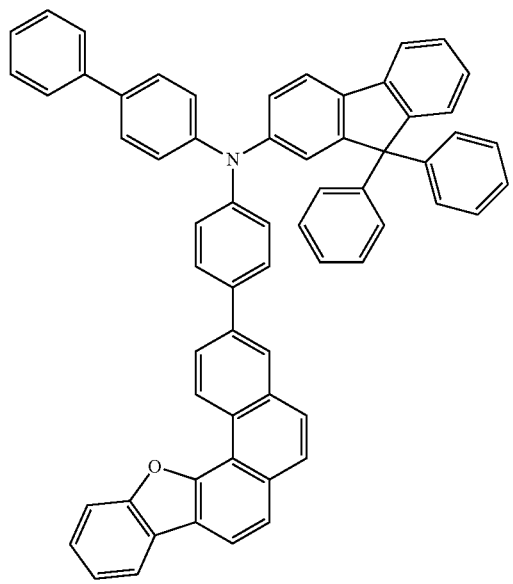
A-31
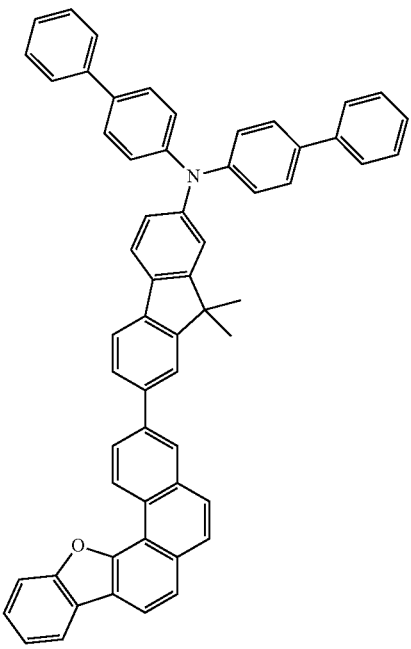
A-33
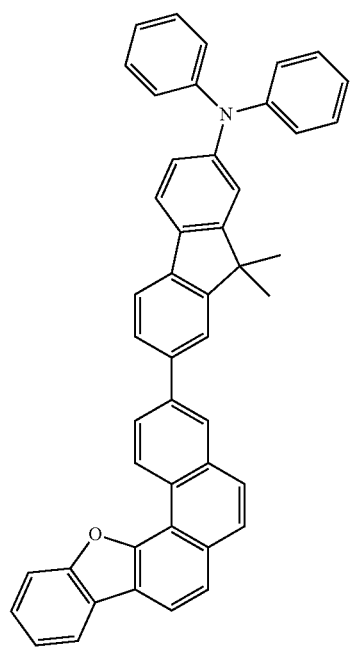
A-32
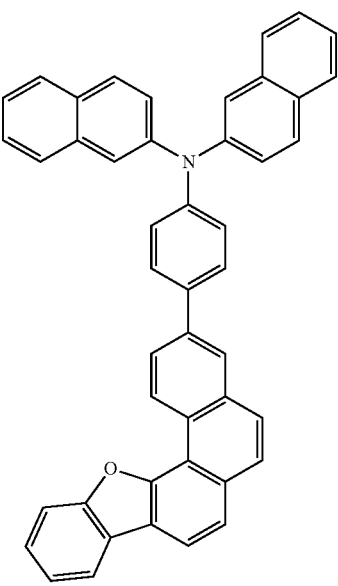
A-34

A-35
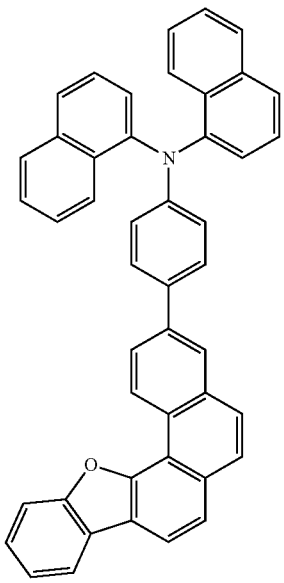
A-36
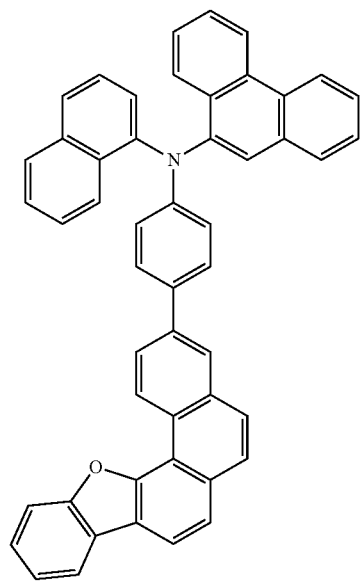
A-37
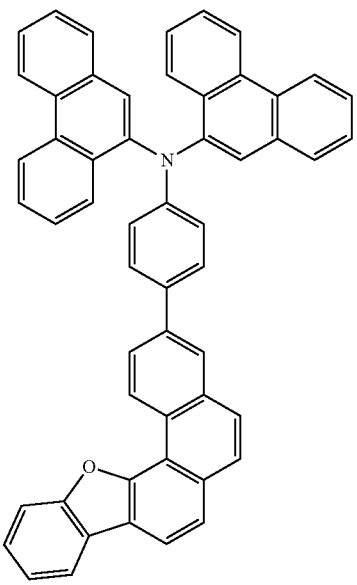
A-38
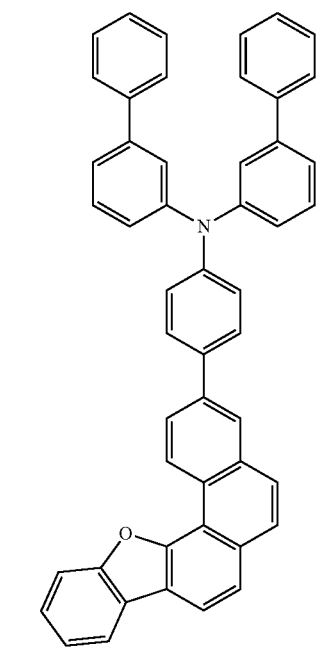

A-53
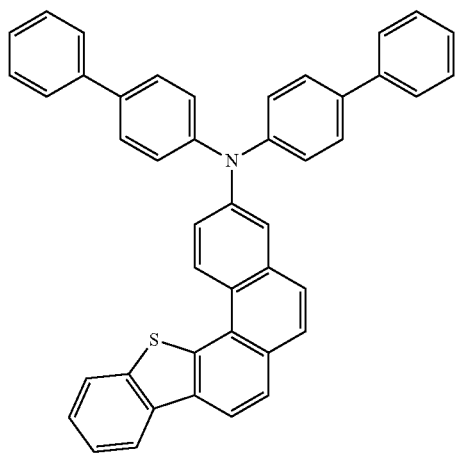
A-56
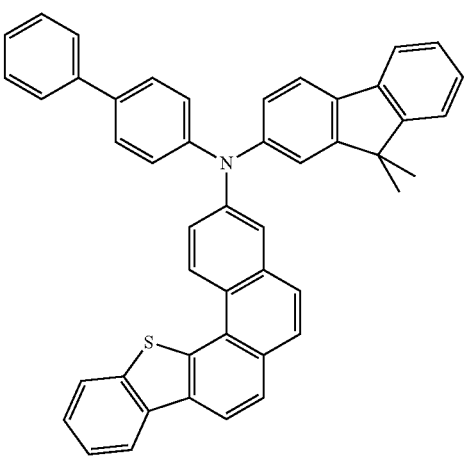
A-54
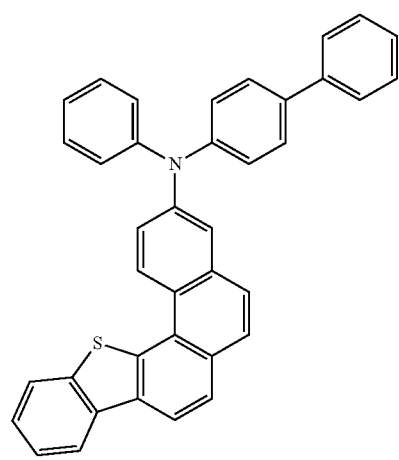
A-57
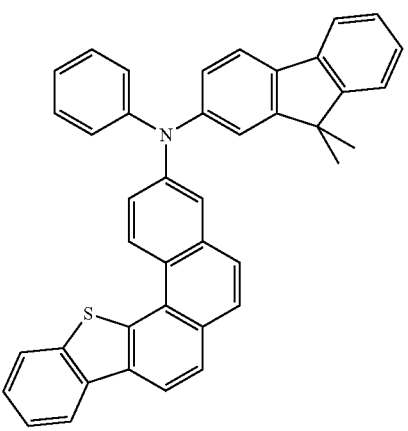
A-55
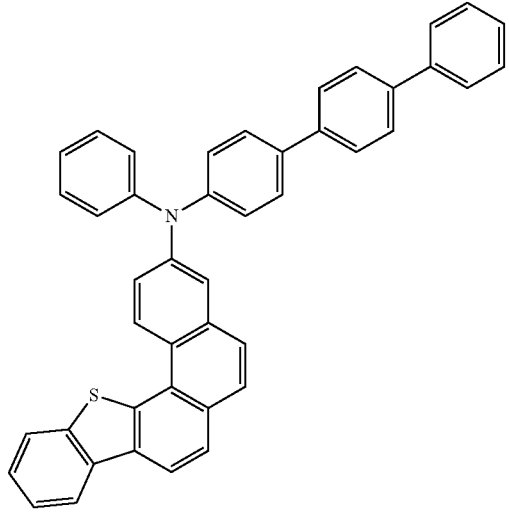
A-58
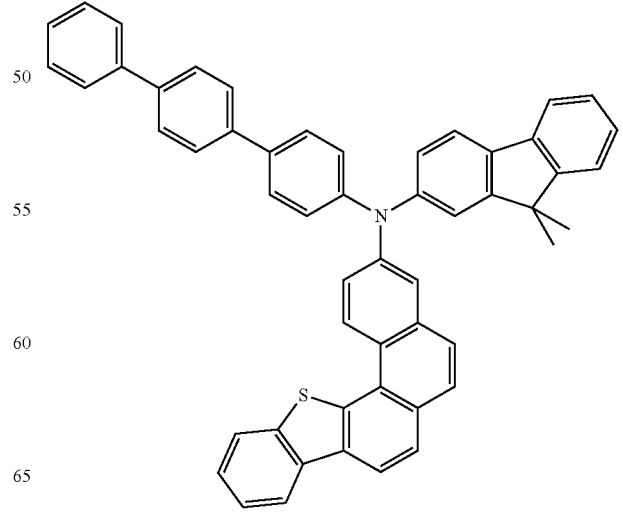

A-59
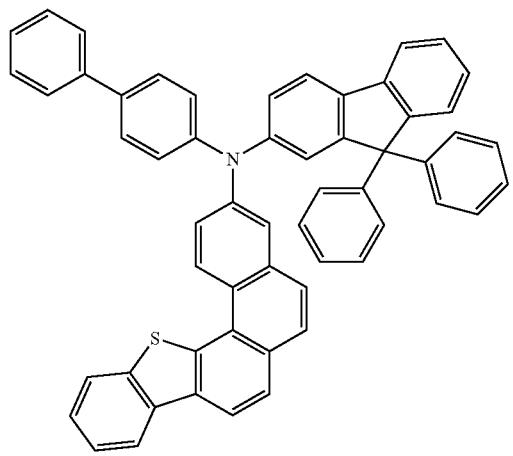
A-62
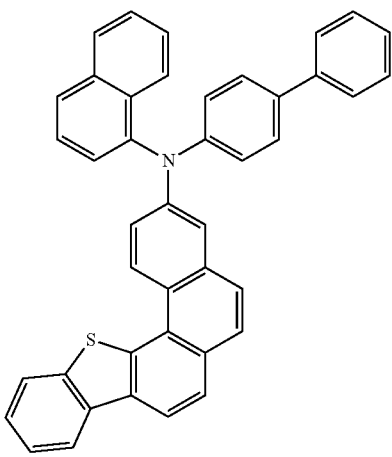
A-60
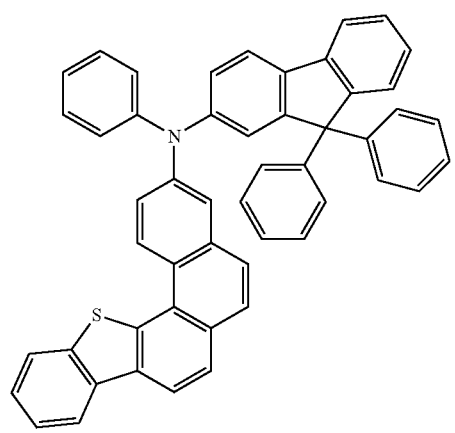
A-63
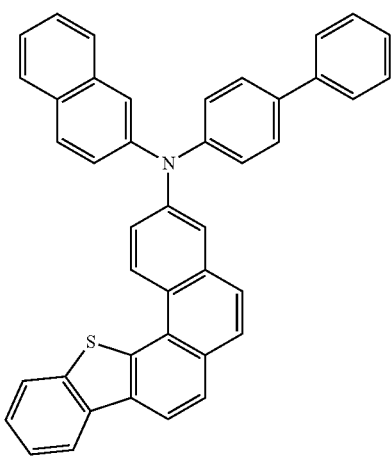
A-61
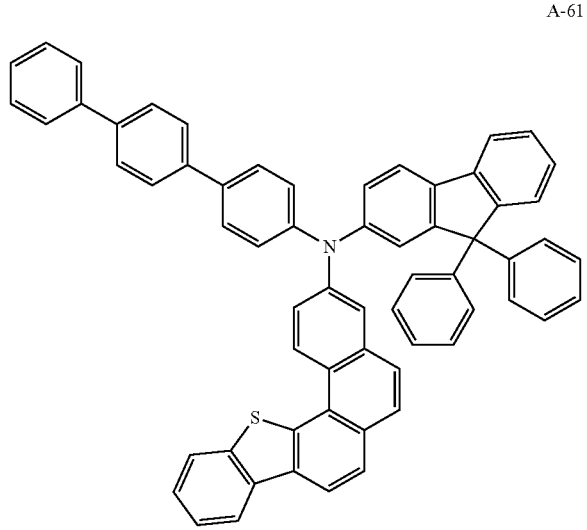
A-64
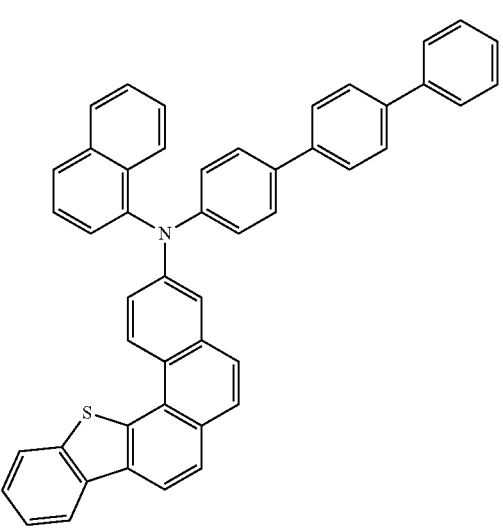

-continued
A-65
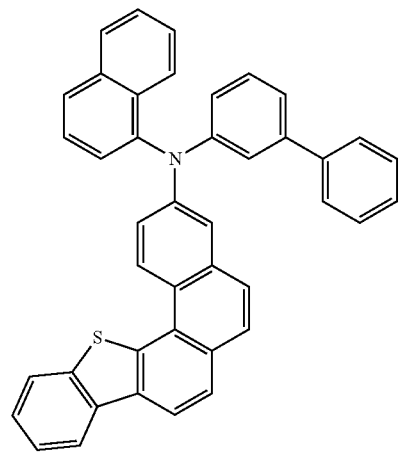
A-66
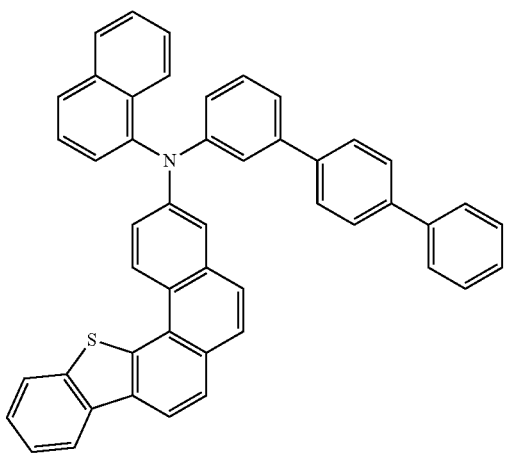
A-67
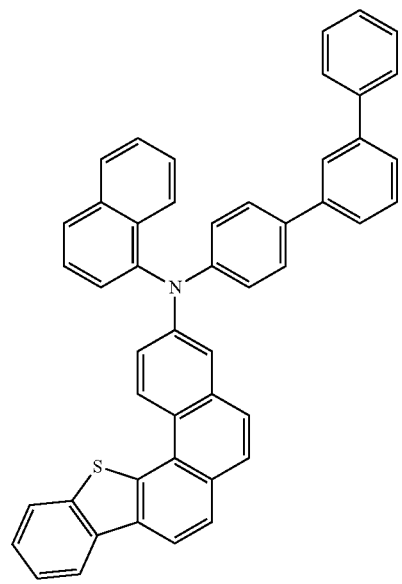
-continued
A-68
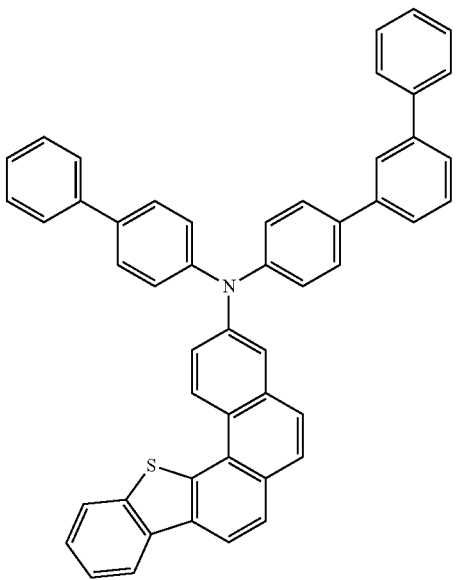
A-70
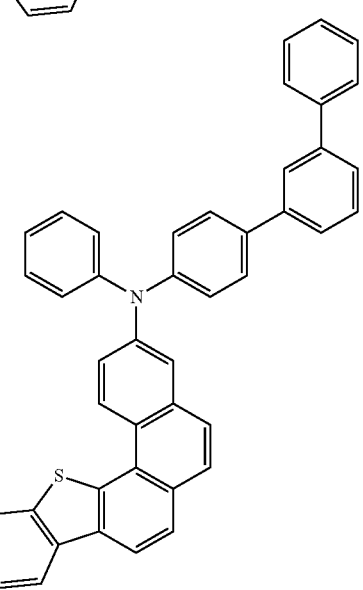
A-71
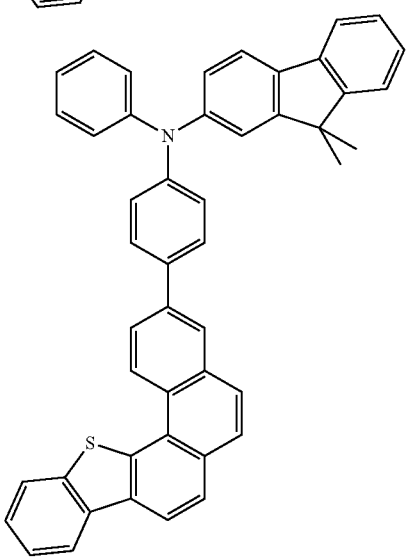

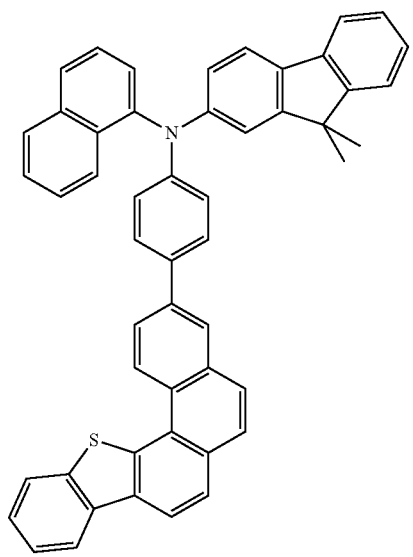
A-72
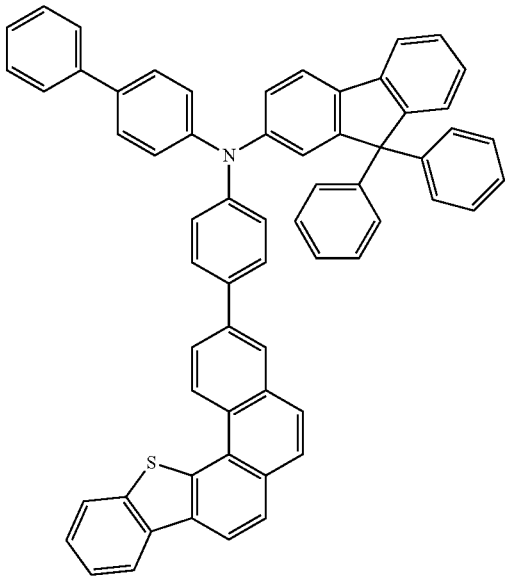
A-74
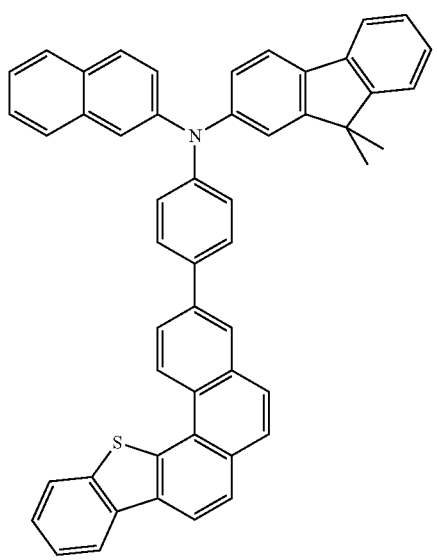
A-73
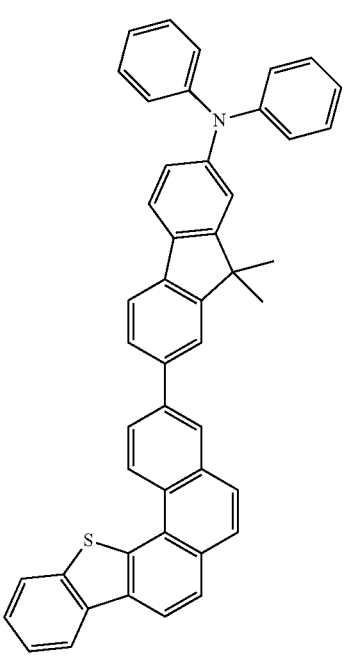
A-75

A-76
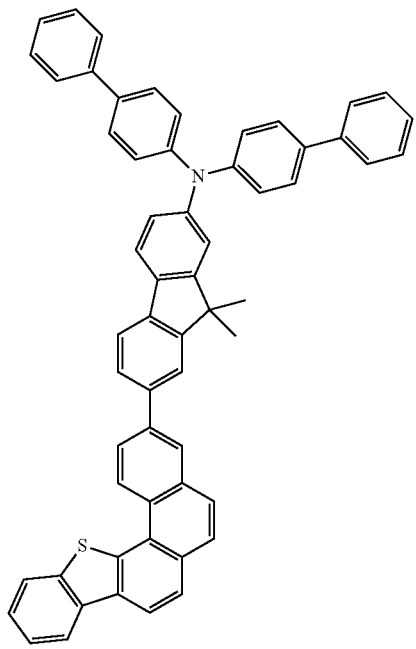
A-78
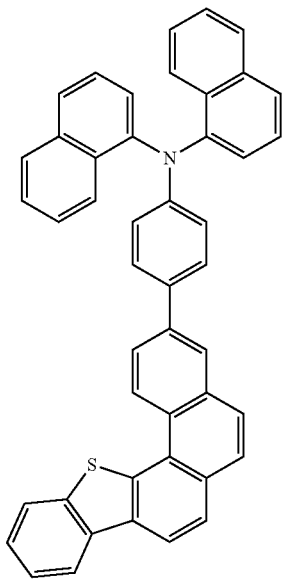
A-77
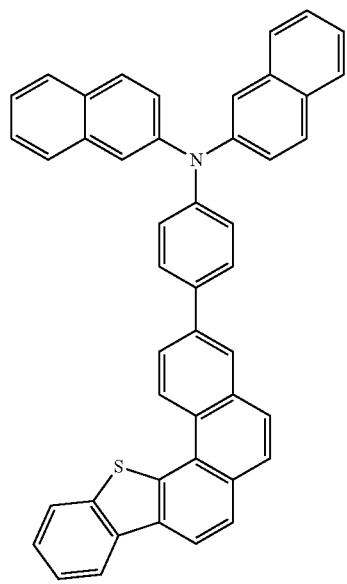
A-79
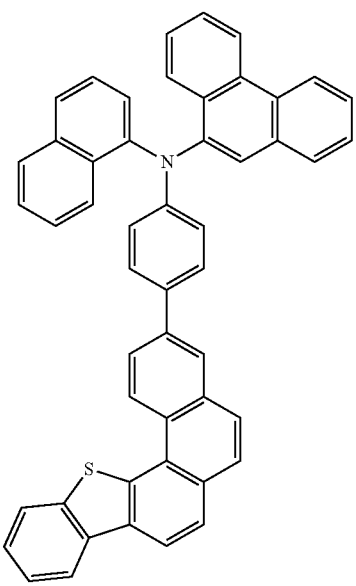

A-93
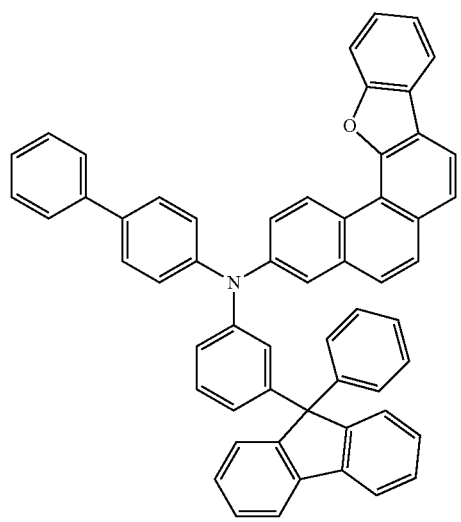
A-96
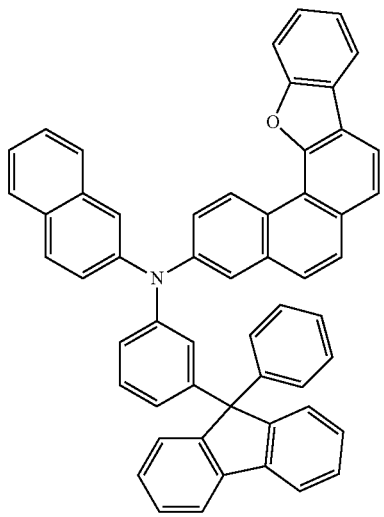
A-94
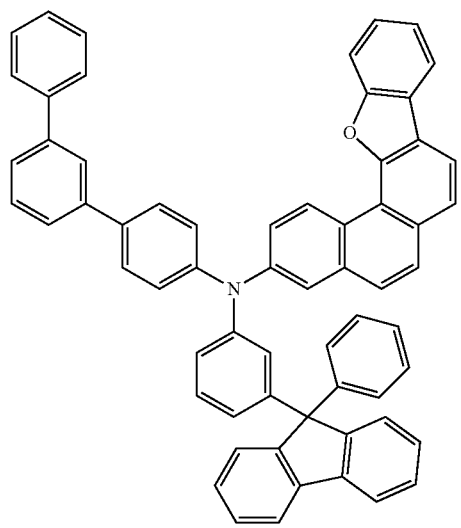
A-97
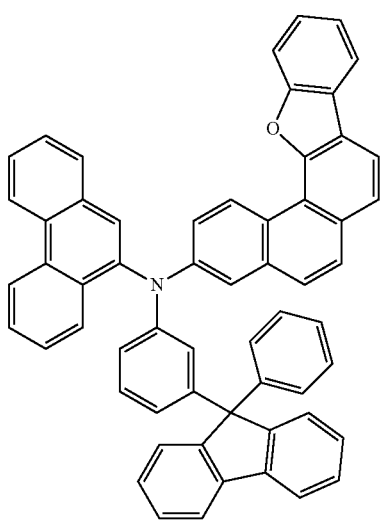
A-95
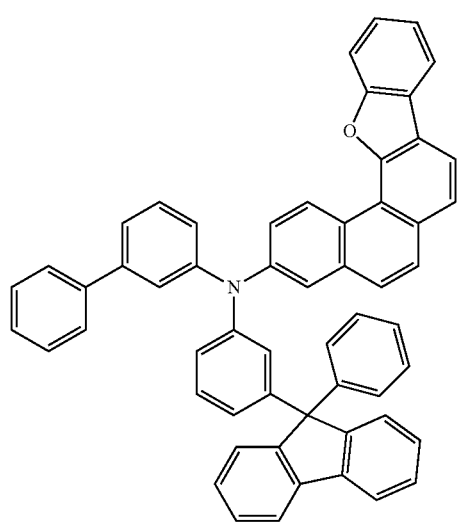
A-98
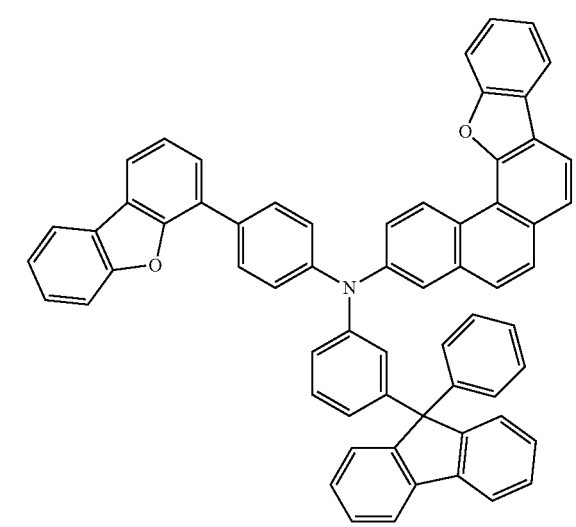

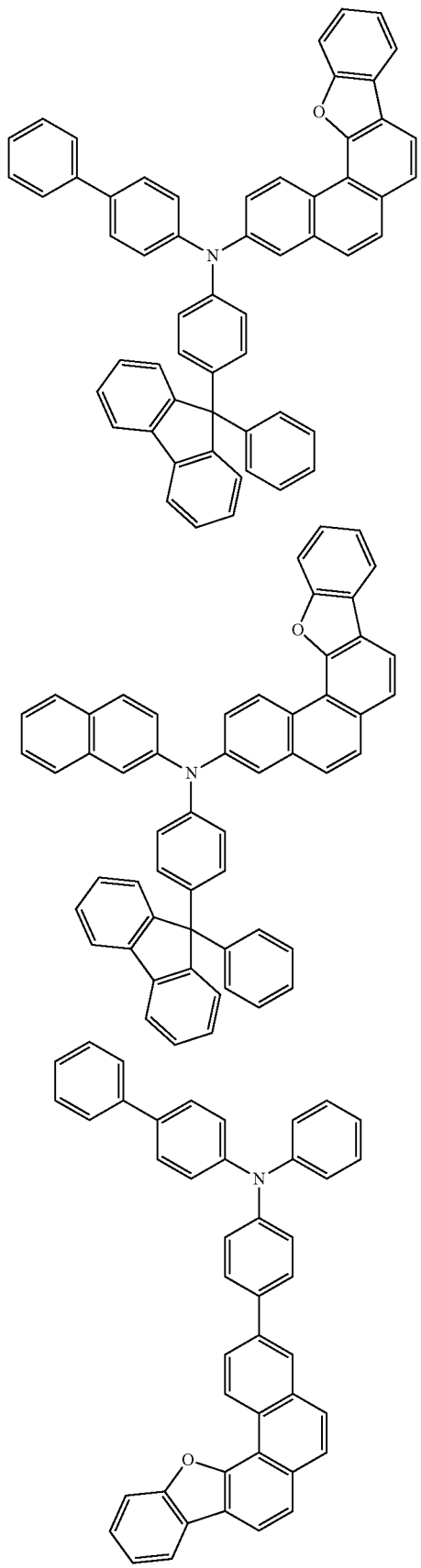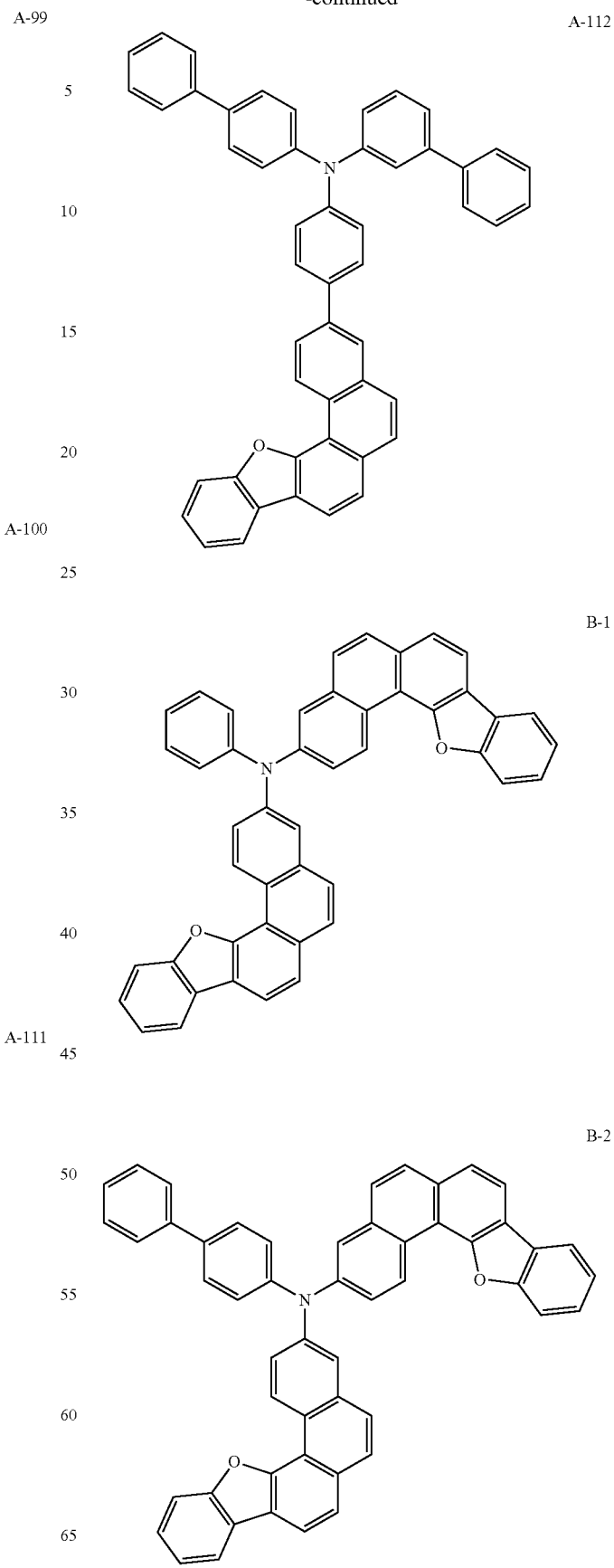

B-3
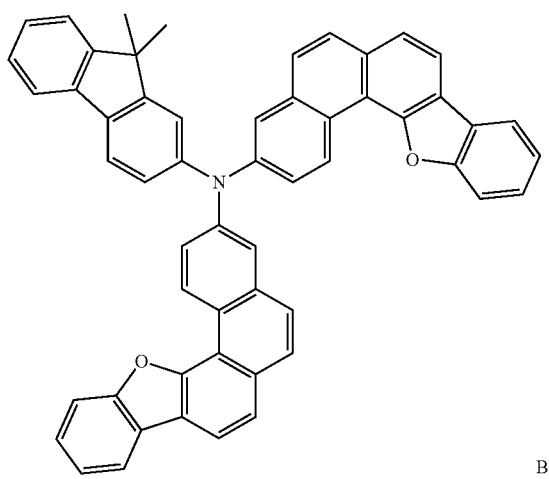
B-4
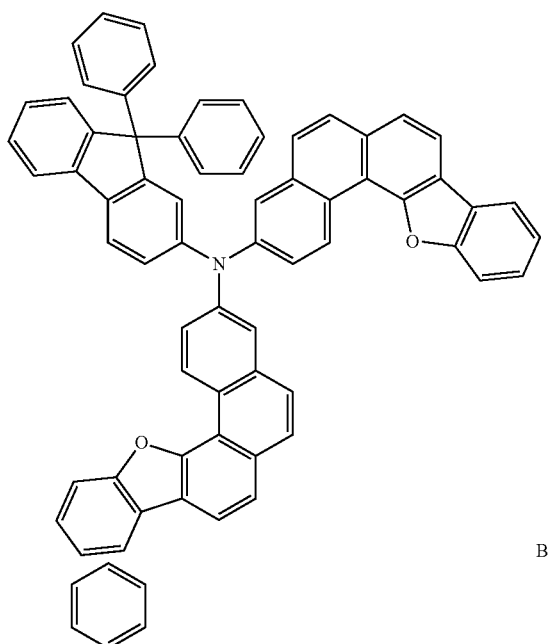
B-6
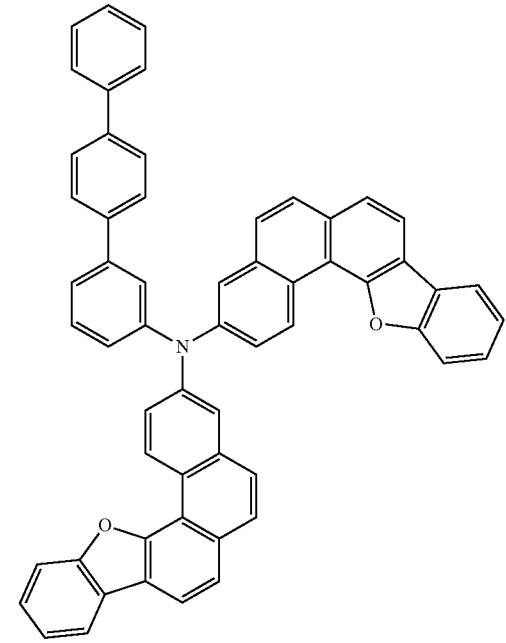
B-7
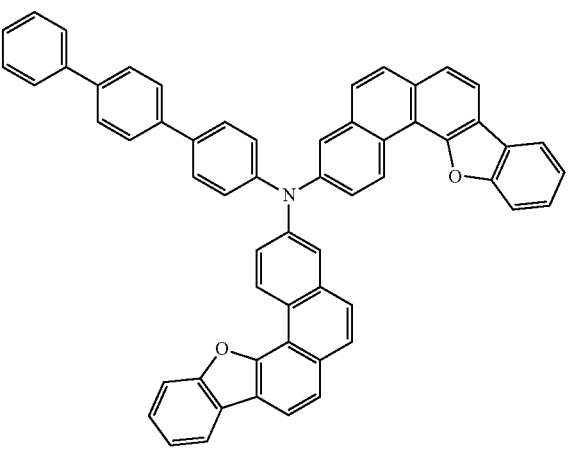
B-8
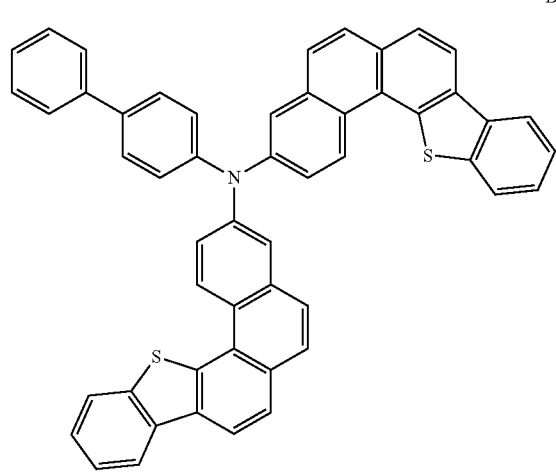
B-9
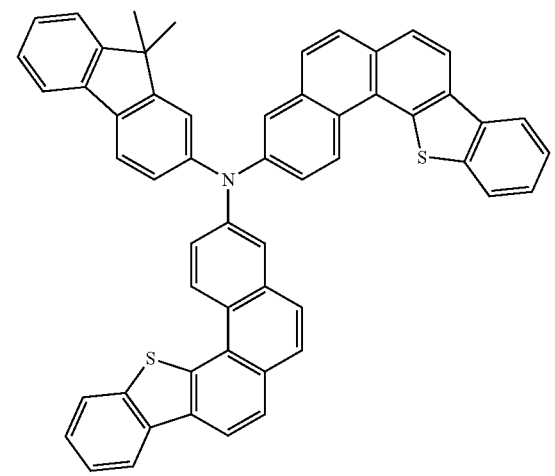

B-10
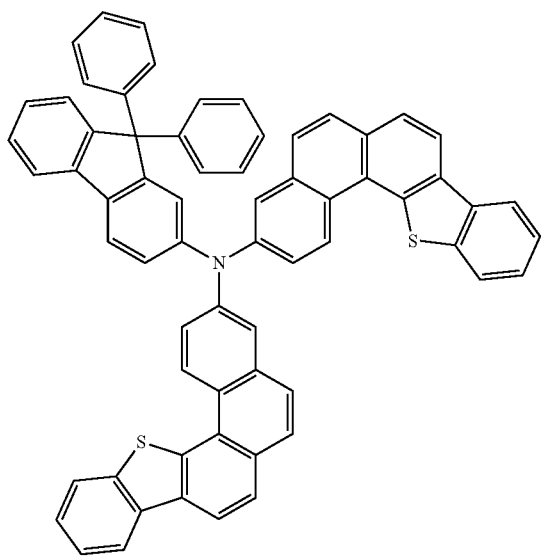
B-13
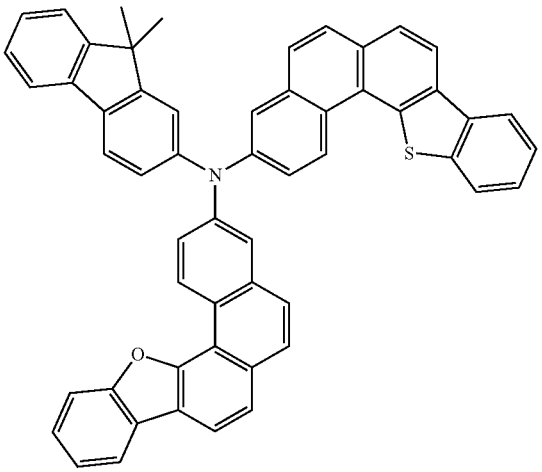
B-11
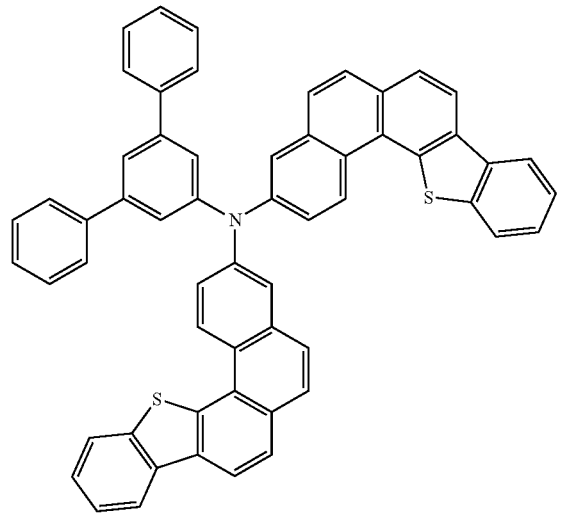
B-14
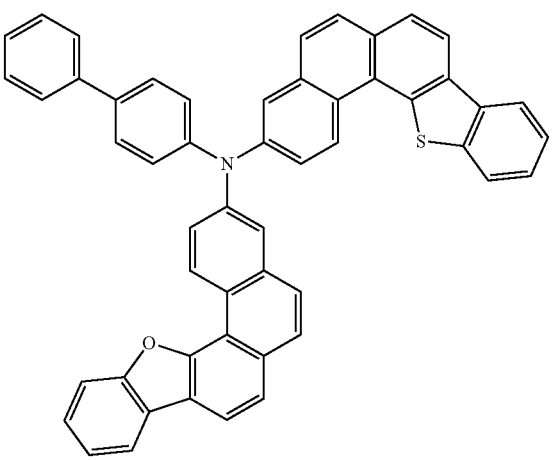
B-12
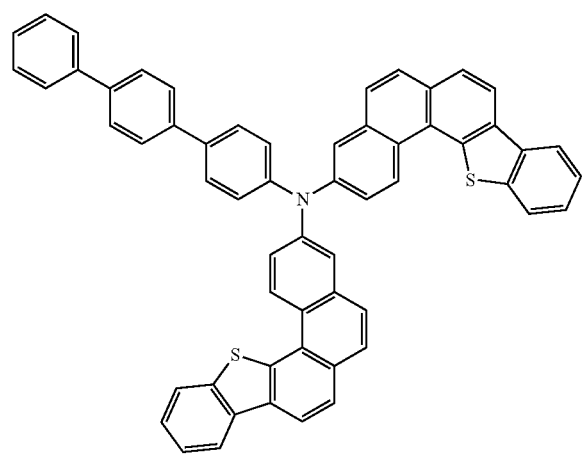
B-15
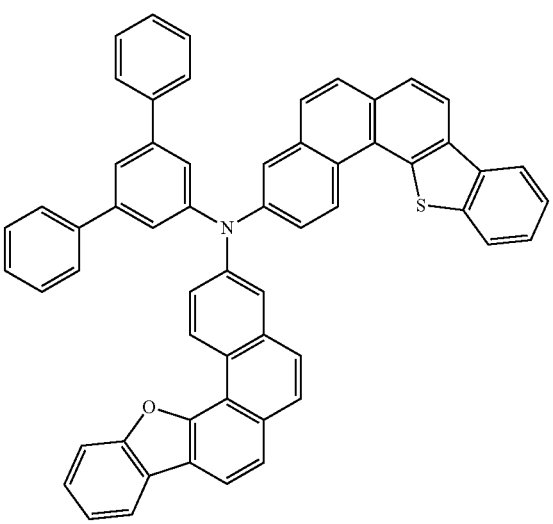

-continued
B-16
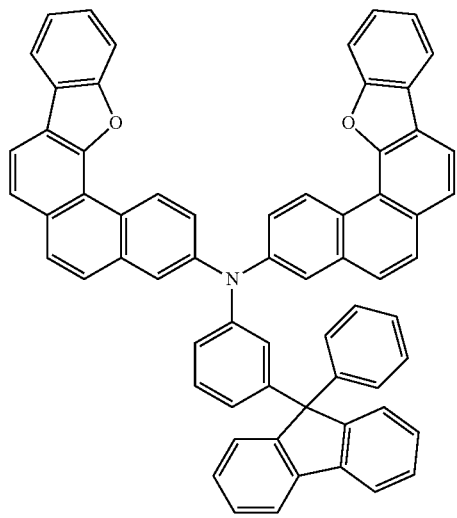
B-17
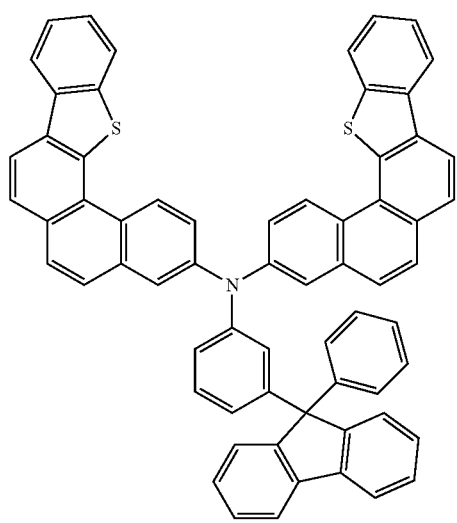
B-18
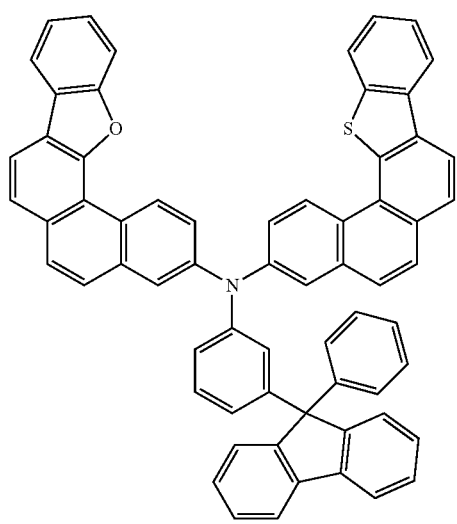
-continued
B-19
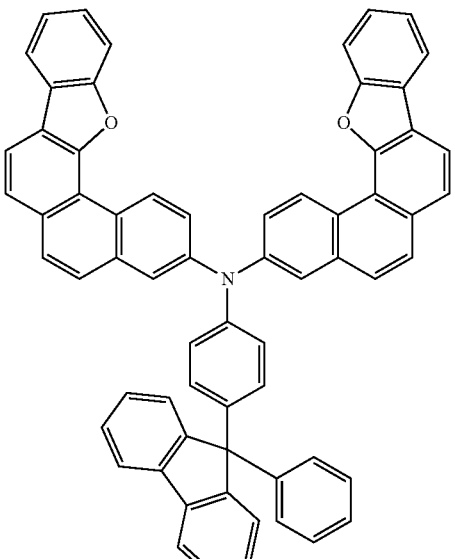
B-20
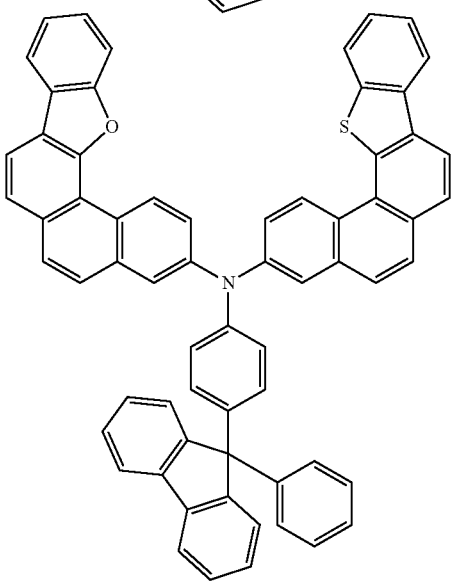
B-21

5. An organic optoelectric diode, comprising:
an anode and a cathode facing each other, and
at least one organic layer positioned between the anode and the cathode,
wherein the organic layer comprises the compound of claim 1.

6. The organic optoelectric diode of claim 5, wherein the organic layer comprises
an emission layer, and
a hole transport layer interposed between the anode and the emission layer,
wherein the organic compound is comprised in the hole transport layer.

7. The organic optoelectric diode of claim 6, wherein the hole transport layer comprises
a first hole transport layer positioned near the anode, and
a second hole transport layer positioned near the emission layer,
wherein the organic compound is comprised in the second hole transport layer.

8. The organic optoelectric diode of claim 7, wherein the first hole transport layer comprises a compound represented by the following Chemical Formula 5:

[Chemical Formula 5]

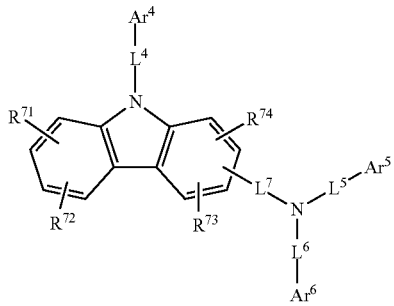

wherein, in Chemical Formula 5,
$R^{71}$ to $R^{74}$ are each independently hydrogen, deuterium, a substituted or unsubstituted C1 to C10 alkyl group, a substituted or unsubstituted C6 to C30 aryl group, a substituted or unsubstituted C2 to C30 heterocyclic group, or a combination thereof,
$R^{71}$ and $R^{72}$ are each independently present or are fused to each other to form a fused ring,
$R^{73}$ and $R^{74}$ are each independently present or are fused to each other to form a fused ring,
$Ar^4$ to $Ar^6$ are each independently a substituted or unsubstituted C6 to C30 aryl group or a substituted or unsubstituted C2 to C30 heterocyclic group, and
$L^4$ to $L^7$ are independently a single bond, a substituted or unsubstituted C2 to C10 alkylene group, a substituted or unsubstituted C2 to C10 alkenylene group, a substituted or unsubstituted C2 to C10 alkynylene group, a substituted or unsubstituted C6 to C30 arylene group, a substituted or unsubstituted C2 to C30 heterocyclic group or a combination thereof.

9. The organic optoelectric diode of claim 8, wherein $Ar^4$ of Chemical Formula 5 is a substituted or unsubstituted phenyl group, or a substituted or unsubstituted biphenyl group, and
$Ar^5$ and $Ar^6$ of Chemical Formula 5 are independently one of a substituted or unsubstituted phenyl group, a substituted or unsubstituted biphenyl group, a substituted or unsubstituted fluorene group, a substituted or unsubstituted bisfluorene group, a substituted or unsubstituted triphenylene group, a substituted or unsubstituted anthracene group, a substituted or unsubstituted terphenyl group, a substituted or unsubstituted dibenzofuran group or a substituted or unsubstituted dibenzothiophenyl group.

10. A display device comprising the organic optoelectric diode of claim 5.

11. An organic optoelectric diode, comprising:
an anode and a cathode facing each other, and
at least one organic layer positioned between the anode and the cathode,
wherein the organic layer comprises the compound of claim 4.

12. A display device comprising the organic optoelectric diode of claim 11.

* * * * *